United States Patent [19]

Kogasaka

[11] Patent Number: 5,797,928
[45] Date of Patent: Aug. 25, 1998

[54] LIGATING APPARATUS

[75] Inventor: Takahiro Kogasaka, Hachioji, Japan

[73] Assignee: Olympus Optical Co., Ltd., Tokyo, Japan

[21] Appl. No.: 581,181

[22] Filed: Dec. 29, 1995

[30] Foreign Application Priority Data

Jan. 20, 1995 [JP] Japan ................................. 7-007226
Dec. 26, 1995 [JP] Japan ................................. 7-339067

[51] Int. Cl.$^6$ .................................................. A61B 17/04
[52] U.S. Cl. ...................... 606/144; 606/139; 606/148
[58] Field of Search ............................... 606/144, 148, 606/139

[56] References Cited

U.S. PATENT DOCUMENTS

| | | |
|---|---|---|
| 3,687,138 | 8/1972 | Jarvik . |
| 5,312,423 | 5/1994 | Rosenbluth et al. . |
| 5,336,229 | 8/1994 | Noda . |
| 5,336,230 | 8/1994 | Leichtling et al. . |
| 5,336,231 | 8/1994 | Adair . |
| 5,391,176 | 2/1995 | de la Torre . |
| 5,454,820 | 10/1995 | Kammerer et al. ............... 606/148 |
| 5,472,446 | 12/1995 | De La Torre .................... 606/139 |
| 5,536,273 | 7/1996 | Lehrer ............................ 606/139 |
| 5,609,597 | 3/1997 | Lehrer ............................ 606/139 |

FOREIGN PATENT DOCUMENTS

| | | |
|---|---|---|
| 0634143 A2 | 1/1995 | European Pat. Off. . |
| 2326110 | 4/1977 | France ............................ 606/144 |
| 6-54855 | 3/1994 | Japan . |
| 006714 | 2/1898 | United Kingdom ............. 606/144 |

*Primary Examiner*—Gary Jackson
*Attorney, Agent, or Firm*—Frishauf, Holtz, Goodman, Langer & Chick

[57] ABSTRACT

A ligating apparatus comprising a ligature applying device having at a distal end a ligature holding section for holding a ligature; a ligature holding device movable relative to the ligature applying device, the ligature holding device having a through hole through which the ligature-applying device is to be moved, ligature holding mechanism for holding one end of the ligature, and a ligature retaining section for retaining the ligature; ligature winding mechanism for winding the ligature around the ligature applying device or the ligature holding device, thereby to form at least one loop to be tightened into a knot; loop releasing mechanism for releasing the loop from the ligature applying device or the ligature holding device when the ligature applying device is pulled into the through hole of the ligature holding device; and loop tightening mechanism for tightening the loop released from the ligature applying device or the ligature holding device, when the ligature applying device and the ligature holding device are moved relative to each other.

50 Claims, 40 Drawing Sheets

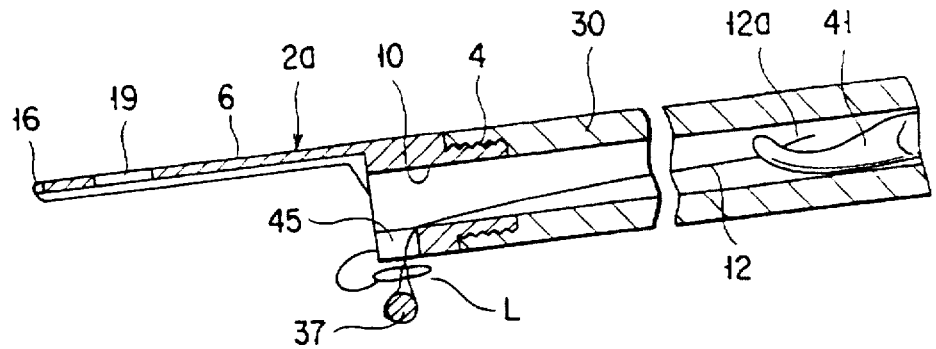
F I G. 22
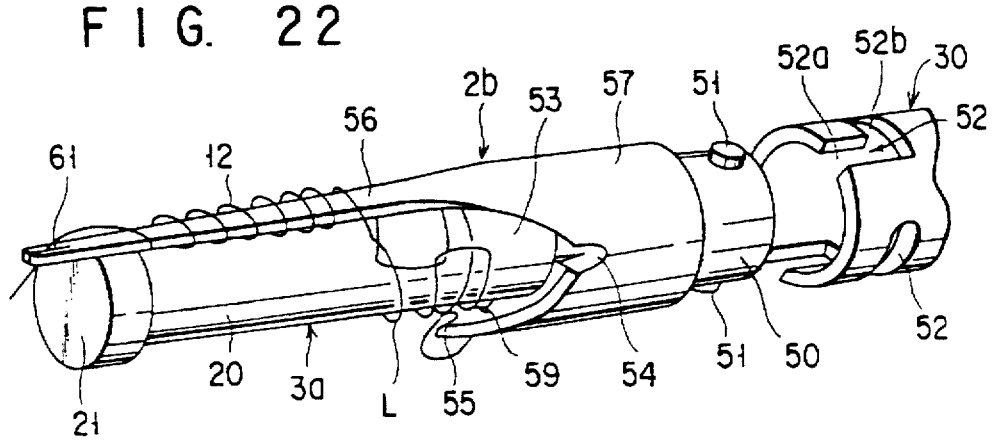
F I G. 23
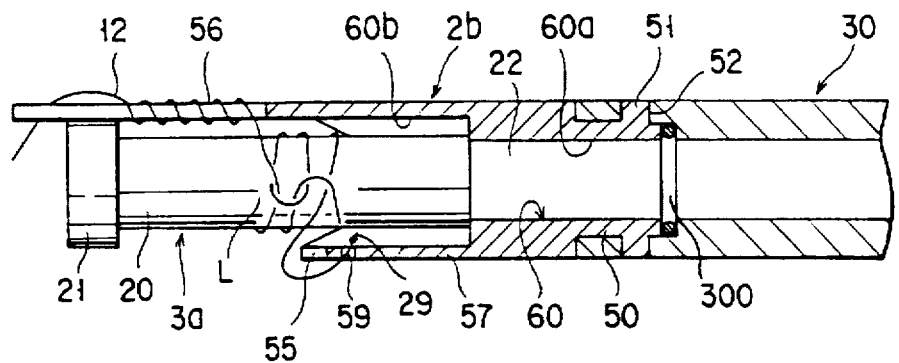
F I G. 24
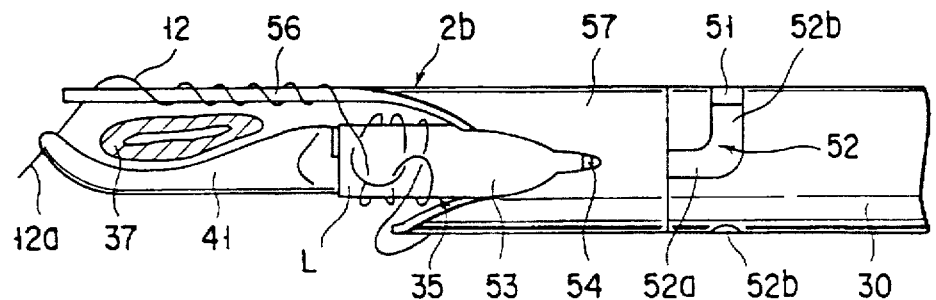
F I G. 25

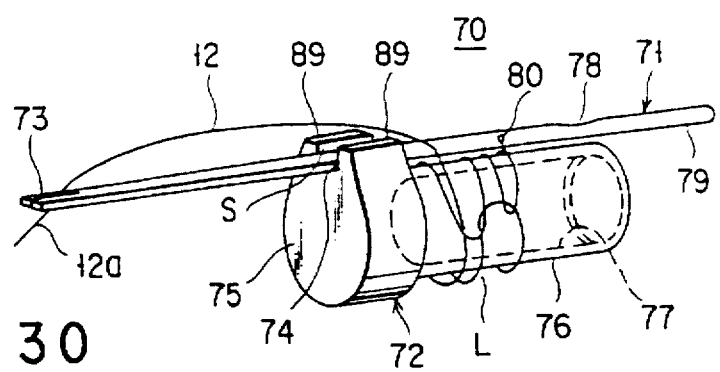
F I G. 30
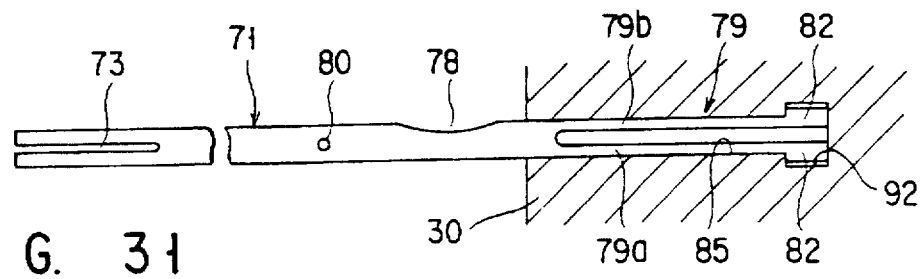
F I G. 31
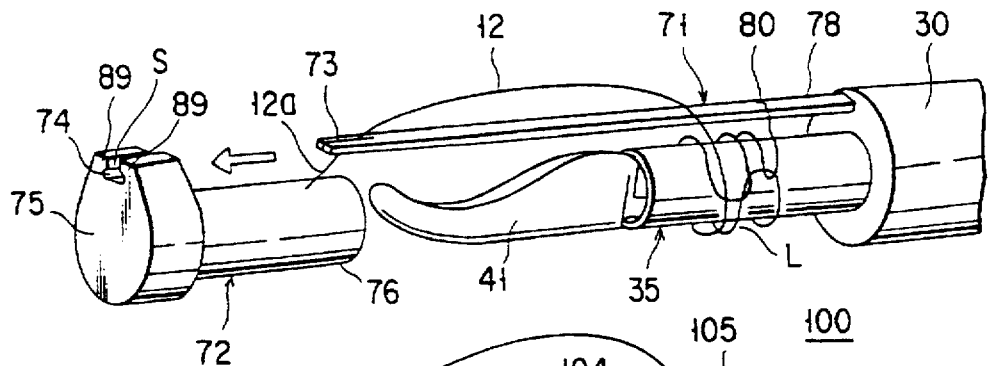
F I G. 32
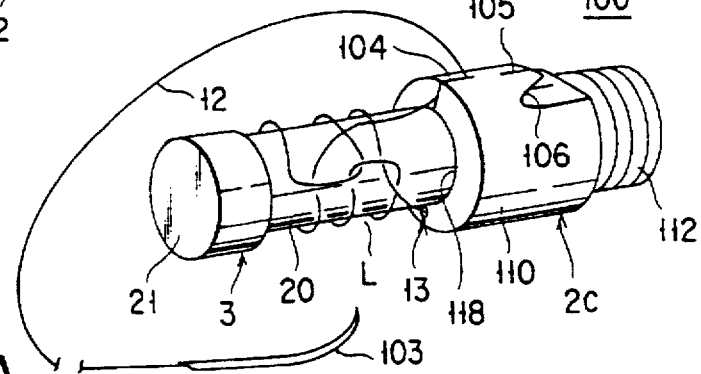
F I G. 33A
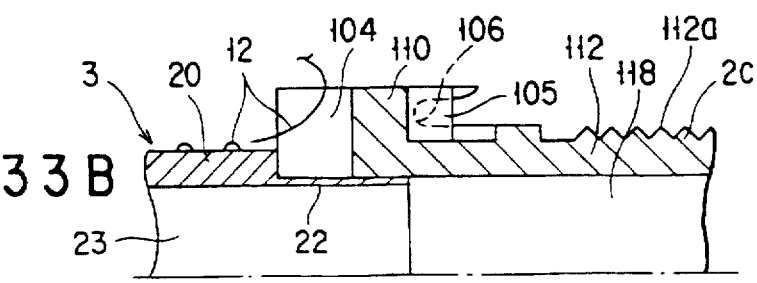
F I G. 33B

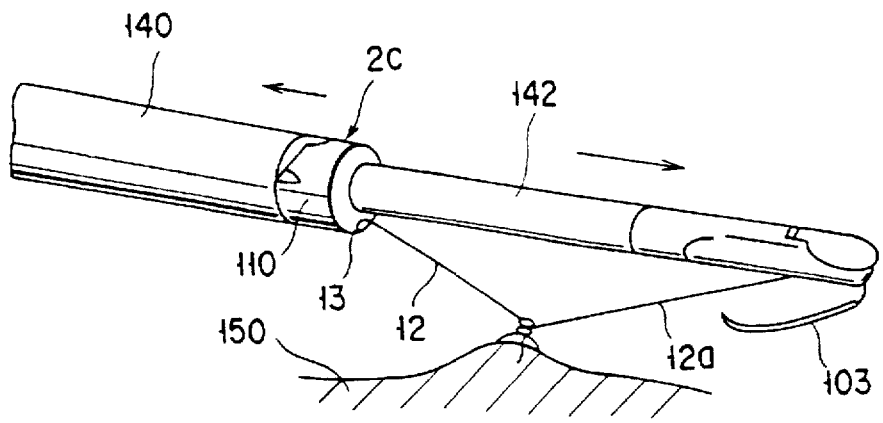
F I G. 38
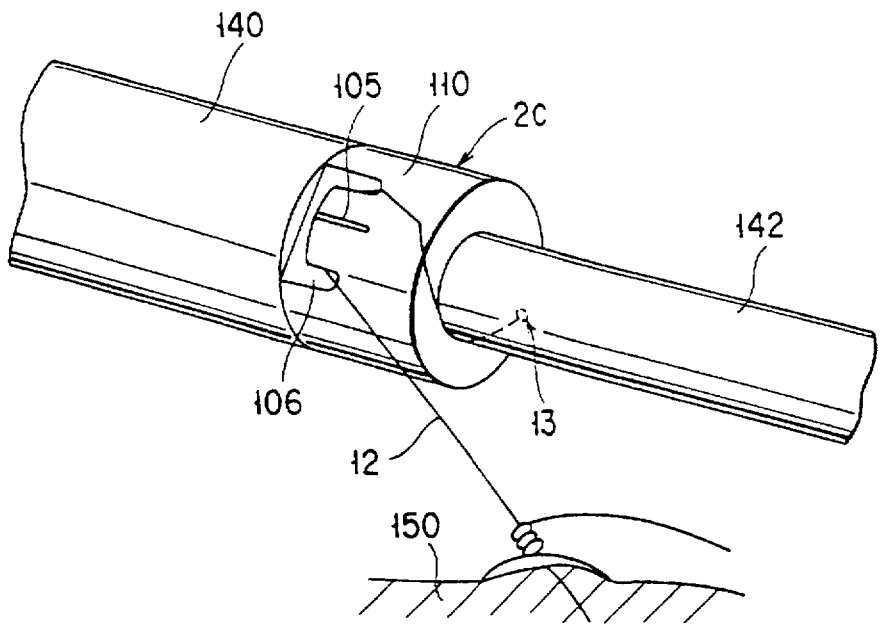
F I G. 39A
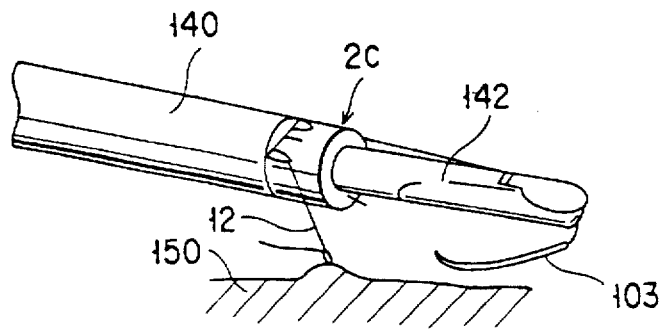
F I G. 39B

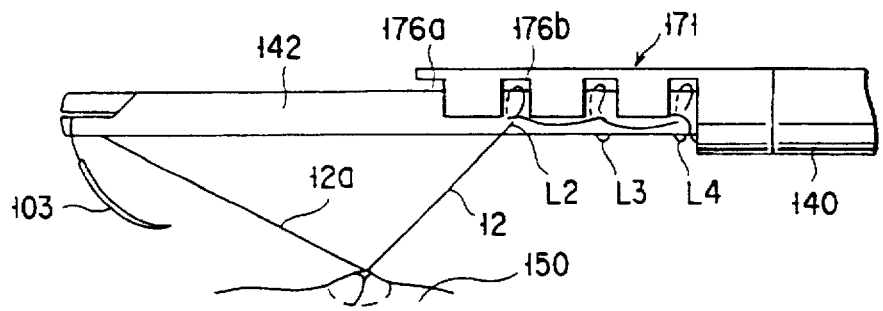
F I G. 45
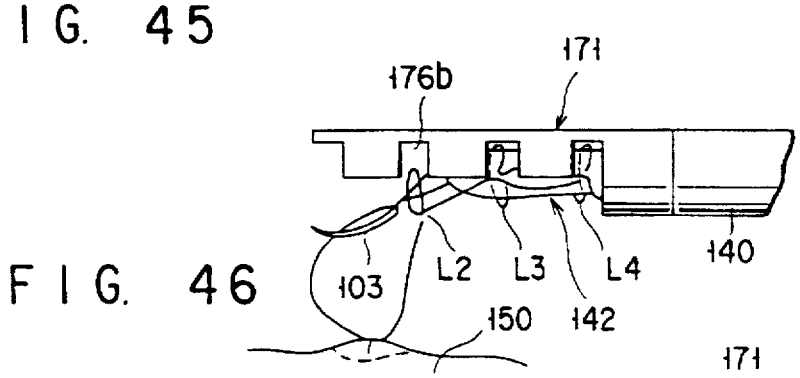
F I G. 46
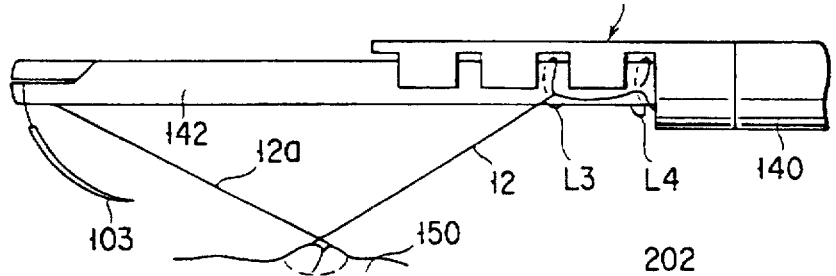
F I G. 47
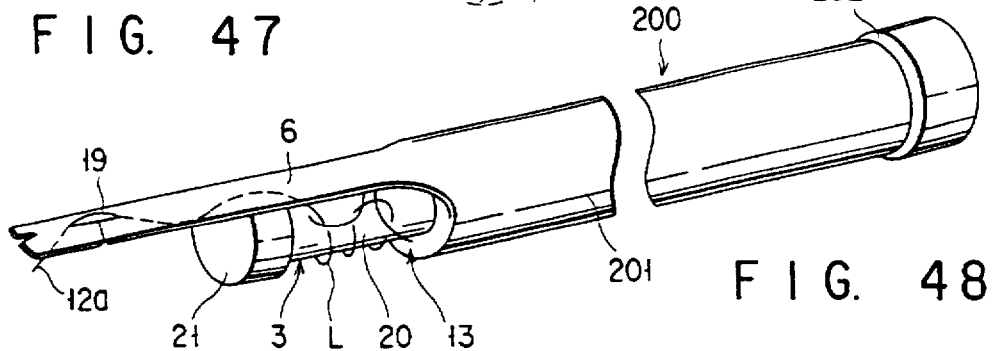
F I G. 48
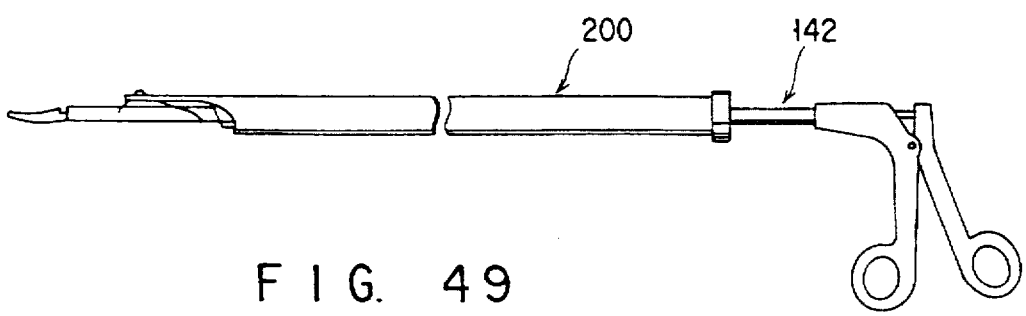
F I G. 49

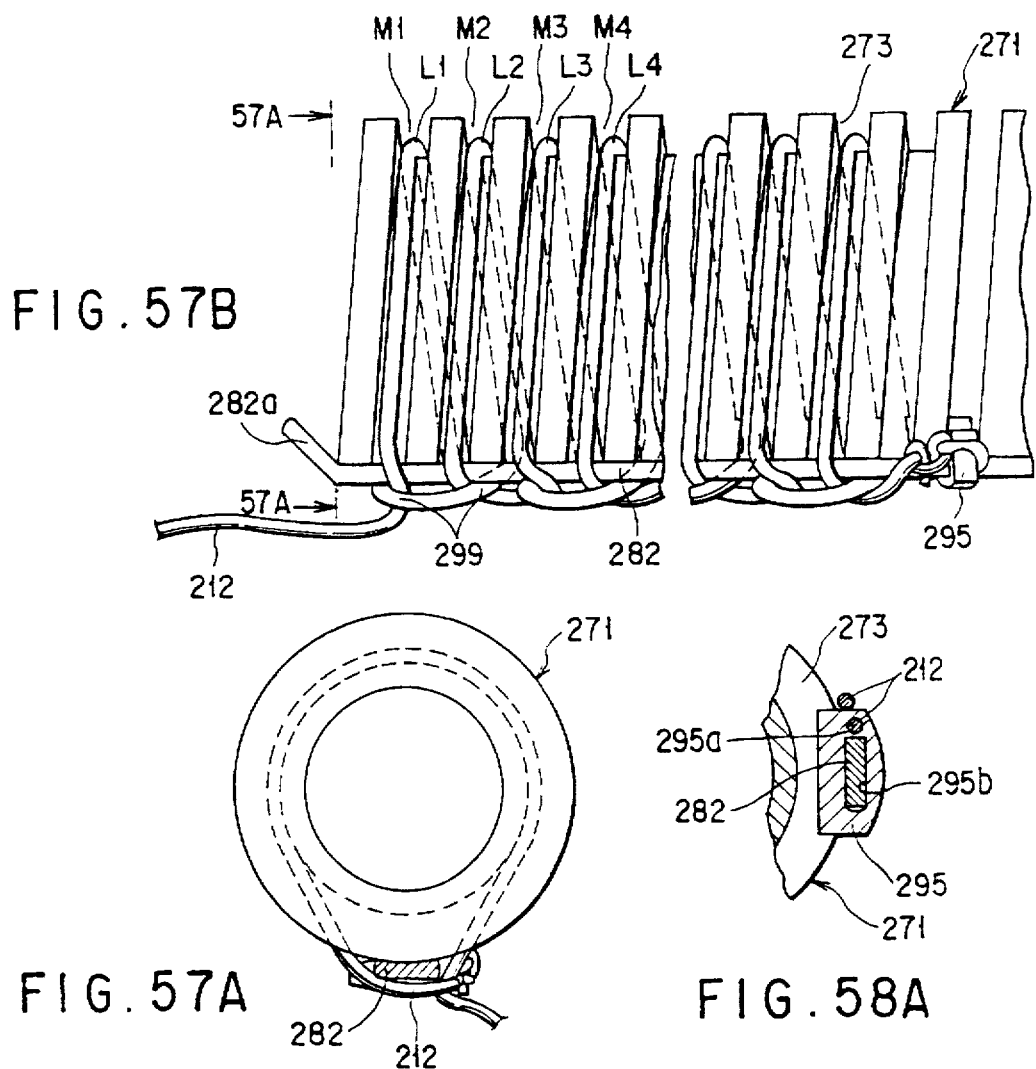
FIG. 57B
FIG. 57A
FIG. 58A
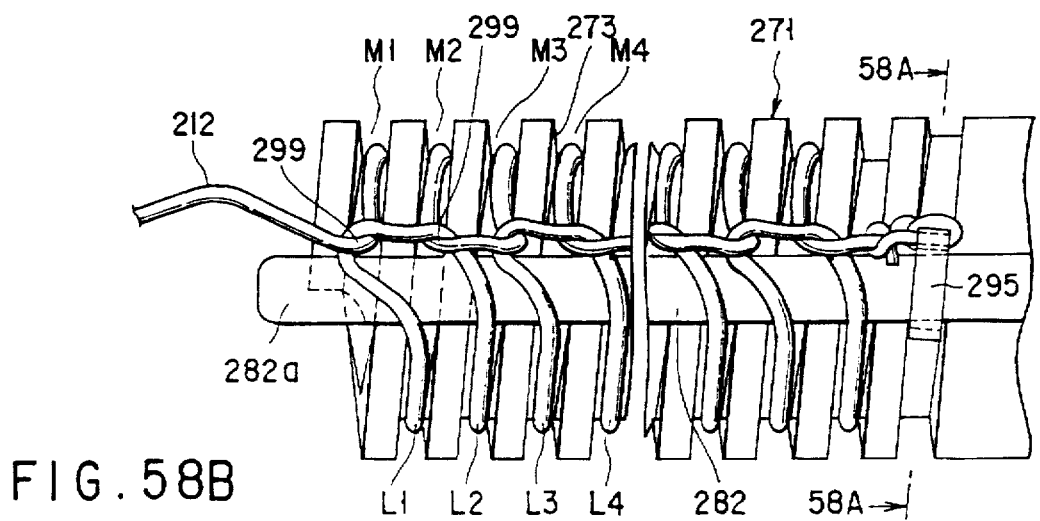
FIG. 58B

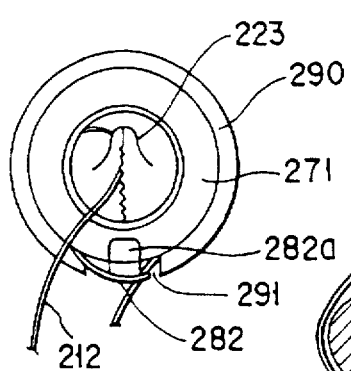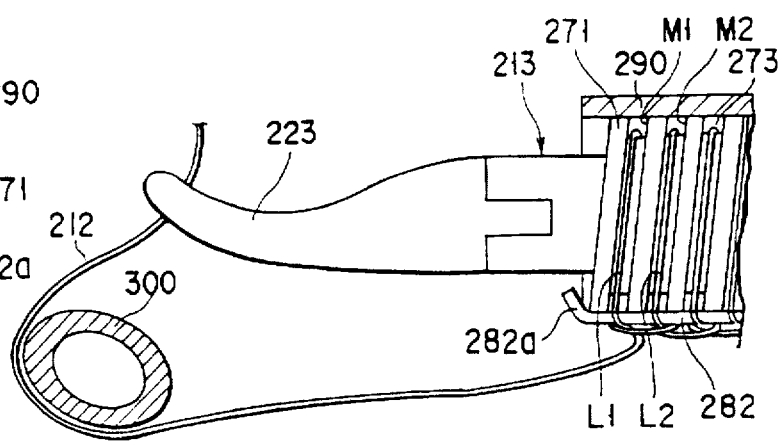
FIG. 59A  FIG. 59B
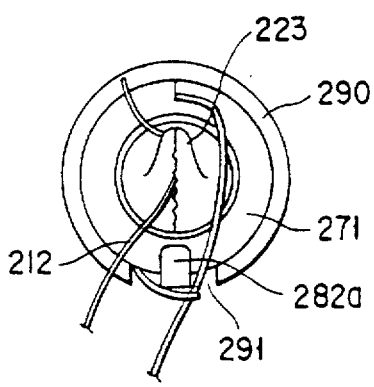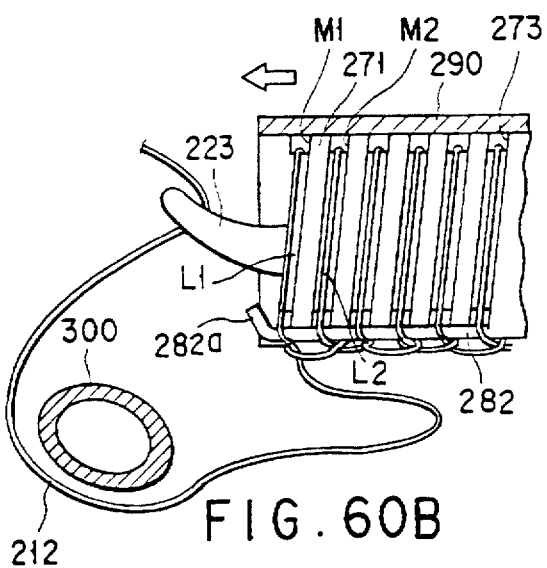
FIG. 60A  FIG. 60B
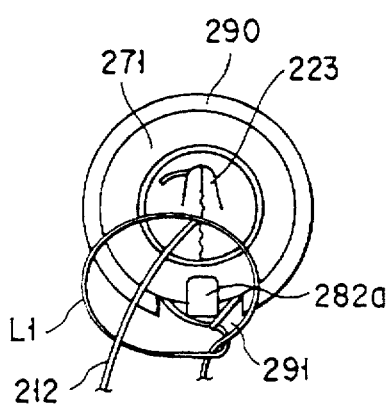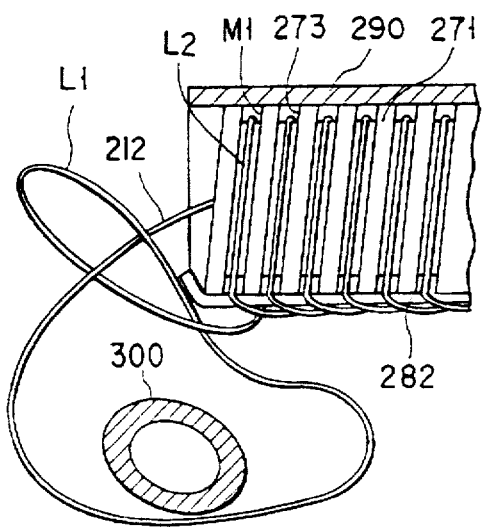
FIG. 61A  FIG. 61B

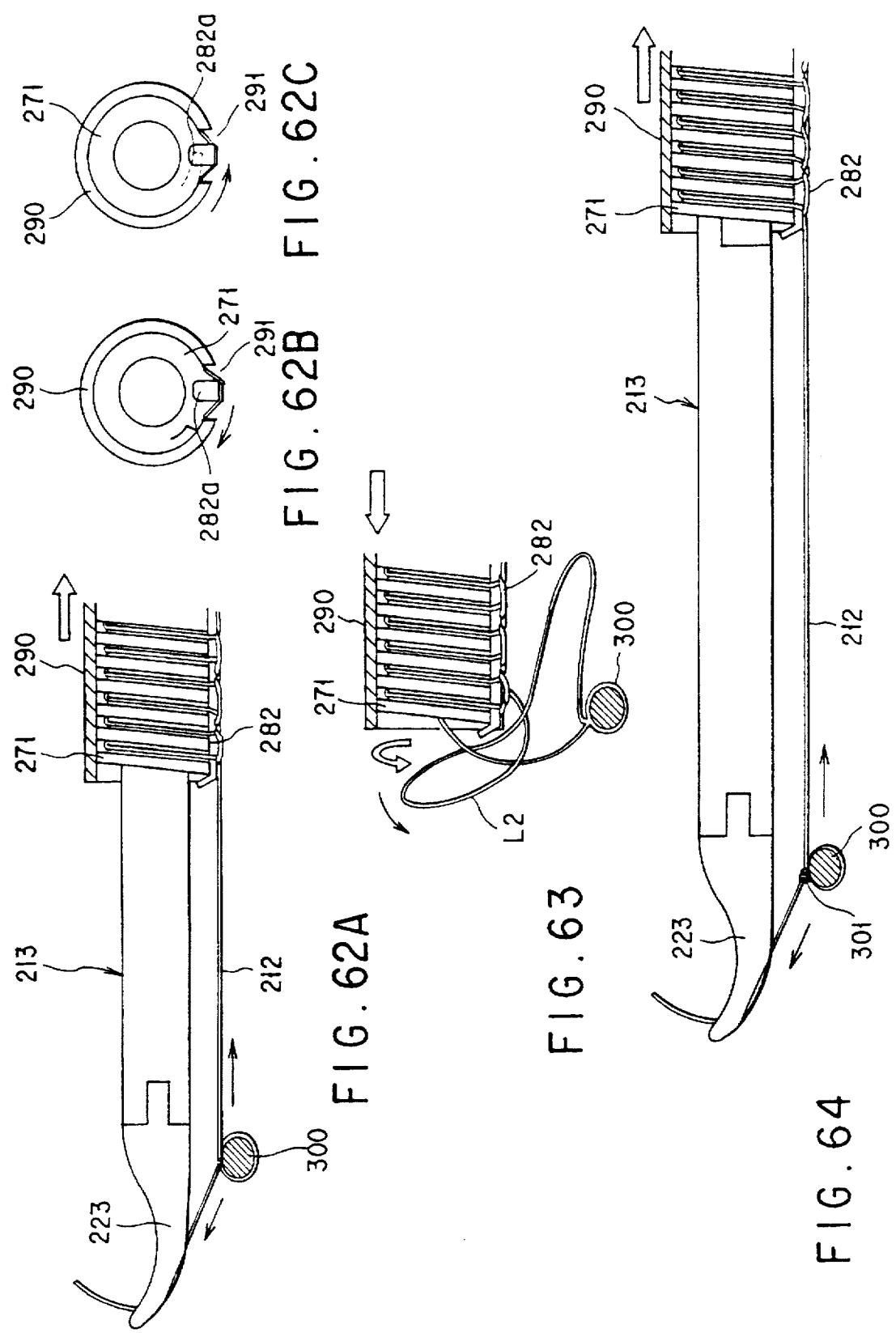

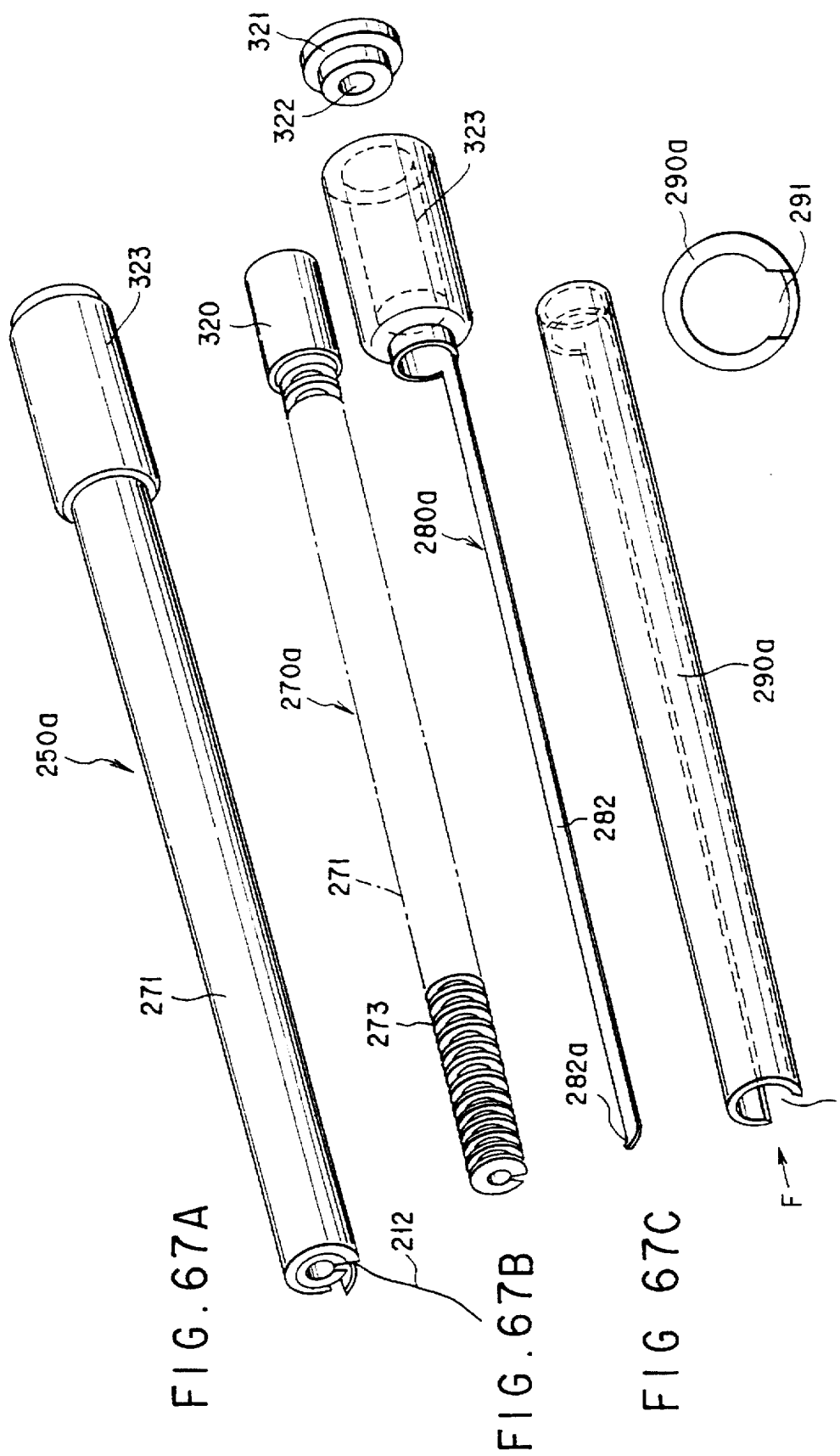

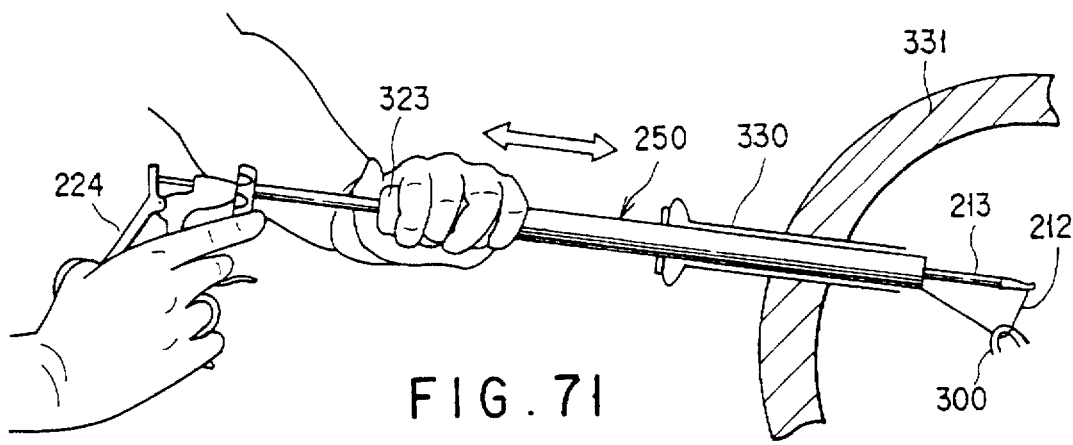
FIG. 71
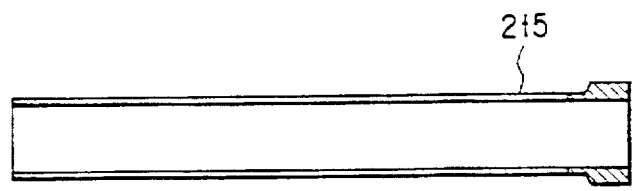
FIG. 72A
FIG. 72B
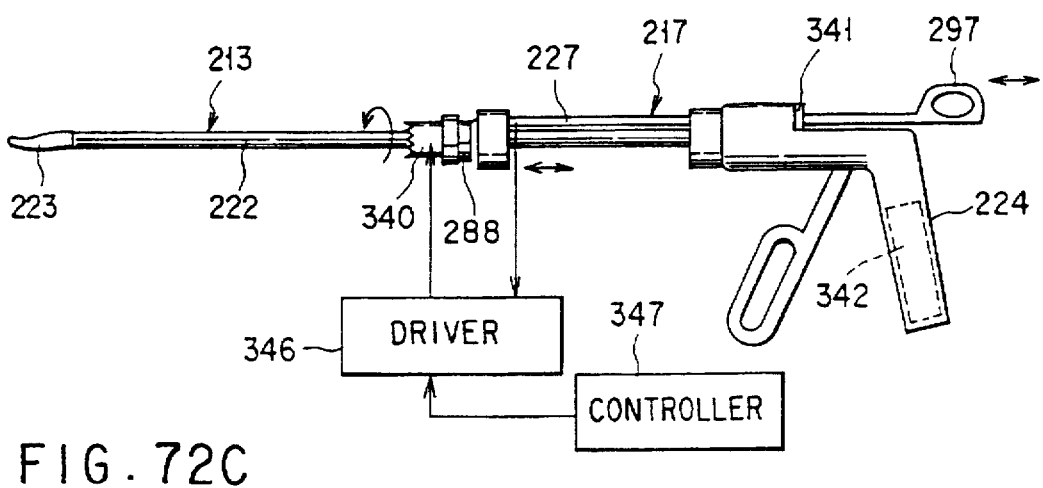
FIG. 72C

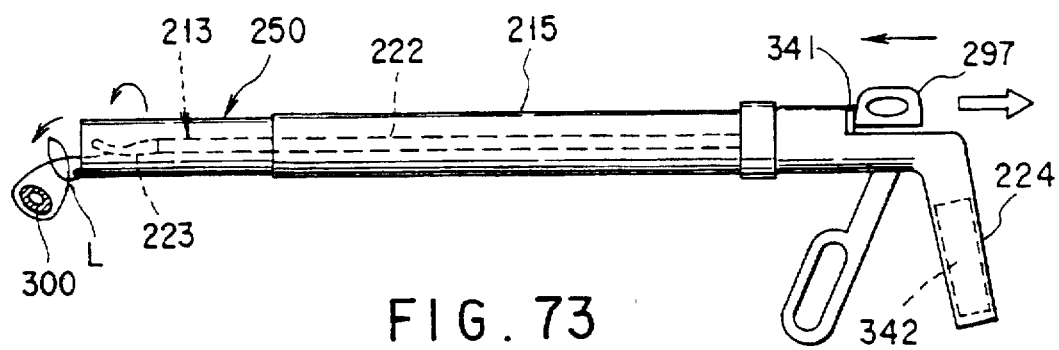
FIG. 73
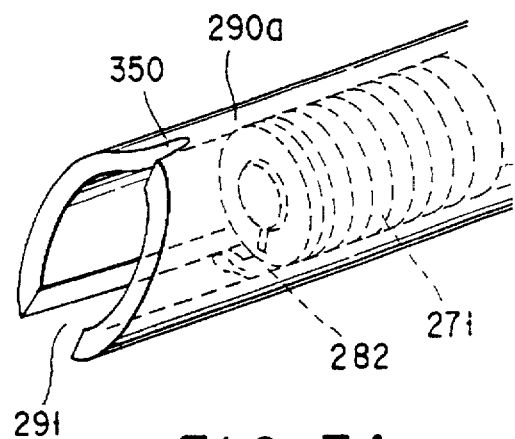
FIG. 74
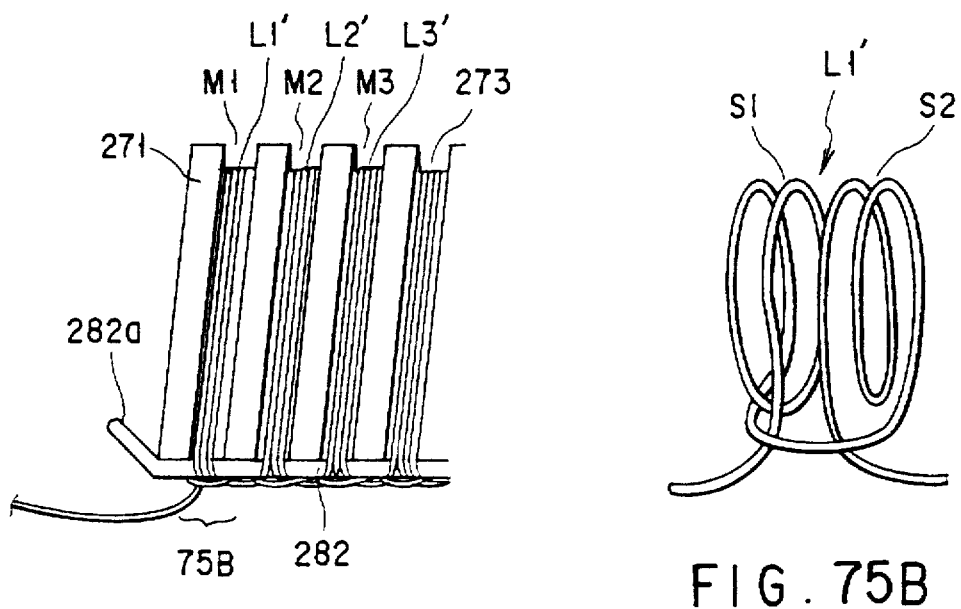
FIG. 75A
FIG. 75B

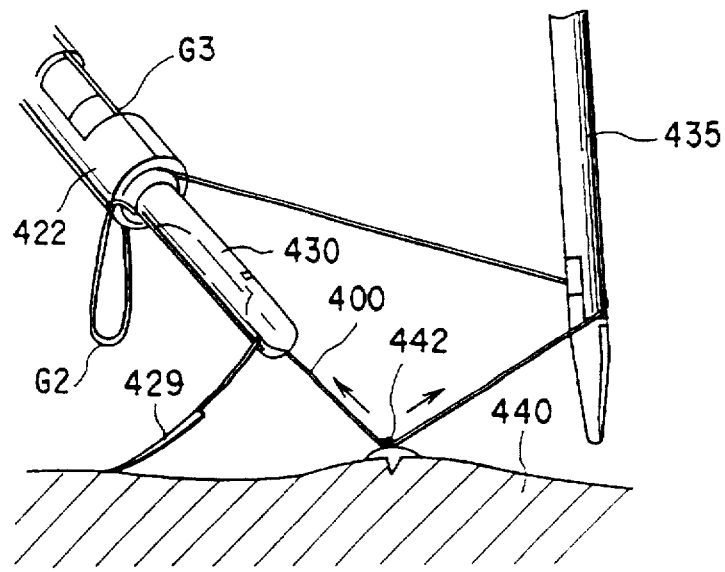
FIG. 94
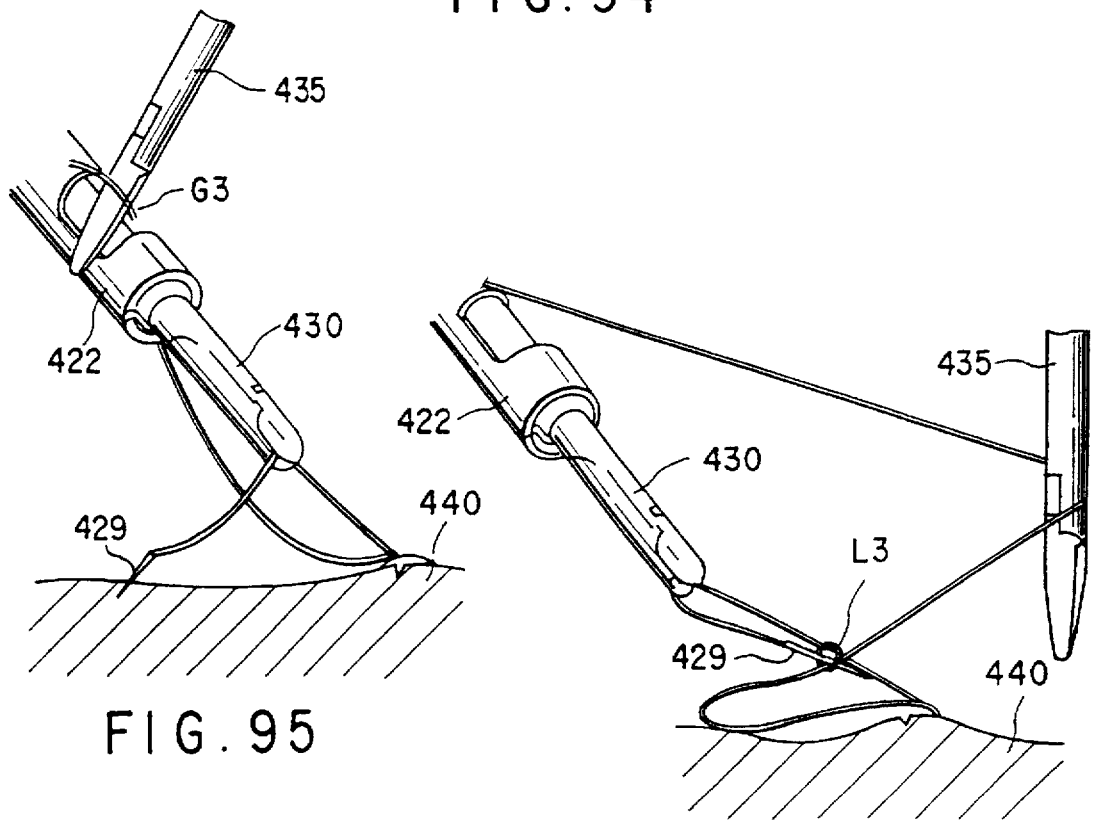
FIG. 95
FIG. 96

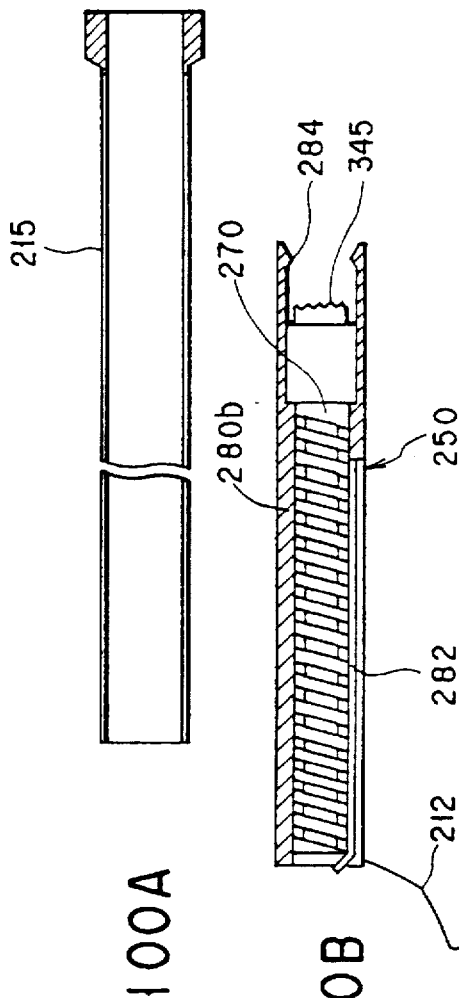
FIG.100A
FIG.100B
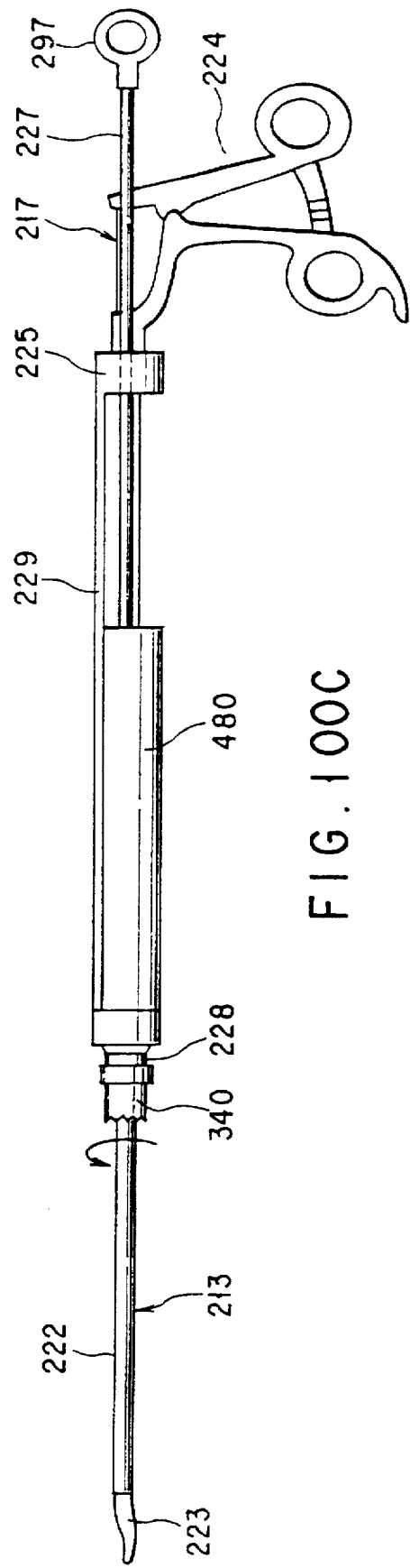
FIG.100C

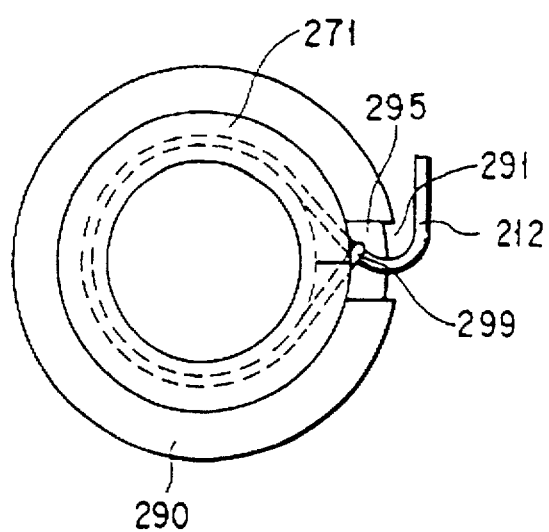
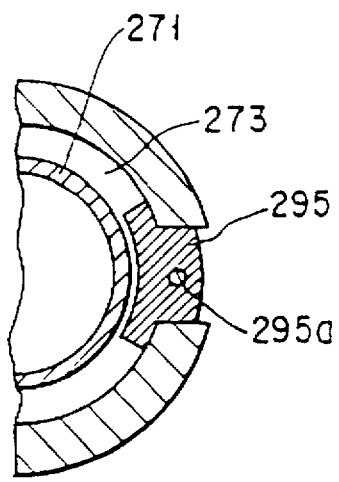
FIG. 102A  FIG. 102B
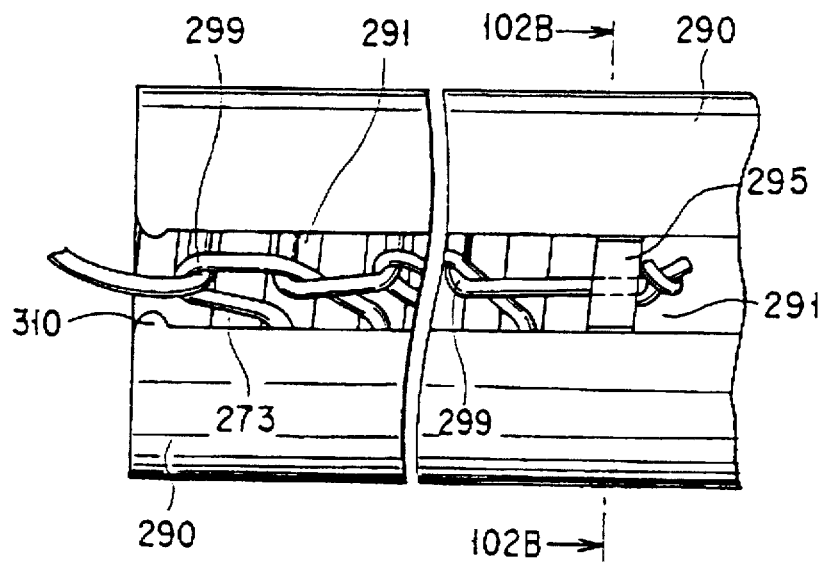
FIG. 102C

LIGATING APPARATUS

BACKGROUND OF THE INVENTION

1. Field of the Invention

The present invention relates to a ligating apparatus for use in suture or ligation in surgical operations and, more particularly, to a ligating apparatus designed for use in endoscopic surgical operations.

2. Description of the Related Art

In most surgical operations a surgeon ligates many blood vessels and sutures many tissues. Of these surgical works, the work of forming knots is the most time-consuming.

Recently endoscopic surgical operations are performed in increasing numbers. It is difficult for surgeons to ligate blood vessels or suture tissues by manipulating special instruments inserted into a body cavity which is rather small, while observing a endoscopic image displayed on a monitor. To help the surgeons to form knots of threads, various ligating devices and methods have been developed.

Ligation is classified to types, i.e., extracorporeal ligation and intracorporeal ligation. Extracorporeal ligation comprises the steps of passing a ligature under the tissue of interest, drawing both ends of the ligature out of the body, forming a knot outside the body, and putting the knot into the body cavity by means of an instrument called "knot pusher." In intracorporeal litigation, a surgeon binds the ends of a ligature, forming a knot, in the body cavity by using two forceps inserted in the body cavity.

Ligating apparatuses which facilitate the forming of knots in intracorporeal ligation are disclosed in Jpn. Pat. Appln. KOKAI Publication 6-54855. Some other ligation apparatuses which enable surgeons to form knots easily in extracorporeal ligation are known, too. Further, U.S. Pat. Nos. 5,336,229, 5,336,231 and 5,312,423 disclose ligating apparatuses designed to ligate tubular tissues (e.g., blood vessels) in endoscopic surgical operations, which can be inserted into a body cavity through one opening incised in the body wall.

As mentioned above, extracorporeal ligation comprises the steps of passing a ligature under the tissue, drawing the ends of the ligature from the body, forming a knot outside the body, and putting the knot into the body cavity. The surgeon needs to insert the instruments into the body cavity, pull them therefrom and replace instruments with others, inevitably spending much time. As the ligature is pulled from the body along a relatively long path, it may graze the tissue located at the path. Obviously, the surgeon should have much more skill to handle two forceps in intracorporeal ligation than to manipulate the forceps in celiotomy, because the surgeon can see an endoscopic image of the tissue of interest but cannot observe the tissue itself.

Methods of performing ligation, either extracorporeal or intracorporeal ligation, are classified into two types. Methods of the first type are described in Jpn. Pat. Appln. KOKAI Publication 6-54855 and U.S. Pat. No. 5,312,423, and methods of the second type are disclosed in U.S. Pat. Nos. 5,336,229 and 5,336,231.

In the method of the first type, the ligature is wrapped around the tissue and pulled straight at one end. Then, the other end portion is wound around the straightened end portion, forming a running knot thereon. As a result, the ligature forms a running noose around the tissue. The running knot is moved toward the tissue, sliding on the straightened end portion, until the running noose tightens the tissue. The noose tightens the tissue but not so firmly as in the ordinary ligating method wherein a knot is formed on a ligature wrapped around the tissue to tighten the tissue, and another knot is formed upon the first knot to prevent the first knot from loosening. This is because the knot is not sufficiently tight since it has been formed by winding one end portion around the straightened end portion.

In the method of the second type, a running noose is formed at a first end of a ligature, the first end portion of the ligature (including the noose) is wrapped around the tissue of interest, and the second end portion of the ligature is passed through the noose and pulled, causing the first end portion to tighten the tissue. Further, the first end portion of the ligature is pulled, thus tightening the noose and forming a knot on the first end portion. The second-type method, similar to the ligation performed in celiotomy, is disadvantageous because the knot formed by tightening the noose is as loose as the knot formed in the first-type method.

The conventional ligating apparatuses described above will be described, one by one, in greater detail.

The ligating apparatus disclosed in Jpn. Pat. Appln. KOKAI Publication 6-54855 designed to facilitate the forming of knots enables a surgeon to ligate by using two forceps (one being a holding forceps), both inserted into the body cavity through an opening incised in the body wall of the patient. With this apparatus, however, the surgeon cannot make a tight knot on the ligature. Furthermore, he or she needs to insert a knot pusher into the body cavity while pulling one end portion of the ligature from the body cavity. This is surgical work which is troublesome and which needs to have a ligation cartridge incorporating a knot pusher. Having such a cartridge, the ligating apparatus is difficult to manufacture.

The ligating apparatuses disclosed in U.S. Pat. Nos. 5,336,229, 5,336,231 and 5,312,423, designed to ligate tubular tissues, can be inserted into a body cavity through one opening incised in the body wall. With these apparatuses, however, a surgeon cannot form a tight knot on the ligature. The apparatus disclosed in U.S. Pat. No. 5,336,231 is difficult to operate because of its specific structure. Although the apparatuses of U.S. Pat. Nos. 5,336,229 and 5,312,423 are easy to manipulate, they are complex in structure and, hence, cannot be manufactured at low cost.

To ligate a tissue at two or more parts by using any of the conventional ligating apparatuses, a surgeon should wind threads around the apparatus, each ligature for ligating one part of the tissue. He or she must spend much time to apply a ligature to the apparatus. This inevitably lengthen the time required for the surgical operation. Several ligating apparatuses, each with a ligature already wound around it, may be used in order to shorten the operation time. The use of many ligating apparatus results in an increase in the surgery cost.

The conventional ligating apparatuses designed to ligate tubular tissues have an arm. The arm is first placed under a tubular tissue (e.g., a blood vessel) ablated from the underlying tissue and then moved up, lifting the tubular tissue. While the arm is holding the tubular tissue at a lifted position, a ligature is passed under the tubular tissue. Obviously, the arm cannot be placed under the tubular tissue unless the tubular tissue has been ablated from the underlying tissue.

The tissue of interest must be ablated from any neighboring tissues so that the surgeon may visually distinguish the tissue from the neighboring ones. The surgeon achieves the ablation by using an ablation forceps. After ablating the tissue, he or she hands the ablating forceps to an assistant and holds a ligating apparatus. When the ligating apparatus of U.S. Pat. No. 5,336,231 which has a U-shaped arm is used to ligate a tubular tissue existing on an adhesive tissue, the U-shaped arm is passed under the adhesive tissue and moved up, ablating the tubular tissue. To cut, if necessary, the tubular tissue later, the surgeon needs to lift the tissue upwards far from the adhesive tissue, but he or she cannot do so by using the U-shaped arm.

Moreover, the conventional ligating apparatus described above cannot enable the surgeon to perform surgical work (e.g., ablation), while ligating a tubular tissue. To accomplish surgical work other than ligation, the surgeon cannot help but use a forceps inserted into the body cavity through an opening incised in the body wall.

SUMMARY OF THE INVENTION

The object of the present invention is to provide a ligating apparatus with which a surgeon can perform intracorporeal ligation without using any other medical instrument and can form a tight knot on the ligature.

According to the invention there is provided a ligating apparatus which comprises: a ligature applying device having at a distal end a ligature holding section for holding a ligature; a ligature holding device movable relative to the ligature applying device, the ligature holding device having a through hole through which the ligature-applying device is to be moved, ligature holding means for holding one end of the ligature, and a ligature retaining section for retaining the ligature; ligature winding means for winding the ligature around the ligature applying device or the ligature holding device, thereby to form at least one loop to be tightened into a knot; loop releasing means for releasing the loop from the ligature applying device or the ligature holding device when the ligature applying device is pulled into the through hole of the ligature holding device; and loop tightening means for tightening the loop released from the ligature applying device or the ligature holding device, when the ligature applying device and the ligature holding device are moved relative to each other.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIG. 22 is a sectional view of the second embodiment, explaining how the free end portion of a ligature is pulled into the operation sheath, while passing through the notch cut in the main body of the cartridge;

FIG. 23 is a perspective view showing the distal end portion of a ligating apparatus according to a third embodiment of the present invention;

FIG. 24 is a sectional view of the distal end portion of the third embodiment;

FIG. 25 is a side view of the third embodiment, explaining how the forceps is operated to hold the free end portion of a ligature;

FIG. 30 is a perspective view of the ligation cartridge of a ligating apparatus according to a fourth embodiment of the present invention;

FIG. 31 shows the ligature holding section 71 of the cartridge shown in FIG. 30, which is partly fitted in the operation sheath;

FIG. 32 is a perspective view of the fourth embodiment, explaining how the loop holding section 72 of the cartridge is pushed forward, thereby mounting the looped portion of a ligature on the forceps;

FIG. 33A is a perspective view of the ligation cartridge of a ligating apparatus according to a fifth embodiment of the present invention;

FIG. 33B is a sectional view showing the upper half of the cartridge shown in FIG. 33A;

FIG. 38 is a perspective view of the distal end portion of the fifth embodiment, explaining how the looped portion of the ligature is tightened;

FIGS. 39A and 39B are perspective views of the distal end portion of the fifth embodiment, explaining how to cut the unnecessary portions of the ligature;

FIG. 45 is a diagram explaining how to tighten the first loop to suture the tissue;

FIG. 46 is a diagram explaining how to pull the free end portion of the ligature into the second loop of the ligature;

FIG. 47 is a diagram explaining how to tighten the second loop to suture the tissue;

FIG. 48 is a perspective view of the ligation cartridge which is one component of a ligating apparatus according to a seventh embodiment of the present invention;

FIG. 49 is a side view of the ligating apparatus according to the seventh embodiment;

FIG. 57A is a front view, taken along line 57A—57A in FIG. 57B;

FIG. 57B is a side view of the ligation cartridge;

FIG. 58A is a sectional view of the ligation cartridge, taken along line 58A—58A in FIG. 58B;

FIG. 58B is a bottom view of the ligation cartridge;

FIGS. 59A and 59B, FIGS. 60A and 60B and FIGS. 61A and 61B, FIGS. 62A–62C, FIG. 63 and FIG. 64 are diagrams, explaining how the apparatus shown in FIG. 50 is operated to ligate a tissue;

FIG. 67A to 67D are exploded views of the cartridge which is one component of a ligating apparatus according to a ninth embodiment;

FIG. 68 is a front view of the ninth embodiment, as seen in the direction of arrow F shown in FIG. 67D;

FIG. 71 is a diagram explaining how to operate the nine embodiment to ligate a tissue present in a body cavity;

FIGS. 72A to 72C are exploded views of a ligating apparatus according to a tenth embodiment of the present invention;

FIG. 73 is a side view of the tenth embodiment, explaining how to operate this embodiment to ligate a tissue;

FIG. 74 is a perspective view of the distal end portion of a ligating apparatus according to an eleventh embodiment of the invention;

FIGS. 75A and 75B are diagrams explaining how a ligature is wound around the ligature holding section of the eleventh embodiment;

FIGS. 92 to 97 are perspective views of the distal end portion of the sixteenth embodiment, explaining how this embodiment is operated to suture a tissue;

FIGS. 100A to 100C are exploded views of a ligating apparatus according to an eighteenth embodiment of the present invention;

FIG. 102A is a front view of the cartridge main body of a first modification of the eighth embodiment;

FIG. 102B is a sectional view, taken along line 102B—102B in FIG. 102C; and

FIG. 102C is a bottom view of the distal portion of the cartridge main body illustrated in FIG. 102A.

DETAILED DESCRIPTION OF THE PREFERRED EMBODIMENTS

Embodiments of the present invention will be described, with reference to the accompanying drawings.

A ligating apparatus according to the first embodiment will be described with reference to FIGS. 1 to 9B. The apparatus comprises a ligation cartridge 1 shown in FIG. 1, an operation sheath 30 shown in FIG. 6, and a forceps 35 shown in FIG. 7.

Figure 1:
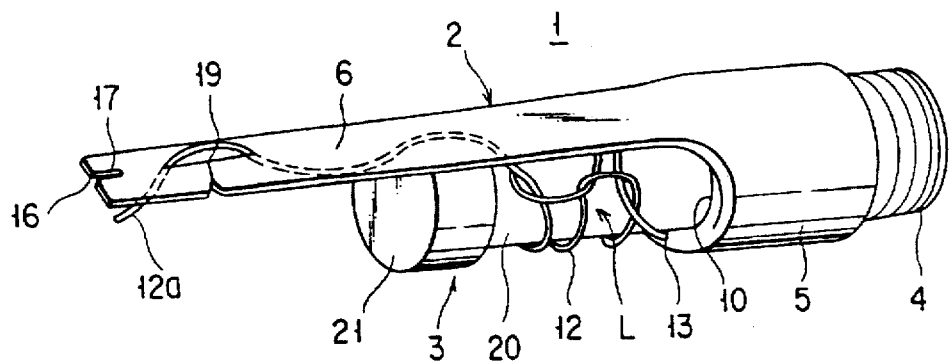
FIG. 1 is a perspective view of the ligation cartridge which is a component of a ligating apparatus according to a first embodiment of the invention.

As shown in FIG. 1, the ligation cartridge 1 comprises a main body 2 and a loop holder 3 removably set in the main body 2. As seen from FIGS. 2A and 2B, the main body 2 of the cartridge 1 comprises a hollow cylindrical base 4, a hollow cylindrical loop holding section 5 and a plate-like ligature holding section 6. The base 4 can be connected, in screw engagement, to the distal end of the operation sheath 30. The loop holding section 5 is connected to the distal end of the base 4. The ligature holding section 6 extends from the distal end of the section 5, substantially parallel to the axis of the section 5. The section 6 is so shaped as to be inserted into trocars designed for use in endoscopic operations.

The base 4 has a hole. So does the loop holding section 5. The holes are coaxial and constitute a through hole 10, through which the forceps 35 (FIG. 7) can be inserted for use in endoscopic operations. Needless to say, the through hole 10 has a diameter greater than those of the forceps.

Figure 2A:
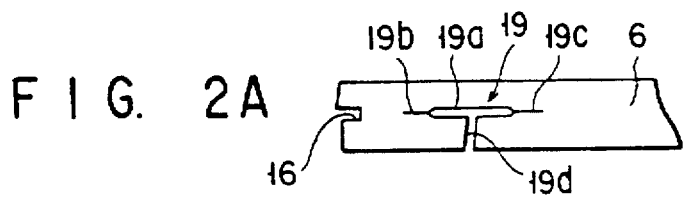
FIG. 2A is a plan view showing the distal end portion of the ligature holding section of the cartridge shown in FIG. 1.
Figure 2B:
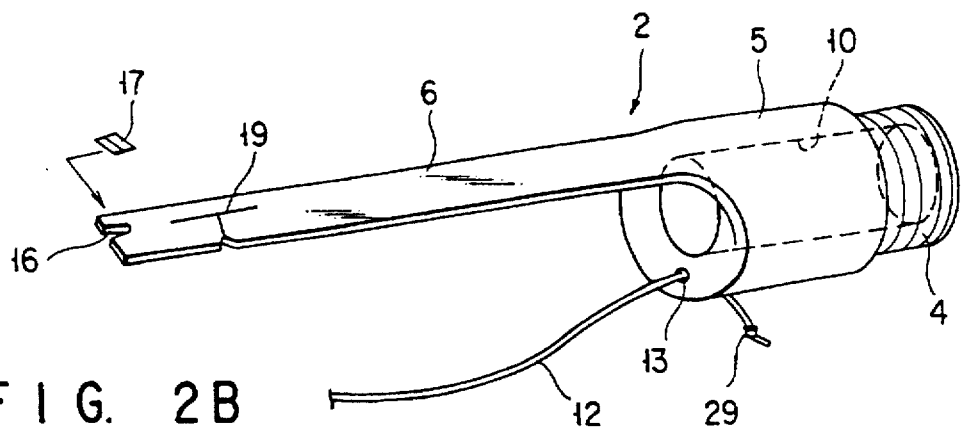
FIG. 2B is a perspective view of the main body of the cartridge.

The loop holding section 5 has a ligature holder 13. As illustrated in FIG. 2D, the holder 13 consists of a ligature guiding hole 13a and a ligature holding hole 13b. The ligature guiding hole 13a extends from the outer circumferential surface of the section 5 to the distal end thereof. The ligature holding hole 13b is a counter bore made in the outer circumferential surface of the section 5 and communicating with the ligature guiding hole 13a. A ligature 12 is passed through the ligature guiding hole 13a. A knot 29 is formed on that end portion of the ligature 12 which projects from the outer circumferential surface of the section 5. The knot 29 abuts on the section 5, in the ligature holding hole 13b when the ligature 12 is pulled forward from the distal end of the section 5. The ligature 12 can be of any type designed for surgical use.

The ligature holding section 6 is longer than the clamping section of the forceps 35. Also the section 6 is much longer than the loop holder 3. It is appropriately elastic. It has a slit 19 in the distal end portion. The slit 19 generally extends in the axial direction of the section 6 and is broad enough to allow the passage of the ligature 12. More precisely, the slit 19 consists of four slits 19a, 19b, 19c and 19d as is shown in FIG. 2A. The slit 19a extends in the axial direction of the section 6. The slit 19d extends from the slit 19a at right angles thereto and opens at the lateral edge of the section 6. The slits 19b and 19c extend from the ends of the slit 19a, respectively, in the axial direction of the section 6. The slits 19b and 19c are narrow enough to catch and hold the ligature 12. By contrast, the slits 19a and 19d are broad enough to allow easy passage of the ligature 12.

Figure 2C:
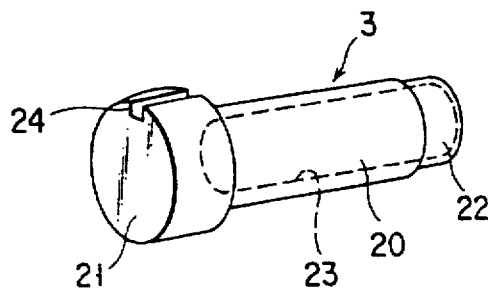
FIG. 2C is a perspective view of the loop holder which is a component of the cartridge.
Figure 2D:
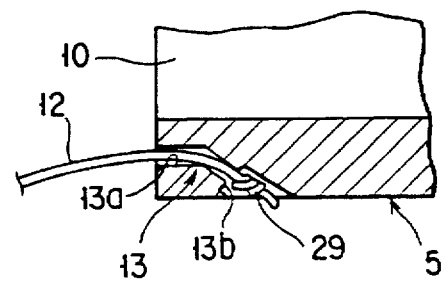
FIG. 2D is a sectional view showing a part of the loop holding section of the main body of the cartridge.

As illustrated in FIG. 2C, the loop holder 3 is a columnar member, comprised of a ligature holding cylinder 20, a loop stopping cylinder 21, and a base cylinders 22. The cylinder 20 and 22 are hollow ones, and the cylinder 21 is a solid one. The ligature holding cylinder 20 has an outer diameter larger than the outer diameter of the base cylinder 22 and smaller than the diameter of the loop stopping cylinder 21. Hence, the loop holder 3 is generally a cylinder having two stepped portions. The cylinders 20 and 22 have holes 23 which are coaxial and continuous. The holes 23 are large, allow the passage of the distal end portion of the forceps 35. The hole 23 in the cylinder 20 has a bottom, whereas the hole 23 in the base cylinder 22 is a through hole.

The loop stopping cylinder 21 has its circumferential surface contact the inner surface of the ligature holding section 6 when the base cylinder 22 is fitted into the through hole 10 of the main body 2 of the cartridge 1, thereby coupling the loop holder 3 with the main body 2. Once the main body 2 and the loop holder 3 are coupled together, the end of the loop stopping cylinder 21, the end of loop holding section 5, the outer circumferential surface of the cylinder 21, and the inner surface of the ligature holding section 6 define a loop holding space. The loop stopping cylinder 21 has a ligature guiding groove 24 in its circumferential surface. The groove 24 is wider than the ligature 12 is thick. The groove 24 is located at the inner surface of the section 6 as long as the loop holder 3 remains coupled with the main body 2 of the ligation cartridge 1.

Referring back to FIG. 1, that end portion of the ligature 12 which projects from the distal end of the loop holding section 5 is wound around the ligature holding cylinder 20 a few times, and the other end portion of the ligature 12 is held in the ligature holder 13 of the loop holding section 5. The ligature 12 therefore comes to have a looped portion L formed on the ligature holding cylinder 20. The looped portion L is held in the above-mentioned loop holding space as long as the loop holder 3 remains coupled with the main body 2.

The free end portion 12a of the ligature 12, extending forward from the looped portion L, is guided from the loop holding space through the ligature guiding groove 24 of the loop stopping cylinder 21. The portion 12a of the ligature 12 is first passed through the slit 19a from under the ligature holding section 6 and then held in the narrow slit 19c. That end portion of the ligature, which extend from the slit 19b, is passed downwards through the slit 19a and held in the narrow slit 19b. As a result, the free end portion 12a of the ligature 12 extends downwards from the narrow slit 19b. The free end portion 12a is longer than the distance between the inner surface of the ligature holding section 6 and the distal end of the forceps 35 (FIG. 7) inserted in the through hole 10 of the main body 2.

Figure 3:
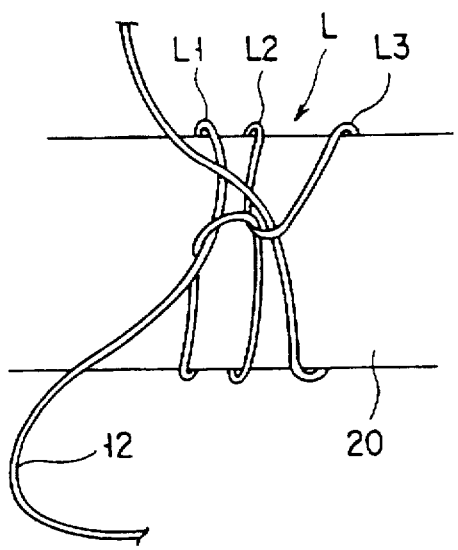
FIG. 3 shows the looped portion of a ligature wound around the ligature holding cylinder of the loop holder.

The looped portion L of the ligature 12 may assume whichever shape, provided that it will finally form a tight knot. In the present embodiment, the looped portion L has such a specific shape as is shown in FIG. 3. How the looped portion L is formed in this shape will be explained with reference to FIGS. 4A to 4C.

Figure 4A:
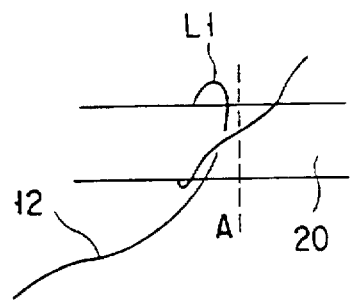
FIGS. 4A to 4C are diagrams explaining how to form the looped portion of the ligature.
Figure 4B:
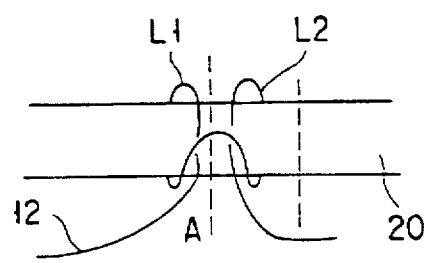
Figure 4C:
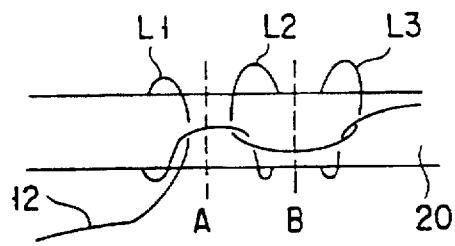

At first, the ligature 12 is wound once around the ligature holding cylinder 20, forming a first loop $L_1$, as shown in FIG. 4A. As shown in FIG. 4B, the ligature 12 is further wound once around the cylinder 20, forming a second loop $L_2$ which is symmetrical to the first loop $L_1$ with respect to a plane A perpendicular to the axis of the cylinder 20. Then, as shown in FIG. 4C, the ligature 12 is wound around the cylinder 20 once again, forming a third loop $L_3$ which is symmetrical to the second loop $L_2$ with respect to a plane B perpendicular to the axis of the cylinder 20. The first loop $L_1$ and the third loop $L_3$ are wound in the same direction, and the second $L_2$ in the opposite direction. Thus, the looped portion L having the shape shown in FIG. 3 consists of three loops $L_1$ to $L_3$.

Figure 5A:
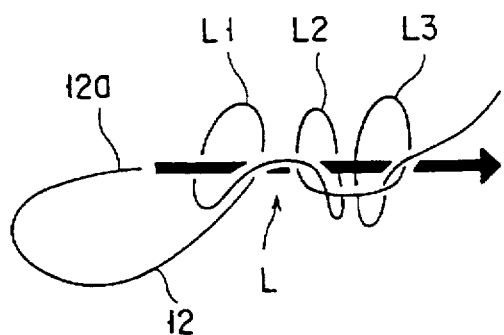
FIG. 5A and 5B are diagrams explaining how the looped portion of the ligature are tightened to form knots.
Figure 5B:
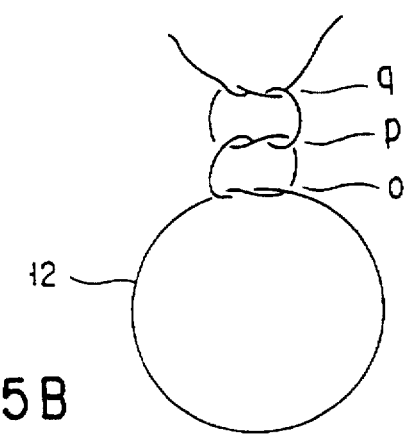

When the free end portion 12a of the ligature 12 is passed through the three loops $L_1$ to $L_3$ and pulled in the direction of the arrow shown in FIG. 5A, the ligature 12 form one loop and a triple knot as shown in FIG. 5B. The triple knot consists of three knots o, p and q, which form a square knot. The triple knot is firm and tight since it consists of the knots o, p and q made by winding the ligature 12 three times, alternately in one direction and the other, around the ligature holding cylinder 20.

Figure 6:
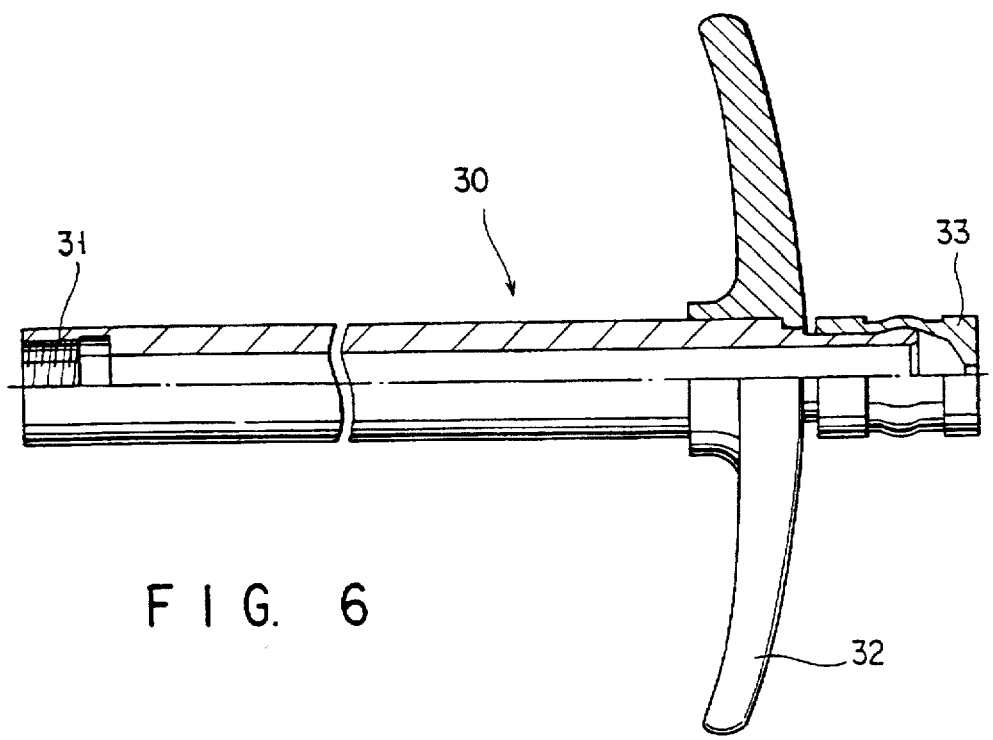
FIG. 6 is a partly sectional view of the operation sheath which is a component of the first embodiment of the invention.
Figure 7:
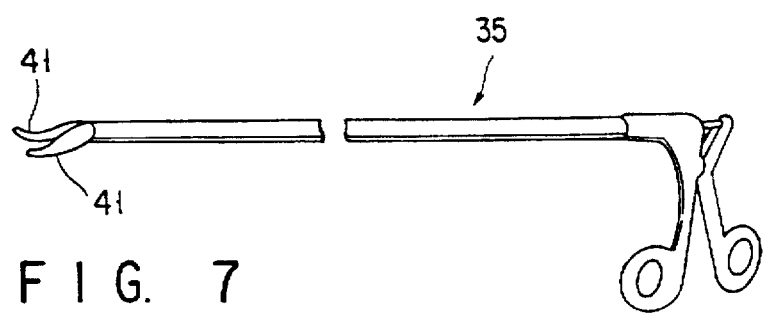
FIG. 7 is a perspective view of the forceps which is a component of the first embodiment.
Figure 8:
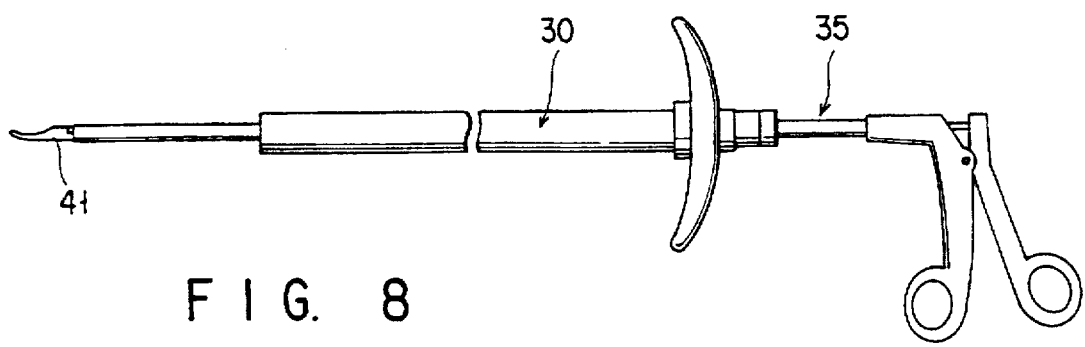
FIG. 8 is a diagram illustrating the operation sheath and the forceps passed through the sheath.

FIG. 6 shows the operation sheath 30 which is generally a hollow cylinder. The sheath 30 is thin enough to pass through trocars and the like. Its inner diameter is large enough to allow the passage of the forceps 35 shown in FIG. 7, which is designed for use in endoscopic surgical operations. The sheath 30 has a female screw 31 cut in the inner circumferential surface of the distal end portion. It is in this female screw 31 that the male screw on the base section 4 of the main body 2 can be set in engagement. A rubber plug 33 is fitted in the proximal end of the operation sheath 30, for providing airtight sheath between the inner circumferential surface of the sheath 30 and the outer circumferential surface of the forceps 35 inserted in the sheath 30 as shown in FIG. 8. As can be understood from FIG. 8, the operation sheath 30 is shorter than the forceps 35, and the distal end portion of the forceps 35 can protrude from the distal end of the sheath 30. The sheath 30 has such a length that the forceps 35 projects from the loop holding section 5, by a distance longer than the ligature 12, when the cartridge 1 is coupled to the distal end of the sheath 30 and the forceps 35 is inserted into the sheath 30.

How a surgeon use the ligation cartridge 1 to ligate a tissue preset in a patient's body cavity will be explained.

Figure 9A:
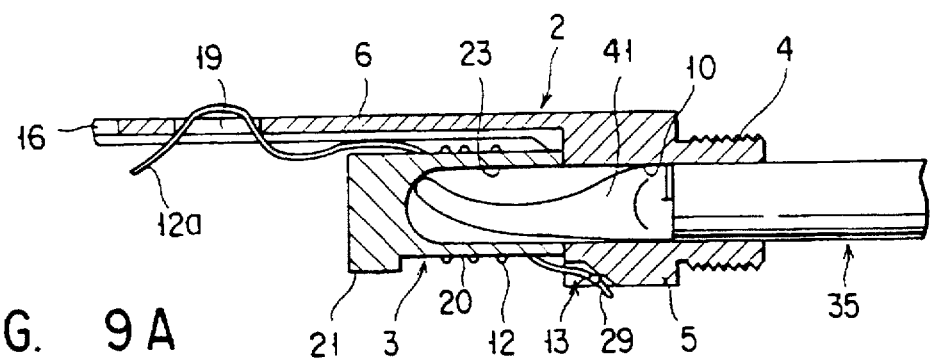
FIG. 9A is a sectional view showing the forceps and the cartridge mounted on the distal end portion of the forceps.
Figure 9B:
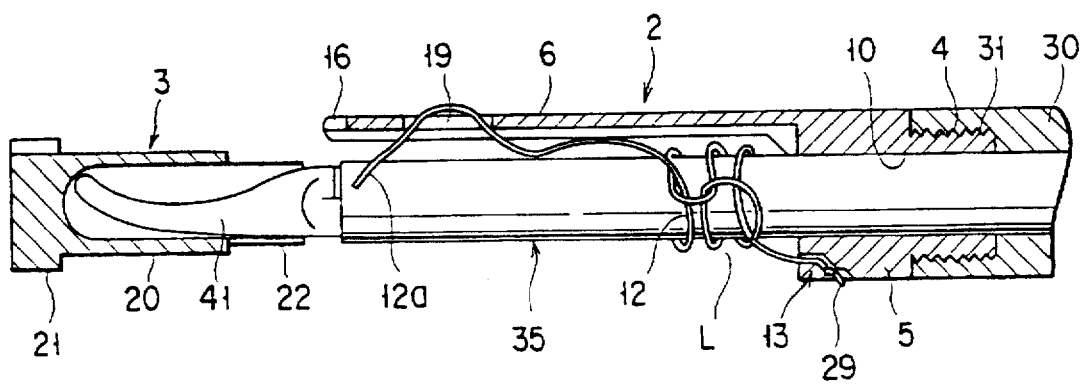
FIG. 9B is sectional view showing the cartridge coupled to the sheath and the forceps partly pushed from the distal end of the cartridge.
Figure 10:
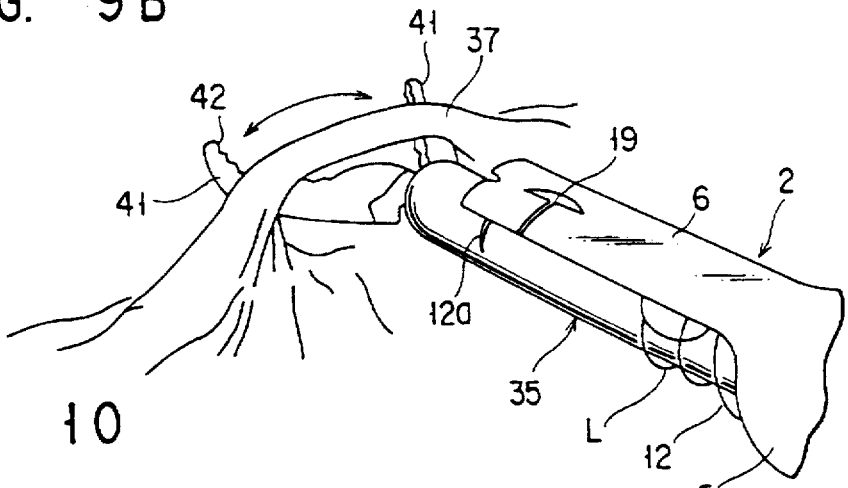
FIG. 10 is a perspective view showing the forceps and a tubular tissue being ablated from the neighboring tissue by means of the forceps.

The forceps 35 will be described in detail. (The forceps 35 may be replaced by any other type in accordance with the size, shape and position of the tissue.) The forceps 35 is generally known as Kelly forceps. As shown in FIG. 10 which is an enlarged view, the forceps 35 has a pair of tongs 41 at the distal end, each having teeth 42 on the inner edge. The forceps 35 is often used to ablate tubular tissues such as blood vessels. To ligate a tissue, a surgeon inserts the Kelly forceps 35 into the operation sheath 30 from the distal end thereof. He or she then pushes the forceps 35 until the distal end portion of the forceps 35 projects from the distal end of the sheath 30, as is illustrated in FIG. 8. Next, as shown in FIG. 9A, the surgeon inserts the distal end portion of the forceps 35 into the cartridge 1 which is a combination of the main body 2 and the loop holder 3. To be more specific, the distal end portion of the forceps 35 is inserted into the hole 23 of the holder 3 fitted in the through hole 10 of the ligation cartridge 2. Finally the distal end of the Kelly forceps 35 abuts on the bottom of the hole 23. As the surgeon pushes the forceps 35 forwards, the loop holder 3 is moved from the distal end of the main body 2 as shown in FIG. 9B. As a result of this, the looped portion L of the ligature 12 slips from the loop holder 3, maintaining its shape. The looped portion L is mounted on the Kelly forceps 35, which is now positioned below the ligature holding section 6 of the main body 2. Thereafter, the surgeon removes the loop holder 3 from the Kelly forceps 35 and rotates the main body 2 mounted on the Kelly forceps 35, setting the base section 4 in the female screw 31 cut in the distal end of the operation sheath 30. Then, the operation sheath 30 with the main body 2 attached to the sheath 30 and the Kelly forceps 35 inserted in the sheath 30 are inserted into the body cavity through a trocar or the like fitted in an opening incised in the patient's body wall.

Figure 11:
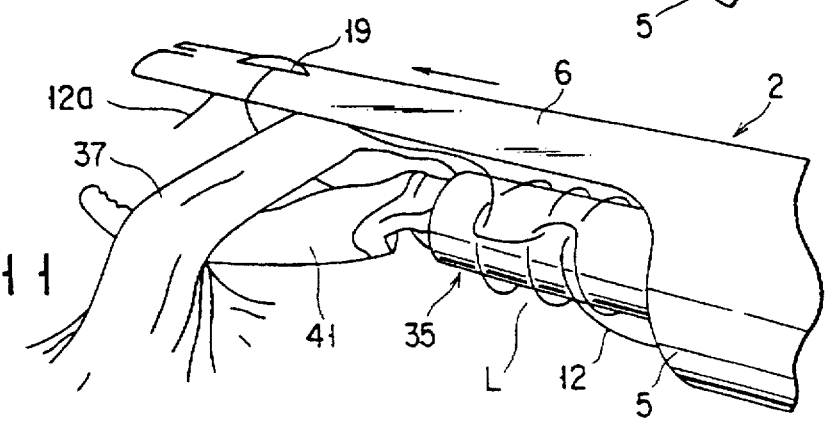
FIG. 11 is a perspective view showing the distal end portion of the sheath, pushed forward from the position shown in FIG. 10.
Figure 12A:
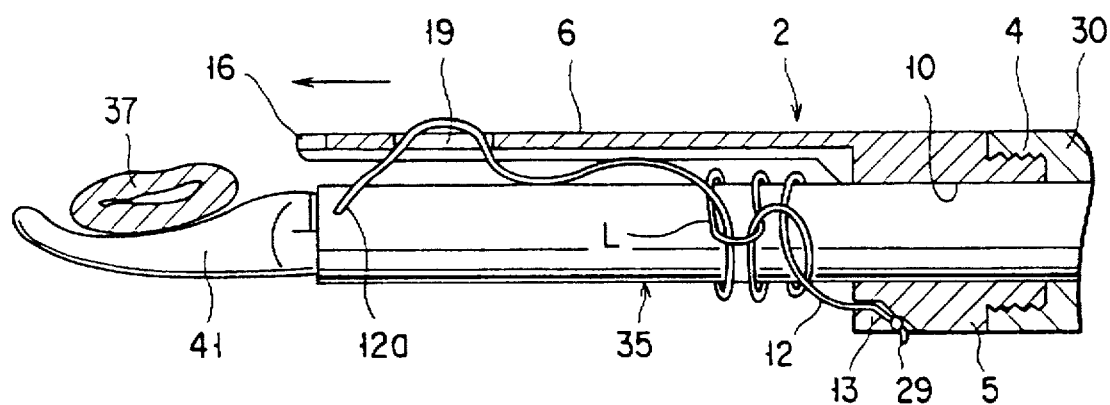
FIGS. 12A to 12C are sectional views explaining how the free end portion of the ligature is applied to the tubular tissue.
Figure 12B:
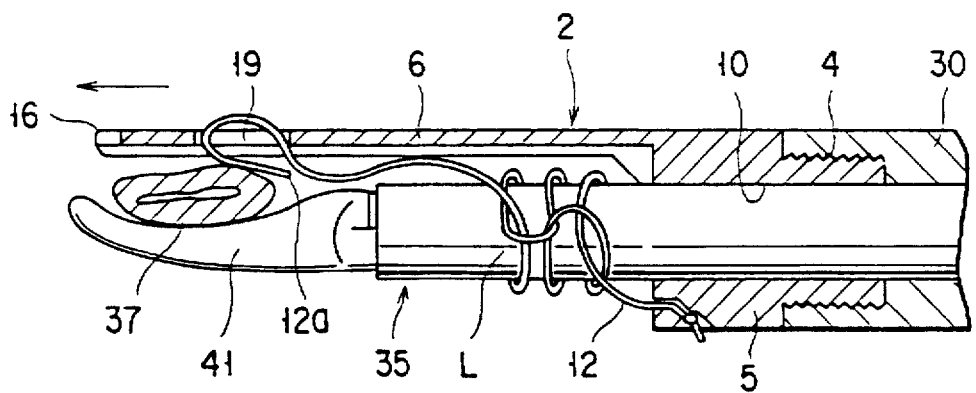
Figure 12C:
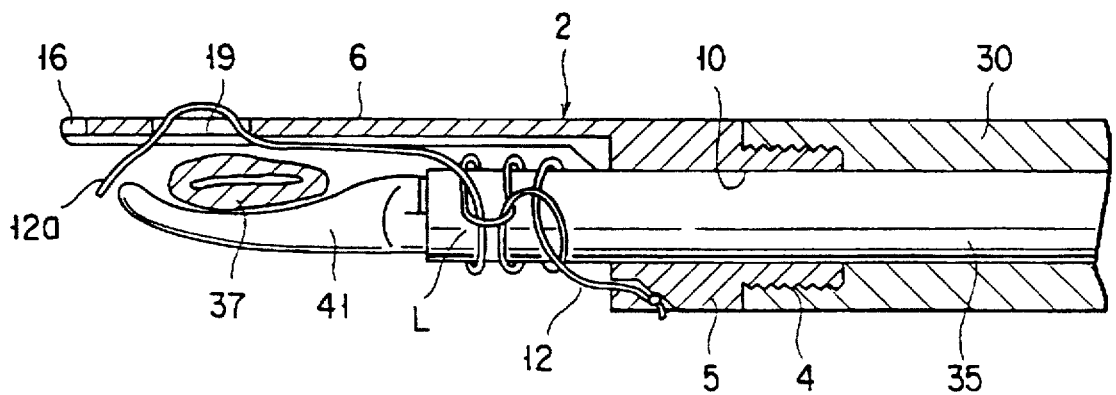

In preparation for ligating a tubular tissue 37 (e.g., a blood vessel), the surgeon first ablates the tissue 37 from the neighboring tissue, by using the Kelly forceps 35. More correctly, the surgeon abuts the distal end of the forceps 35 on the junction between the tubular tissue 37 the neighboring tissue. The surgeon and opens the tongs 41 in this condition, thereby ablating the vessel 37 from the neighboring tissue, without cutting the tubular tissue 37. This is the method of ablation, employed in most surgical operations. Upon completion of the ablation, the surgeon moves the operation sheath 30 forward, while maintaining the tongs 41 open. He or she keeps moving the sheath 30 until the distal end of the ligature holding section 6 of the main body 2 reaches a position in front of the tubular tissue 37 as shown in FIG. 11. Before the surgeon moves the sheath 30 forward, the free end portion 12a of the ligature 12, caught in the slit 19, extends downwards from the section 6 as shown in FIG. 12A. As the sheath 30 is moved forward, this portion 12a of the ligature 12 contacts the tubular tissue 37 and is bent backwards as illustrated in FIG. 12B. When the portion 12a passes completely over the tissue 37 as the sheath 30 is further moved forward, it again extends downwards due to its elasticity as shown in FIG. 12C. The free end portion 12a of the ligature 12 is long enough to be held easily between the tongs 41 of the Kelly forceps 35.

Figure 13A:
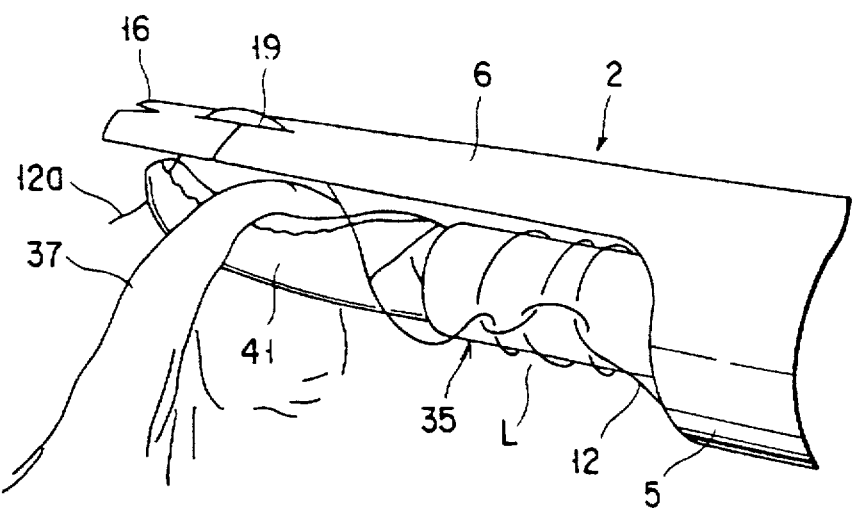
FIG. 13A is a perspective view illustrating the tongs of the forceps, clamping the free end portion of the ligature at a position in front of the tissue.
Figure 13B:
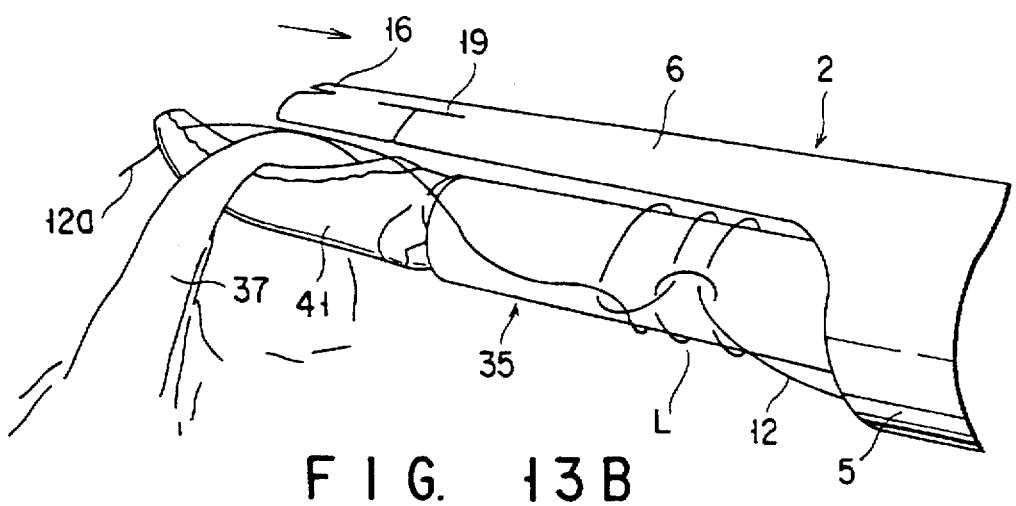
FIG. 13B is a perspective view showing the sheath pulled backwards, releasing the distal end portion of the suture from the ligature holding section of the cartridge.
Figure 14:
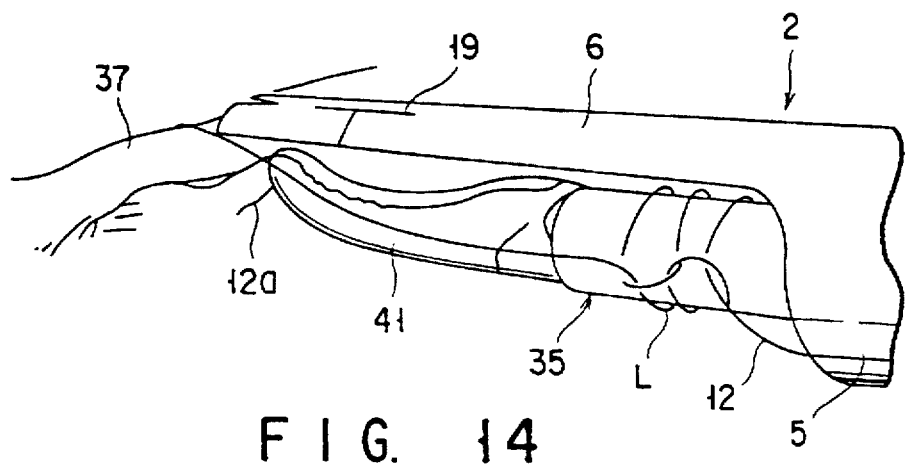
FIG. 14 a perspective view showing the free end portion of the ligature, passed under the tubular tissue.

Next, the surgeon pulls the operation sheath 30 backwards until the free end portion 12a of the ligature 12, which extends downwards, is caught between the tongs 41 of the Kelly forceps 35. The surgeon then closes the tongs 41, which clamps the portion 12a of the ligature 12 as illustrated in FIG. 13A. The surgeon pulls the sheath 30 further backwards, whereby the portion 12a of the ligature 12 is released from the slit 19 of the ligature holding section 6 as is shown in FIG. 13B. Then, the surgeon pulls the Kelly forceps 35 backwards, moving the closed tongs 41 from under the tubular tissue 37 as is illustrated in FIG. 14.

Figure 19A:
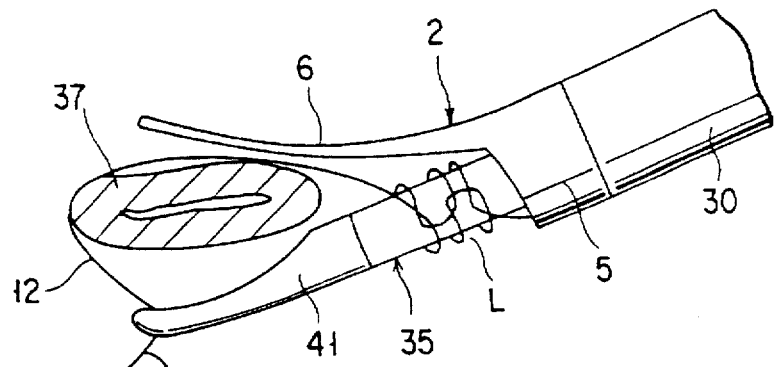
FIG. 19A is a diagram explaining how the first embodiment is operated in a specific condition.
Figure 19B:
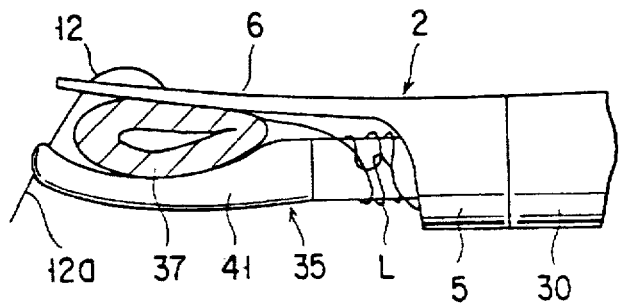
FIG. 19B is a diagram explaining how the first embodiment is operated in another condition.

The tubular tissue 37 may be so thick that the ligature 12 cannot be wrapped around the tissue 37 unless the looped portion L of the ligature 12 is moved toward the tongs 41. To move the looped portion L toward the tongs 41, the surgeon needs only to push the sheath 30 forward. Once the surgeon pushes sheath 30 so, he or she can pull the tongs 41 holding the distal end of the ligature 12, successfully wrapping the ligature 12 around the tubular tissue 37. The sheath 30 and, hence, the ligature holding section 6 may be excessively pushed forwards, and the tubular tissue 37 may enter the gap between the section 6 and the tongs 14. Even in this case, the ligature 12 can be passed under the tissue 37 by pulling the forceps 35. This is because the section 6 is bent upwards as shown in FIG. 19A, allowing the tongs 41 to move backwards from under the tubular tissue 37. The ligature holding section 6 may be bent as shown in FIG. 19B as the free end portion 12a of the ligature 12, still held in the slit 19 of the section 6, again extends downwards due to its elasticity as the surgeon moves the sheath 30 forward.

Figure 15A:
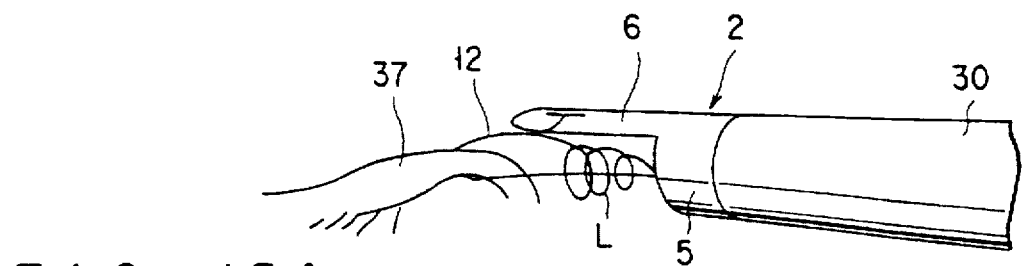
FIG. 15A and 15B are diagrams showing the free end portion of the ligature, being passed through the looped portion of the ligature.
Figure 15B:
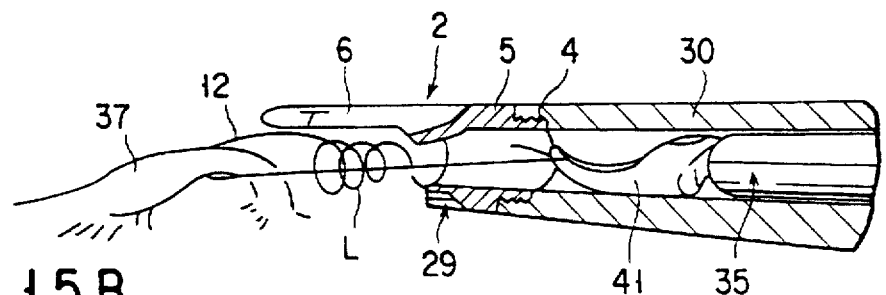
Figure 16A:
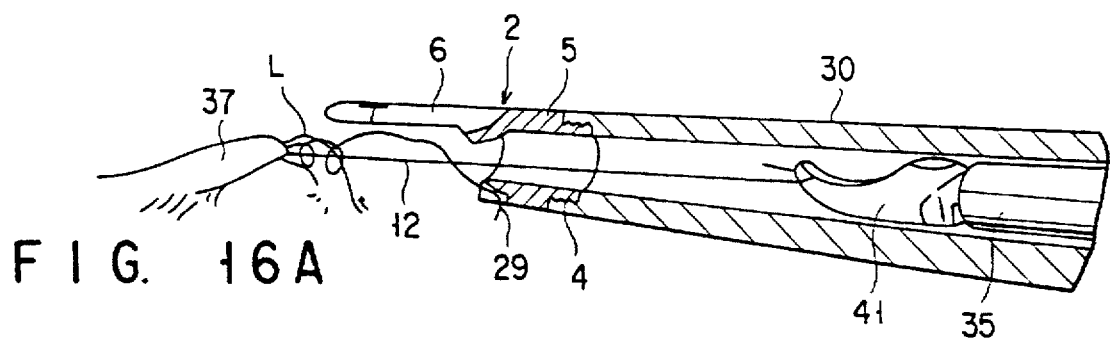
FIGS. 16A to 16C are sectional views of the cartridge and the sheath, explaining how to ligate the tissue with the ligature.
Figure 16B:
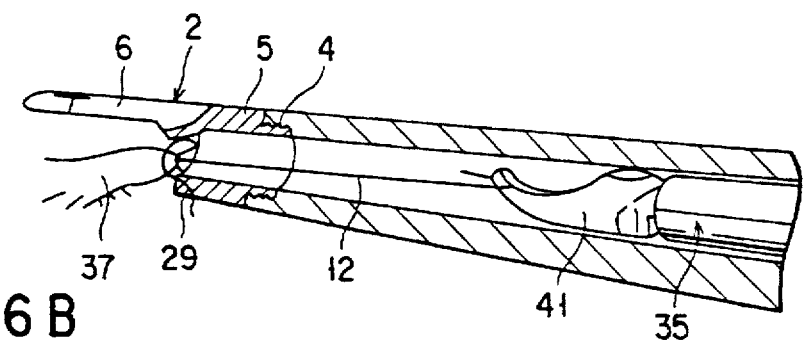
Figure 16C:
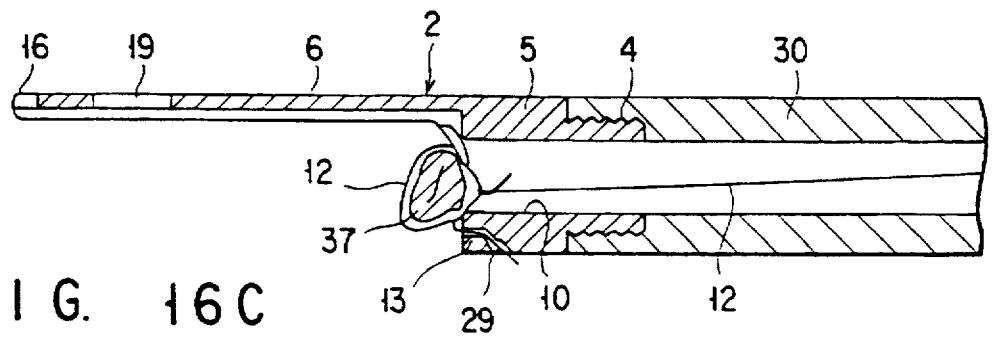

After the suture 12 has been passed under the tubular tissue 37, the surgeon pulls the Kelly forceps 35 into the operation sheath 30. As a result, the looped portion L of the ligature 12 slips from the forceps 35 as shown in FIGS. 15A and 15B. At the same time, the closed tongs 41 is pulled into the sheath 30, passing through the looped portion L of the ligature 12, as is illustrated in FIGS. 15A and 15B. Clamped between the tongs 41, the free end portion 12a of the ligature 12 is passed through the looped portion L of the ligature 12. As the forceps 35 and, hence, the tongs 41 are further pulled into the operation sheath 30, the looped portion L of the ligature 12 is tightened as shown in FIG. 16A. More precisely, the first loop $L_1$ is tightened, forming a first knot. The tubular tissue 37 is thereby tightened to some extent. Not to apply an excessive tension on the tissue 37 at this time, the surgeon may first push the sheath 30 forward to abut the loop holding section 5 on the tissue 37 and then pull the forceps 35 deeper into the sheath 30, as is illustrated in FIGS. 16B and 16C.

Figure 17:
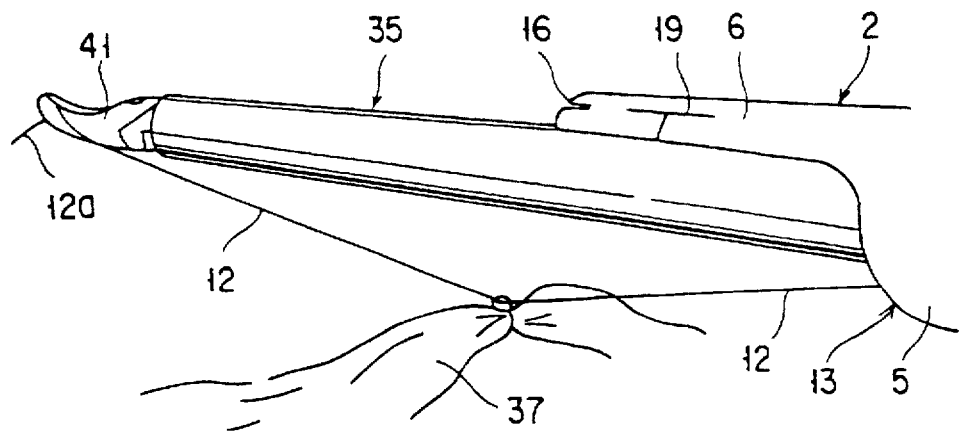
FIG. 17 is a perspective view explaining how the looped portion of the ligature is tightened to form knots, by moving the sheath and the forceps in opposite directions.

After tightening the tissue 37 to some extent, the surgeon pulls the operation sheath 30 (and, hence, the main body 2 of the cartridge 1), while pushing the Kelly forceps 35 forward with respect to the sheath 30, as is illustrated in FIG. 17. The free end portion 12a of the ligature 12 and the other end portion thereof are thereby moved in the opposite direction because they are held the tongs 41 and the ligature holder 13 of the loop holding section 5, respectively. As a result, the second loop $L_2$ and the third loop $L_3$ are tightened, forming the second and third knots.

The first embodiment enables surgeons to carry out ligation in a specific method, as will be explained with reference to FIGS. 18A to 18D.

Figure 18A:
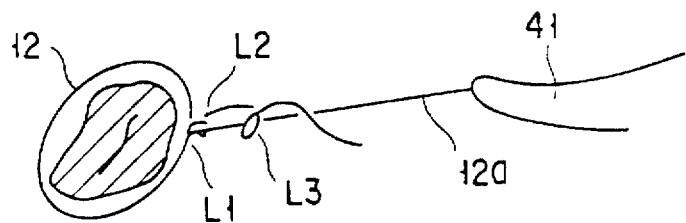
FIGS. 18A to 18D are diagrams explaining the process of ligating a tubular tissue as shown in FIG. 17.
Figure 18B:
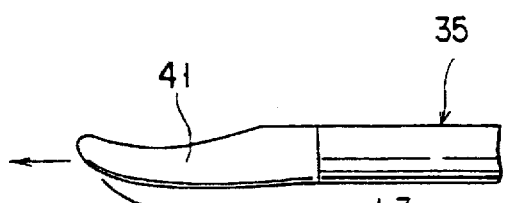
Figure 18C:
Figure 18D:
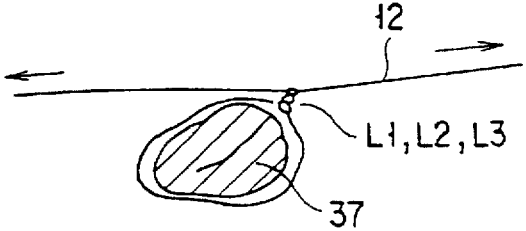

FIG. 18A shows a condition similar to the one illustrated in FIG. 16A. In this condition, the first loop $L_1$ is firmly tightened as the free end portion 12a of the ligature 12 is pulled, and the second loop $L_2$ is tightened but not so strongly. FIG. 18B shows a condition similar to the one illustrated in FIG. 17. As the surgeon pushes the Kelly forceps 35, pulling the free end portion 12a of the ligature 12, the third loop $L_3$ rotates as shown in FIG. 18C, entangling the ligature 12. As the portion 12a of the ligature 12 is further pulled, the second loop $L_2$ and the third loop $L_3$ form second and third knots as shown in FIG. 18D. The second and third knots have been made, by entangling two portions of the ligature 12 with each other, not by wrapping one portion twice around a straight portion. Thus, these knots are tight and firm.

Upon completion of the ligation, the surgeon operates the blade 17 attached to the distal end of the ligature holding section 6, cutting those portions of the ligature 12 which extend from the third knot. He or she then pulls the operation sheath 30 and the Kelly forceps 35 from the body cavity through the trocar. One portion of the ligature 12, cut from the third knot, is held between the tongs 41, whereas the other portion cut from the third knot is fastened to the ligature holder 13. Both cut portions of the ligature 12 are therefore removed from the body cavity as the surgeon pulls the sheath 30 and the forceps 35 out of the body cavity. To ligate another part of the tubular tissue 37 or another tissue present in the body cavity, the surgeon only needs to disconnect the cartridge 1 from the operation sheath 30 and couples a new cartridge thereto.

Having the forceps 35, the ligating apparatus according to the first embodiment enables surgeons to conduct intracorporeal ligation, easily forming tight knots on a ligature, without using any other medical instruments. In addition, the ligature 12 would not move from a desired position or the looped portion L would not slip from the forceps 35 when the cartridge 1 is inserted into the body cavity through the trocar. This is because the ligature 12 is held at both ends to the main body 2 of the ligation cartridge 1. Furthermore, the loop holder 3 would not deform the looped portion L of the ligature 12 when the ligation cartridge 1 is mounted on the forceps 35.

Using the ligation cartridge 1, a surgeon can ablate the tubular tissue 37 (e.g., a blood vessel), pass the ligature 12 under the tissue 37, ligate the tissue 37, cut both end portions of the ligature 12 from the knot last formed on the ligature 12, and remove both end portions of the ligature 12 from the body cavity—by manipulating only one forceps 35. It is therefore unnecessary for the surgeon to incise openings in the body wall, through which to insert other instruments into the body cavity. The ligating apparatus according to the first embodiment helps the surgeon to accomplish a low-invasive ligation. Moreover, the apparatus facilitates ligation since the ligature 12 can be wrapped around a tissue and knots can be formed on the ligature and tightened sufficiently, merely by moving the operation sheath 30 back and forth with respect to the forceps 35. Still further, the surgeon can quickly start the next ligation since he or she only needs to disconnect the used cartridge 1 from the operation sheath 30 and connect a new cartridge thereto.

In the ligation which the surgeon can perform by using the cartridge 1 of the first embodiment, both portions of the ligature 12 are pulled in the opposite directions. This renders the knots formed on the ligature adequately tight. The tissue of interest can be tied firmly and strongly, because the free end portion 12a of the ligature 12 is first wrapped around the tissue, then passed through three loops $L_1$ to $L_3$ of the ligature 12 and finally pulled hard.

The main body 2 of the ligation cartridge 1 may be made of transparent material, in which case the surgeon can see well the ligature 12, the tubular tissue 37 and the tongs 41. The surgeon can easily determine the position the free end of the ligature 12 assumes with respect to the tongs 41 and easily clamp the free end of the ligature 12, and can observe how the tubular tissue 37 is being ligated as shown in FIG. 16C.

The advantages of the first embodiment, described above, will be more clearly understood when the embodiment is compared with the ligating apparatus disclosed in U.S. Pat. No. 5,312,423.

The apparatus disclosed in U.S. Pat. No. 5,312,423 comprises a tubular main body, a tubular loop holding section, and a ligature pulling member. The loop holding section is provided in the main body, for holding a looped portion of a ligature. The ligature pulling member is provided in the loop holding section and can move back and forth, for pulling a ligature into the loop holding section. An elastic arm is connected to the distal end of the main body. The arm has a space and a ligature holding section. The arm can catch a tissue, such as a blood vessel, in the space. The ligature holding section extends upwards to the axis of the ligature pulling member.

The middle portion of a ligature is wound around the loop holding member. A first end of the ligature is held to a part of the main body, whereas the second end of the ligature is passed under the tissue and held to the thread holding section of the arm. A tag is connected to the second end of the ligature. The tag abuts on the ligature pulling member when the member is pulled into the loop holding section. The ligature pulling member is coupled with the loop holding section when it is pulled into the section for some distance. Once coupled with the loop holding section, the ligature pulling member is pulled into the main body, together with the loop holding section. As the ligature pulling member and the loop holding section are pulled into the main body, the junction between the main body and the loop holding section is broken.

A surgeon may use the ligating apparatus disclosed in U.S. Pat. No. 5,312,423 in the following manner, in order to ligate, for example, a blood vessel ablated from the neighboring tissue.

At first, the surgeon places the arm under the blood vessel, catching the same in the space the arm has. He or she then pushes the ligature pulling member forward, over the blood vessel. The moment the member reaches the ligature holding section of the arm, the surgeon pulls the member backwards, until the tag abuts on the distal end of the member. The ligature is thereby released from the ligature holding section.

The surgeon further pulls the ligature pulling member into the main body, coupling the same with the loop holding section. At this time, the junction between the main body and the loop holding section is broken. The loop holding section is pulled into the main body, along with the ligature pulling member. As the loop holding section is pulled into the main body, the looped portion of the ligature abuts on the distal end of the main body. The looped portion falls off the loop holding section onto the ligature which the ligature pulling member has pulled into the loop holding section. In other words, the looped portion is released in front of the main body, with the second end of the ligature passing through the looped portion. As the ligature pulling member and the loop holding section are further pulled into the main body, the looped portion of the ligature, wound around the arm, is closed, forming knots. When the member is further pulled into the main body, pulling the ligature thereinto, the arm is elastically bent, releasing the ligature. The knots on the ligature released abut at the notch made in the distal end of the main body, and the ligature wrapped around the blood vessel is pulled, passing through the knots. As a result, the blood vessel is ligated.

The ligating apparatus disclosed in U.S. Pat. No. 5,312,423 is disadvantageous in the following respects:

(1) Since the ligature is pulled at one end to ligate the tissue, a tension is applied on the tissue in one direction.

(2) Knots are first made and the ligature is then pulled through the knots, thereby to ligate the tissue, whereas the ligature is first pulled to ligate the tissue to some extent and tight knots are formed, thereby to ligate the tissue completely, in the ordinary surgical operation. Therefore, the knots may not be sufficiently tightened in some cases.

(3) A plurality of identical ligating apparatuses must be used to ligate the tissue at two or more parts thereof.

(4) With the ligating apparatus it impossible to ablate the tissue of interest from the neighboring tissues. The surgeon needs to use a forceps to ablate the tissue, pull the forceps from the body cavity, and insert the ligating apparatus into the body cavity.

(5) The arm for transferring the ligature to the ligature pulling member may prevent the member from smoothly moving forward since it is located in front of the ligature pulling member.

The ligating apparatus according to the first embodiment of the invention is advantageous in the following respects:

(1) As the forceps 35 is pushed forward with respect to the cartridge 1, both ends of the ligature, extending from the knots, are pulled in the opposite directions. A tension is applied to the tissue, not in only one direction, and no excessive tension is applied to the tissue. Such a tag or such an arm as used in the apparatus of U.S. Pat. No. 5,312,423 need not be used.

(2) The ligature is first pulled to ligate the tissue to some extent and tight knots are formed, as in the ordinary surgical operation. The tissue can therefore be ligated firmly.

(3) The apparatus enables the surgeon to ligate parts of the tissue, one after another, by replacing each used cartridge 1 with a new one.

(4) Equipped with the forceps 35 which ablates the tissue from the neighboring tissues and which holds the free end of the ligature, the apparatus enables a surgeon to perform not only ligation but also ablation. He or she need not to insert an ablation forceps into the body cavity and pull it therefrom, during the ligation.

(5) Extending parallel to the forceps 35, the ligature holding section 6 would not prevent the forceps 35 from projecting forward with respect to the cartridge 1.

(6) The looped portion L of the ligature is released from the cartridge 35 onto the distal end of the cartridge 1 by pulling the forceps 35 backwards. Therefore, only two components, i.e. the forceps 35 and the cartridge 1, are required to ligate the tissue, simplifying the apparatus. Further, the forceps 35 is of any ordinary type because it need not be mechanically connected to the cartridge as in the apparatus of U.S. Pat. No. 5,312,423. Still further, since the forceps 35 hold the ligature 12, it not necessary to attach a tag to the free end of the ligature as in the use of the apparatus of U.S. Pat. No. 5,312,423.

A ligating apparatus according to the second embodiment will be described with reference to FIGS. 20 to 22.

Figure 20:
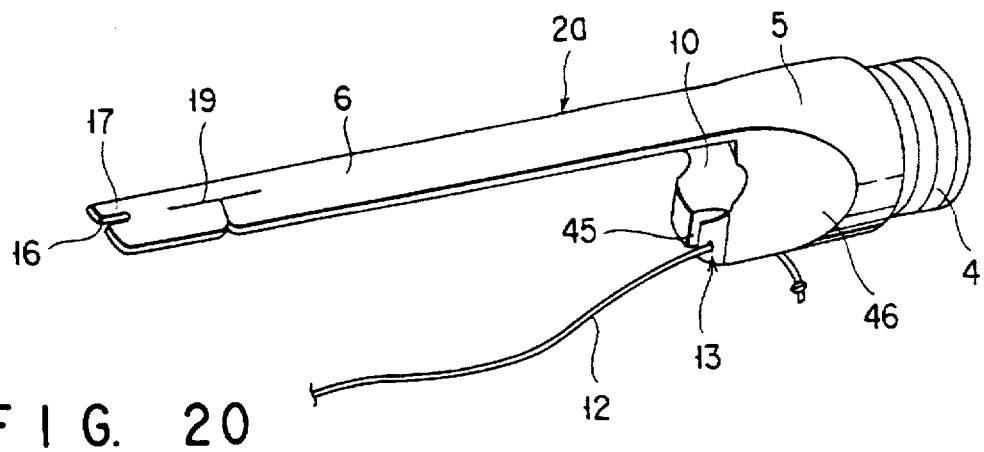
FIG. 20 is a perspective view showing the main body of the ligation cartridge of a ligating apparatus according to a second embodiment of the invention.
Figure 21:
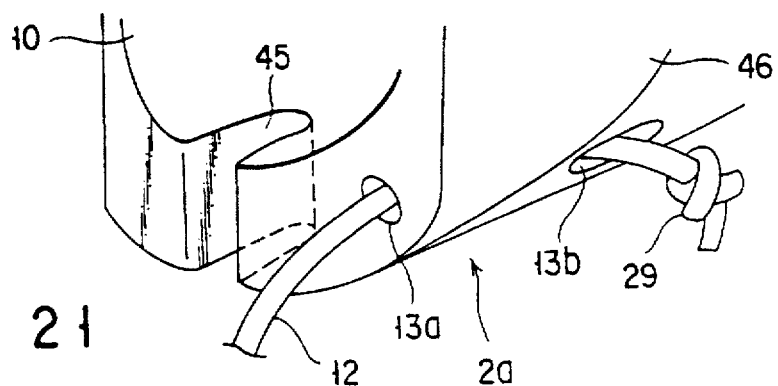
FIG. 21 is a perspective view of the distal end portion of the cartridge shown in FIG. 20.

As shown in FIGS. 20 and 21, the main body 2a of the ligation cartridge embodiment has a notch 45 in the distal end of the loop holding section 5, and the loop holding section 5 has an inclined side 46. Except for these features the second embodiment is identical in structure to the first embodiment.

To use the ligating apparatus according to the second embodiment, a surgeon couples the main body 2a to the distal end of the operation sheath 30 and inserts the Kelly forceps 35 into the sheath 30. The surgeon manipulates the forceps 35 and moves the sheath 30, clamping the free end portion 12a of a ligature 12 between the tongs 41 provided at the distal end of the forceps 35, wrapping it around a tubular tissue 37 and pulling it backwards, thereby to ligate the tubular tissue 37. As the free end portion 12a of the ligature 12 is pulled backwards, it is guided in the notch 45 cut in the loop holding section 5 as shown in FIG. 22. The notch 45 is too narrow to allow the looped portion L of the ligature 12. The looped portion L abuts on the lower side of the section 5 and is tightened, forming knots. The knots are too large to pass through the notch 45. Once the knots are formed, an excessive tension will not be applied on the tubular tissue 37 (e.g., a blood vessel) or the tubular tissue 37 will not be pulled into the operation sheath 30. Hence, there is no possibility that the tissue 37 is severed.

As mentioned above, one side 46 of the loop holding section 5 is inclined. This enables the surgeon to see the free end portion 12a of the ligature 12 more easily than otherwise, while he or she is pulling the portion 12a into the sheath 30 to ligate the tubular tissue 37.

A ligating apparatus according to the third embodiment will be described with reference to FIGS. 23 to 29.

As seen from FIG. 23, the main body 2b of the ligation cartridge comprises a proximal section 50, a ligature holding section 56, and a loop holding section 57. The sections 50 and 57 are hollow cylinders formed integral. They are coaxial and connected together, defining a hole 60, through which a forceps can be passed. The hole 60 has a part 60b in the distal portion of the loop holding section 57. This part 60b has a larger diameter than the remaining part 60a which is formed in the proximal portion of the section 57. A ligature 12, if existing between the forceps inserted in the hole 60 and the inner surface of the part 60b, would not prevent the forceps from moving along its axis.

As shown in FIG. 23, the loop holding section 57 has a large U-notch 53 opening at the distal end. The interior of the section 57 is exposed through the U-notch 53. A blade 54 is set in the bottom of the U-notch 53. The section 57 also has a small U-notch 55 in the distal end and a hole 59 located at the rear of the small U-notch 55. A ligature 12 is passed through the hole 59 into the distal part 60b of the hole 60. The ligature 12 has a knot 29 formed at the rear end and located outside the loop holding section 57. The knot 29 is larger than the hole 59, and the ligature 12 is therefore fastened to the loop holding section 57.

Two pins 51 protrude from the outer circumferential surface of the proximal section 50 of the main body 2b. The pins 51 can fit into two elongated L-notches 52 cut in the distal end of the operation sheath 30. Each L-notch 52 consists of a pin guiding slit 52a and a pin holding slit 52b. The pin guiding slit 52a opens at the distal end of the sheath 30 and extends along the axis of the sheath 30. The pin holding slit 52b extends from the closed end of the pin guiding slit 52a, along the circumference of the sheath 30. To couple the main body 2b to the sheath 30 it suffices to fit the proximal section 50 into the distal end portion of the sheath 30 until each pin 51 abuts on the closed end of the pin guiding slit 52a, and then to rotate the main body 2b around its axis until each pin 51 abuts on the closed end of the pin holding slit 52b. When the main body 2b is thus coupled to the distal end of the operation sheath 30, the proximal section 50 abuts at its proximal end on the rubber packing 300 fitted in the sheath 30, as is illustrated in FIG. 24. The rubber packing 300 biases the section 50 forward, whereby the pins 15 would not slip out of the pin holding slits 52b unless the main body 2b is rotated relative to the operation sheath 30.

The ligature holding section 56 is a slender rod. The section 56 extends forward from the distal end of the loop holding section 57, parallel to the axis of thereof. It has a ligature holding slit 61 in the distal end, for holding the free end portion 12a of the ligature 12.

The loop holder 3a, which is a component of the ligation cartridge, is almost identical to the loop holder 3 of the first embodiment. Namely, the loop holder 3a comprises a ligature holding cylinder 20, a loop stopping cylinder 21, and a base cylinder 22. The base cylinder 22 can fitted into the hole 60 of the main body 2b (more correctly, the proximal part 60a of the hole 60). The loop holder 3a differs from the loop holder 3 in that the ligature holding cylinder 20 is longer than its counterpart of the loop holder 3. The cylinder 20 almost reaches the distal end of the ligature holding section 56, as long as the loop holder 3a is coupled to the main body 2b of the cartridge.

As shown in FIGS. 23, 24 and 25, the ligature 12 extending forward from the main body 2b is wound around the loop holder 3a, forming a looped portion L. The free end portion 12a of the ligature 12 is wound around the ligature holding section 56, forming a helical coil. The free end portion 12a of the ligature 12 is then passed downwards through the ligature holding slit 61 which is formed in the distal end of the ligature holding section 56.

The ligating apparatus according to the third embodiment, comprising the ligating cartridge, the operation sheath 30 and the Kelly forceps 35 (FIG. 25), is operated to ligate a tubular tissue 37, basically in the same way as the first embodiment. To state more specifically, a surgeon first operates the forceps 35, clamping the free end portion 12a of the ligature 12 between the tongs 41 of the Kelly forceps 35, as shown in FIG. 25. The surgeon then pulls the sheath 30 backwards with respect to the forceps 35, releasing the free end portion 12a of the ligature 12 from the ligature holding slit 61. He or she further pulls the sheath 30 backwards, and the coiled portion of the ligature 12 slips from the ligature holding section 56 as illustrated FIG. 26.

Figure 27:
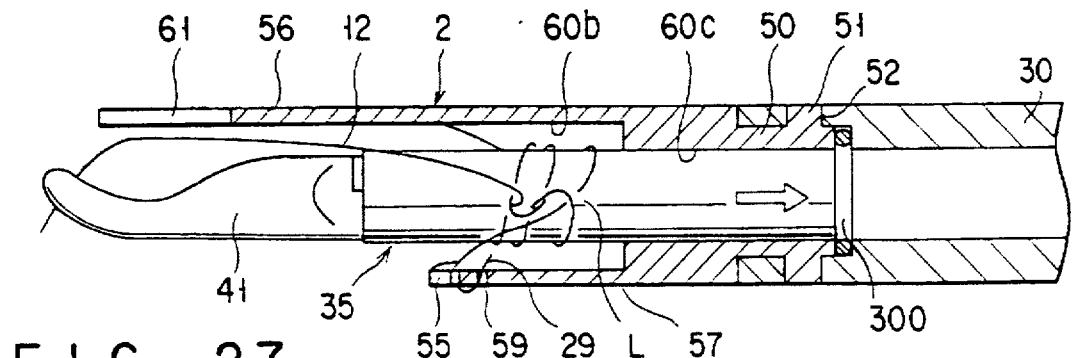
FIG. 27 is a sectional view of the third embodiment, showing the forceps pulled backwards, thereby pulling the free end portion of the ligature into the operation sheath.

Next, the surgeon pulls the forceps 35 backwards into the operation sheath 30 as shown in FIG. 27, whereby the free end portion 12a of the ligature 12 is passed through the looped portion L. The looped portion L is moved from the forceps 35 since the ligature 12 is fastened at the other end to the distal end of the loop holding section 57. At this time, an annular space is provided between the forceps 35 and the inner surface of the section 57 (more precisely, the inner surface of the distal part 60b of the hole 60). Therefore, the ligature 12 is not pinched between the forceps 35 and the inner surface of the section 57, and will neither be cut nor prevent the forceps 35 from moving back or forth.

Figure 28:
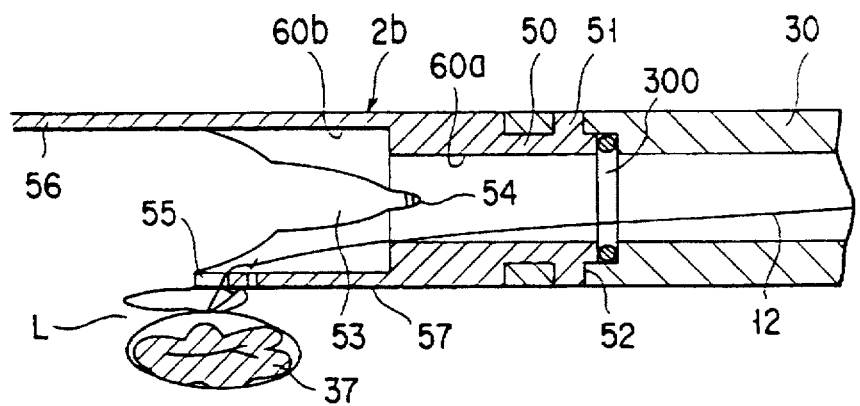
FIG. 28 is a sectional view of the third embodiment, explaining how the free end portion of the ligature is further pulled into the sheath, while passing through the notch cut in the main body of the cartridge.
Figure 29:
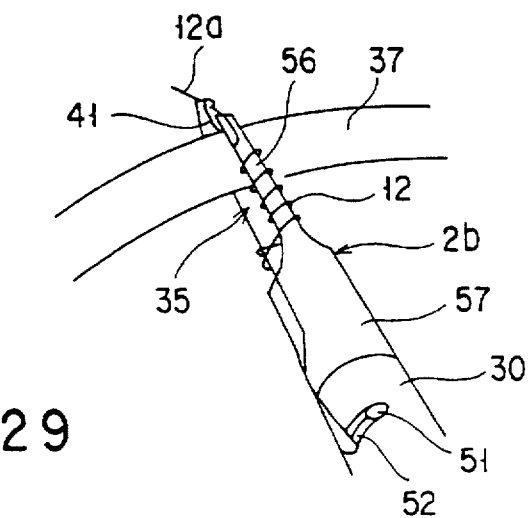
FIG. 29 is a perspective view of the third embodiment, as viewed from above, showing the forceps holding the free end portion of the ligature.

The surgeon further pulls the Kelly forceps 35 into the operation sheath 30, pulling the free end portion 12a of the ligature 12, which is wrapped around the tubular tissue 37. While being thus pulled, the portion 12a of the ligature 12 is guided through the small U-notch 55 cut in the loop holding section 57 as is illustrated in FIG. 28. As the portion 12a of the ligature 12 is further pulled into the sheath 30, guided through the U-notch 55, the looped portion L eventually abuts on the distal end of the section 57. As the portion 12a of ligature 12 is still further pulled, the looped portion L is tightened, forming knots. The tubular tissue 37 is thereby ligated with the ligature 12. Since the knots are too large to pass through the U-notch 55, the free end portion 12a of the ligature 12 can no longer be pulled into the operation sheath 30. Thus, the tubular tissue 37 would not be pulled into the sheath 30 even if it is comparatively thin. Nor would it receive an excessive tension and be severed.

Upon ligating the tubular tissue 37, the surgeon cuts both end portions of the ligature 12 from the knots by using the blade 54 provided on the loop holding section 57. The blade 54 would not damage any tissue since it is set in the bottom of the large U-notch 53 made in the loop holding section 57.

The ligating apparatus according to the third embodiment is used as described above to achieve the above-mentioned advantages. Moreover, the apparatus attain the following additional advantages:

(1) Since the ligature holding section 56 is a slender rod, the surgeon can see well the tissue 37 of interest being ablated from the neighboring tissues and also the free end portion 12a of the ligature 12 held by the tongs 41 of the Kelly forceps 35.

(2) Since the ligature holding section 56 has a slit 61 in its distal end, the free end portion 12a of the ligature 12 is held at the very distal end of the section 56. The surgeon can therefore see well the portion 12a which is to be held by the tongs 41.

Figure 26:
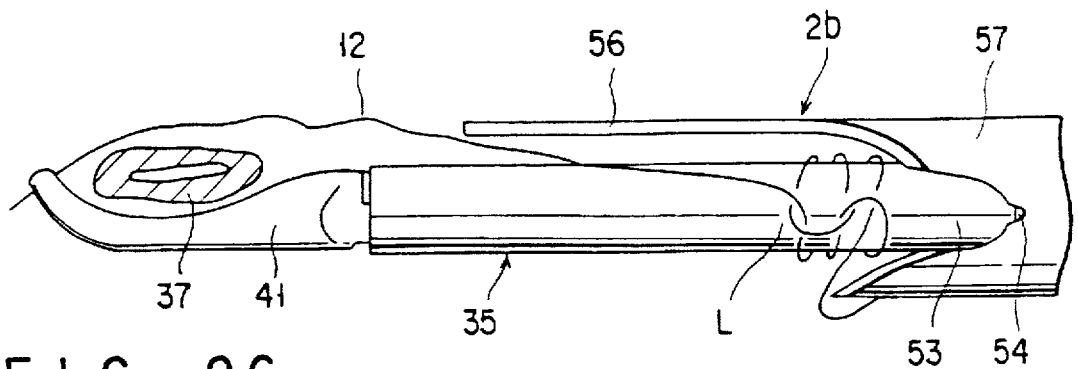
FIG. 26 is a side view of the third embodiment, showing the operation sheath pulled backwards, releasing the free end portion of the ligature from the ligature holding section of the cartridge.

(3) Since the ligature 12 is wound around the ligature holding section 56, it is sufficiently long. Thus, its free end portion 12a can be wrapped around the tissue as shown in FIGS. 25 and 26, without applying an excessive tension on the tissue, even if the tissue is a thick tubular one. Further, being wound around the section 56, the ligature 12 does not slacken when led into the body cavity, and would not be caught by anything while being guided into the body cavity.

(4) The loop holding section 57 has a large U-notch 53 opening in one side of the distal end. Through this U-notch 53 the surgeon can see how the tissue is ligated with the ligature 12.

A ligating apparatus according to the fourth embodiment will be described with reference to FIGS. 30 to 32.

As seen from FIG. 30, the ligation cartridge 70 of the fourth embodiment comprises a ligature holding section 71 and a loop holding section 72. The loop holding section 72 is formed of a loop stopper 75 and a ligature holding section 76. The ligature holding section 76 is a hollow cylinder, having an axial hole 77. The hole 77 is large enough to allow the passage of the distal end portion of a forceps which is used in combination with the loop stopper 75. The loop stopper 75 is a solid cylinder, having a diameter greater than the outer diameter of the ligature holding section 76. Once the ligature holding section 71 is coupled to the loop stopper 75, a loop holding space is defined by the ligature holding section 71, the back of the loop stopper 75, and the outer circumferential surface of the ligature holding section 76.

The loop stopper 75 has a groove 74 in its circumferential surface. The groove 74 has a cross section which is virtually identical in shape and size to that of the ligature holding section 71. Hence, the loop stopper 75 holds the section 71 once the ligature holding section 71 is passed through the hole 74. As shown in FIG. 32, the loop stopper 75 has a pair of projections 89 located above the groove 74, for preventing the ligature holding section 71 from slipping out of the groove 74. The groove 74 and the projections 89 have been formed by making a through hole in the stopper 75 and cutting a narrow slit S which opens to the through hole.

As illustrated in FIG. 31, the ligature holding section 71 is a slender rod. The section 71 has a ligature holding slit 73 in the distal end. The slit 73 extends in the axial direction of the section 71, for holding the free end portion 12a of the ligature 12. The ligature holding section 71 has a blade 78 and a ligature holding hole 80. The blade 78 is provided on the proximal end portion of the section 71. The ligature holding hole 80 is located in front of the blade 78.

The ligature holding section 71 has a pair of legs 70a and 70b at its proximal end. The legs 70a and 79b constitute the proximal portion which can be fitted into the hole 92 of an operation sheath 30 as shown in FIG. 31, to couple the ligature holding section 71 to the operation sheath 30.

The ligation cartridge 70 is used, with the ligature holding section 71 passed through the groove 74 of the loop holding section 72 as shown in FIG. 30. The ligature 12 is passed through the ligature holding hole 80 of the section 71, and its proximal end portion is tied to the section 71. The ligature 12 is then wound around the ligature holding section 76 of the loop holding section 72, forming a looped portion L. Thereafter, the free end portion 12a of the ligature 12 is passed downwards through the ligature holding slit 73 cut in the distal end of the ligature holding section 71.

As shown in FIG. 32, a surgeon inserts a Kelly forceps 35 into the operation sheath 30 from the proximal end thereof. He or she inserts the forceps 35 further into the hole 77 of the loop holding section 72, while holding the ligature holding section 71 in hand. The loop holding section 72 is thereby removed from the ligature holding section 71 as shown in FIG. 32. The looped portion L of the ligature 12 is released from the section 72 and mounted onto the forceps 35, because the ligature 12 is fastened at both ends to the ligature holding section 71.

Then, the surgeon pushes both legs 79a and 79b of the section 71 into the hole 85 of the operation sheath 30, elastically deforming the legs 79a and 79b. The legs 79a and 79b are pushed into the hole 85 until their latching parts 82 fit into the large-diameter portion 92 of the hole 85 as illustrated in FIG. 31. The ligature holding section 71 is thereby coupled to the operation sheath 30. Thereafter, the surgeon operates the ligating apparatus in the same manner as the apparatus of the first embodiment, thereby to ligate the tissue of interest.

The ligating apparatus according to the fourth embodiment attains the same advantages as the first embodiment. In addition, it is advantageous in that the cartridge 70 can easily be coupled to the operation sheath 30, by pushing the legs 79a and 79b into the sheath 30 until the latching parts 82 fit into the large-diameter portion 92 of the hole 85 of the sheath 30. Further, since the ligature holding section 71 is a slender rod, the surgeon can therefore see well the free end portion 12a of the ligature 12 he or she is going to hold by means of the forceps 35.

In the fourth embodiment, the operation sheath 30 may be replaced by one which has an axial slit and which therefore has a U-shaped cross section.

A ligating apparatus according to the invention will be described, with reference to FIGS. 33A and 33B, FIGS. 34 to 38 and FIGS. 39A and 39B.

As shown in FIG. 33A, the ligation cartridge 100 of the fifth embodiment comprises a main body 2c and a loop holder 3. The loop holder 3 is identical to its counterpart of the first embodiment, and will not be described in detail. The main body 2c is comprised of a ligature holding section 110 and a hollow cylindrical base section 112. As seen from FIGS. 33A and 33B, the section 110 has two ligature holding grooves 104 and 106 in the distal and proximal ends, for holding end portions a ligature 12, respectively. A cutter 105 is provided in the ligature holding groove 106.

The base section 112 has a male screw 112a on its outer circumferential surface. A female screw is cut in the inner circumferential surface of the distal end portion of an operation sheath 140 which will be described later. It is in this female screw that the male screw on the hollow cylindrical base section 112 can be set in engagement when the cartridge 100 is coupled to the operation sheath 140. The main body 2c of the cartridge 100 has a through hole 118 and a ligature holding hole 13. The base cylinder 22 of the loop holder 3 can be fitted in the through hole 118 of the main body 2c. The ligature holding hole 13 is identical to its counterpart of the first embodiment.

The ligation cartridge 100 is used, with the loop holder 3 connected to the main body 2c—more precisely, with the base cylinder 22 of the holder 3 fitted in the through hole 118 of the main body 2c. The ligature 12 has one end fastened to the ligature holding hole 13 of the main body 2c. Its free end portion is first wound around the ligature holding cylinder 20, forming a looped portion L, and then held in the groove 104 made in the distal end of the ligature holding section 110. The free end of the ligature 12 is connected to a sutural needle 103. The needle 103 has such a shape and a size that it may pass through the operation sheath 140.

Figure 34:
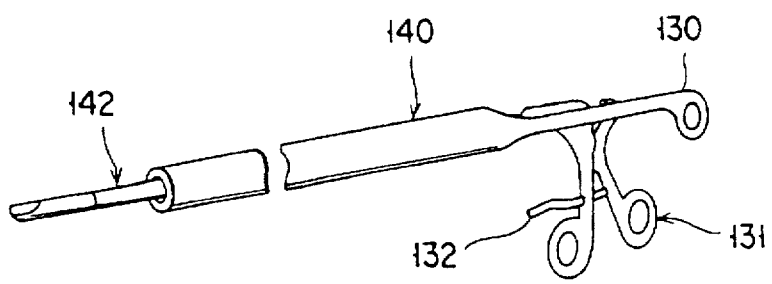
FIG. 34 is a perspective view of the operation sheath and the forceps, both incorporated in the fifth embodiment, the forceps passing through the sheath.
Figure 36:
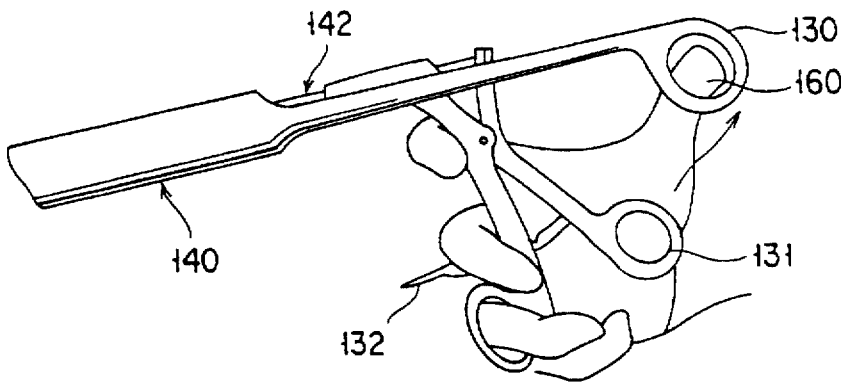
FIG. 36 is a diagram, explaining how to operate the forceps shown in FIG. 34 and the distal end of the operation sheath.

As illustrated in FIG. 34, the fifth embodiment further comprises the operation sheath 140 and a forceps 142 passing through the sheath 140. A handle 130 projects from the proximal end of the operation sheath 140. The handle 130 is so positioned that a surgeon can operate it as well as the handle 131 connected to the forceps 142, with the thumb, while holding another handle connected to the forceps 142, as is illustrated in FIG. 36. The forceps 142 is a needle holder which has ratchet 132 on the handle 131.

The ligation cartridge 100 is coupled to the operation sheath 140 in the same way the cartridge 1 is connected to the sheath 30 in the first embodiment. That is, the forceps 142 is inserted into the operation sheath 140 as shown in FIG. 34, and the cartridge 100 is coupled to the distal end of the sheath 140, thereby assembling the ligating apparatus.

It will be explained how a surgeon operates the ligating apparatus thus assembled, in order to suture a tissue which has a cut and which is present in a patient's body cavity.

Figure 35:
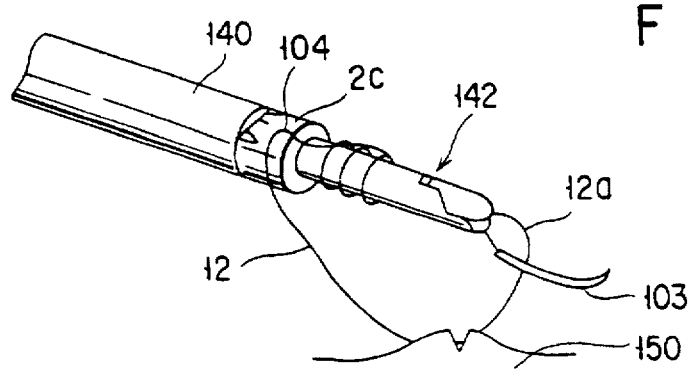
FIG. 35 is a perspective view of the distal end portion of the fifth embodiment, explaining how the ligating apparatus is operated to ligate a tissue.

At first, the surgeon inserts the distal end portion of the apparatus into the body cavity. He or she manipulates the forceps 142, holding the sutural needle 103, passing the needle 103 through the tissue 150, pulling the free end portion 12a of the suture 12, in the body cavity as is illustrated in FIG. 35. In this condition, the surgeon sets the ratchet 132, moves the thumb 160 from the handle 131 of the forceps 142, and holds the handle 130 as shown in FIG. 36. The surgeon then moves the handle 130, thereby to move the operation sheath 140 back and forth.

Figure 37:
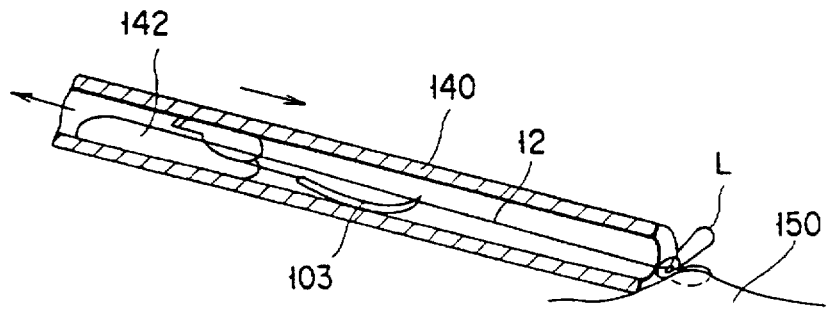
FIG. 37 is a sectional view of the operation sheath, showing how the free end portion of a ligature is pulled into the sheath.

Next, the surgeon pulls the sheath 140 with respect to the forceps 142, thereby releasing the suture 12 from the groove 104 cut in the distal end of the ligature holding section 110. This done, the surgeon pulls the forceps 142 into the operation sheath 140. Since the free end portion 12a of the suture 12 is held by the forceps 142, the looped portion L is released from the forceps 142. As a result, the free end portion 12a of the suture 12 passes trough the looped portion L, as shown in FIG. 37.

Thereafter, the surgeon sutures the tissue 150 in the same manner as he or she ligates a tissue by using the ligating apparatus according to the first embodiment. To be more specific, he or she pulls the forceps 142 with respect to the sheath 140, thus pulling the free end portion 12a of the suture 12. As the portion 12a is pulled, the looped portion L is tightened, forming knots. The tissue 150 is thereby sutured to some extent as shown in FIG. 37. The surgeon pulls the operation sheath 140, thus pushing the forceps 142 forward, moving the distal ends of the sheath 140 and the forceps 142 away from each other. Hence, the free end portion 12a of the suture 12 is moved forward, while the proximal end of the suture 12 is pulled, as illustrated in FIG. 38. The knots are therefore tightened, whereby the tissue 150 is sutured completely and the cut in the tissue 150 is closed. Next, the surgeon pushes the forceps 142 forwards, pulling the proximal end portion of the suture 12 as shown in FIG. 39A and eventually cuts it from the knots by means of the cutter 105 provided on the main body 2a of the cartridge 100. Then, he or she guides the suture 12 through the groove 106 made in the proximal end of the ligature holding section 110 and cuts both end portions of the suture 12 from the knots, as is illustrated in FIGS. 39A and 39B.

Since the sutural needle 103 is connected to the free end of the suture 12, the surgeon can suture the tissue 150 by manipulating the forceps 142, while holding the needle 103 by the forceps 142. Since the main body 2c of the ligation cartridge 100 has no projection such as the ligature holding section 6 used in the first embodiment, the surgeon can see the looped portion L he or she is tightening.

Moreover, the surgeon can easily hold the suture 12 in ligature holding groove 106 because this groove 106 opens to the proximal end of the ligature holding section 110, not to the distal end thereof. Further, the suture 12 smoothly slips into the groove 106 when moved along the operation sheath 140, because the section 110 has the same outer diameter and the sheath 140 and is coaxial with the sheath 140. Still further, located in the groove 106, the cutter 105 has no chance of contacting the tissue 150 and would not damage the tissue 150 at all.

As described above, the handle 130 projecting from the sheath 140 is positioned such that the surgeon can operate it with the thumb, while operating the handle 131 on the forceps 142 with the fingers. Thus, the surgeon can operate the ligating apparatus by a single hand.

A ligating apparatus according to the sixth embodiment of the present invention will be described, with reference to FIGS. 40A and 40B, FIGS. 41A and 41B, FIGS. 42A and 42B, and FIGS. 43 to 47.

Figure 40A:
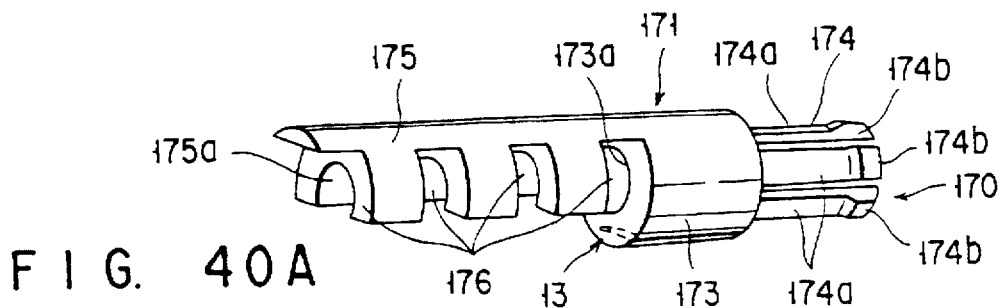
FIG. 40A is a perspective view of the main body of the ligation cartridge used in a ligating apparatus according to a sixth embodiment of the invention.
Figure 40B:
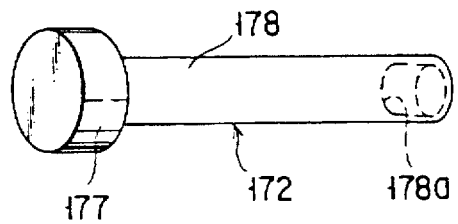
FIG. 40B is a perspective view of the loop holder of the ligation cartridge.

As shown in FIGS. 40A and 40B, the ligation cartridge 170 of the sixth embodiment comprises a main body 171 and a loop holder 172.

As seen from FIG. 40A, the main body 171 is formed of a ligature holding section 173, a base section 174, and a loop holding section 175. The loop holding section 175 is a half of a hollow cylinder. The ligature holding section 173 is a hollow cylinder connected to the proximal end of the section 175. The base section 174 protrudes from the proximal end of the section 173 and is made of a plurality of legs 174a. The section 174 can be fitted into the distal end of an operation sheath 140, which is a component of the ligating apparatus.

The main body 171 has a hole, through which a forceps 142, i.e., another component of the apparatus, can pass. The hole consists of a groove 175a of the loop holding section 175, a hole 173a of the ligature holding section 173 and the space defined by the legs 174a. The hole has a diameter a little larger than the outer diameter of the forceps 142.

The loop holding section 175 has a plurality of slits 176 communicating with the groove 175a. These slits 176 serve as loop holding spaces 176a to 176d.

The ligature holding section 173 has a ligature holding hole 13 for holding one end portion of the ligature 12. The ligature holding hole 13 is identical to its counterpart of the first embodiment.

As described above, the base section 174 is comprised of the legs 174a which project from the proximal end of the ligature holding section 173 and which extend parallel to the axis of the main body 171. Each leg 174a has a latching part 174b on the proximal end. The latching parts 174b of the legs 174a can fit into the large-diameter portion 180a of the hole 180 of the operation sheath 140, when pushed into the operation sheath 140.

As illustrated in FIG. 40B, the loop holder 172 is a columnar member, comprised of a loop stopping cylinder 177 and a ligature holding cylinder 178 which are formed integral. The cylinder 177 has a larger diameter than the ligature holding cylinder 178. The cylinder 178 has a recess 178a in the proximal end. The distal end of the forceps 142 can fit into the recess 178a.

Figure 41A:
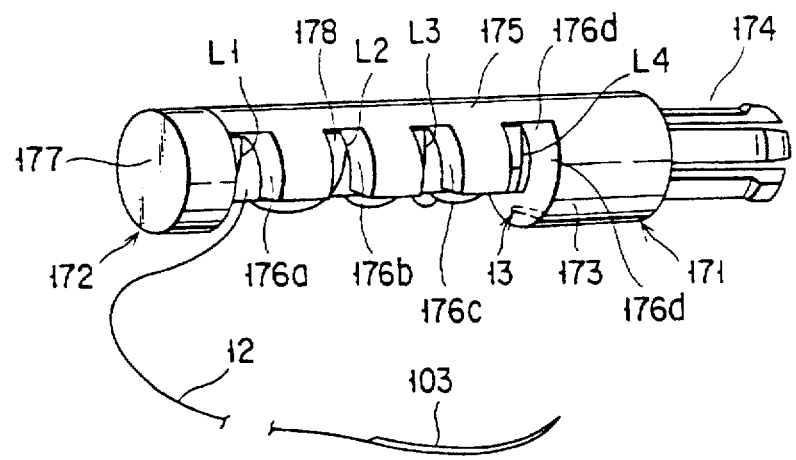
FIGS. 41A and 41B are diagrams illustrating the cartridge main body and the loop holder, combined together.
Figure 41B:
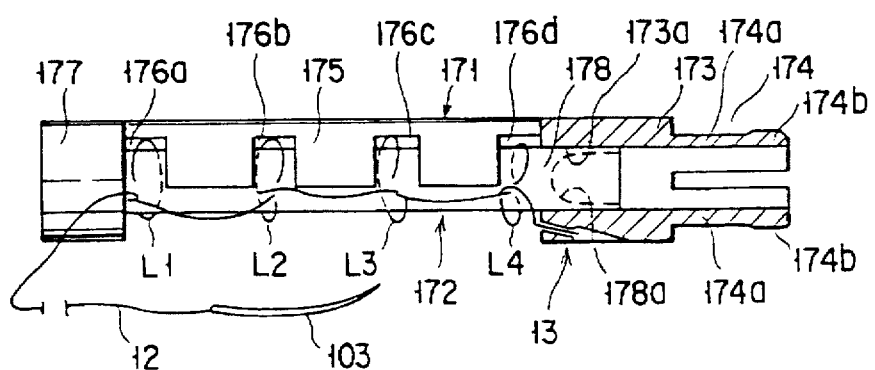

The ligation cartridge 170 is used, with the distal end portion of the ligature holding cylinder 178 inserted in the hole 173a of the ligature holding section 173, and the remaining portion of the cylinder 178 fitted in the groove 175a of the loop holding section 175—as is illustrated in FIGS. 41A and 41B. A ligature 12 is wound around the cartridge 170, forming loops. A sutural needle 103 is connected to the distal end of a ligature 12. The proximal end of the ligature 12 is inserted into the hole 13 of the ligature holding section 173 and held therein by, preferably, adhesive. The ligature 12 is wound around the ligature holding cylinder 178 of the loop holder 172, forming loops. The loops are held in the loop holding spaces 176a to 176d. In other words, the ligature 12 extending from the section 173 is wound around the cylinder 178 in the same way as is shown in FIG. 4, except that four loops $L_1$ to $L_4$, not three, are formed. These loops $L_1$ to $L_4$ are held in the spaces 176a to 176d, respectively.

It will be explained how a surgeon operates the ligating apparatus according to the sixth embodiment in order to suture a tissue 150 which has a cut and which is present in a patent's body cavity.

Figure 42A:
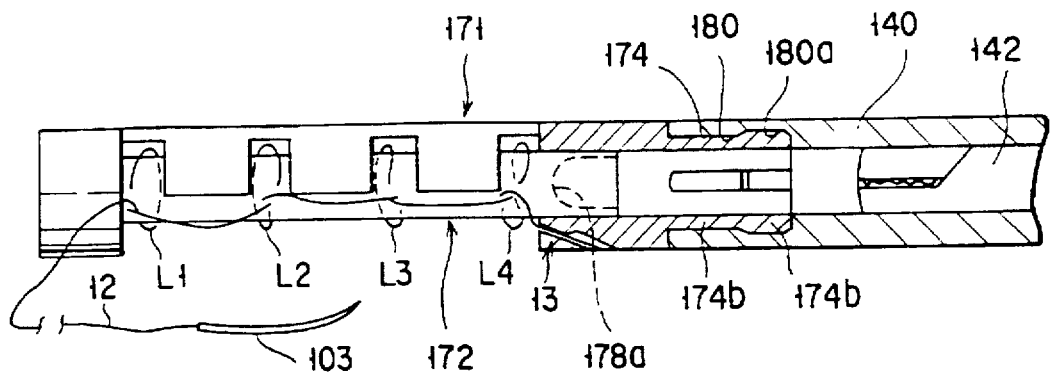
FIGS. 42A and 42B are diagrams explaining how the cartridge is used to mount loops of a ligature on the forceps.

At first, the surgeon inserts the forceps 142, which is a needle holder, into the operation sheath 140 as shown in FIG. 34. The surgeon inserts the base section 174 of the main body 171 into the hole 180 of the operation sheath 140 until the latching parts 174b of the legs 174a fit into the large-diameter portion 180a of the hole 180. The ligation cartridge 170 is thereby coupled with the operation sheath 140 as is illustrated in FIG. 42A.

Figure 42B:
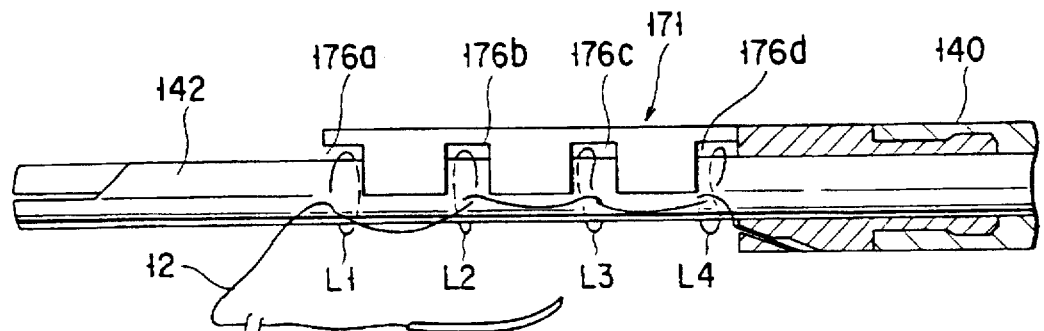

Next, the surgeon pushes the forceps 142 through the hole of the main body 171 of the cartridge 170, thereby inserting the distal end of the forceps 142 into the recess 178a of the loop holder 172. He or she further pushes the forceps 142, moving the loop holder 172 forward. As the loop holder 172 is pushed forward, the loops $L_1$ to $L_4$ of the suture 12 are mounted onto the forceps 142 as shown in FIG. 42B. This is because the loops $L_1$ to $L_4$, held in the spaces 176a to 176d, are not moved forward together as the loop holder 172 is pushed forward.

Figure 43:
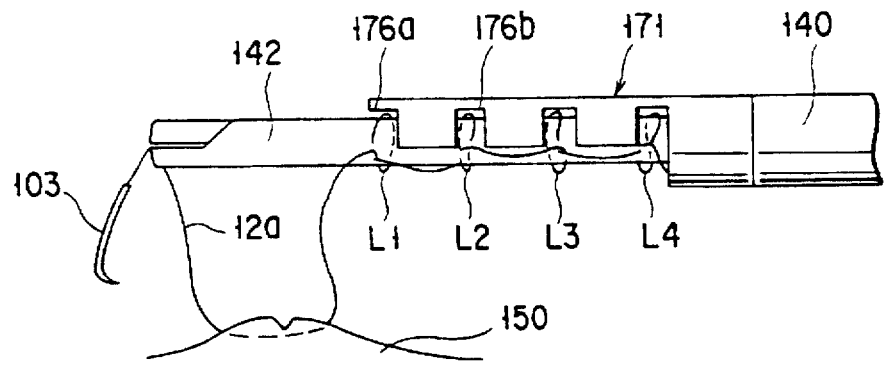
FIG. 43 is a diagram explaining how the sutural needle connected to the ligature is passed through a tissue.

Then, the surgeon inserts the distal end portion of the ligating apparatus into the patient's body cavity. The surgeon manipulates the forceps 142, holding the sutural needle 103, passing the needle 103 through the tissue 150, pulling the distal end portion 12a of the suture 12, in the body cavity as shown in FIG. 43. In this condition, the surgeon sets the ratchet (not shown) provided at the proximal end of the forceps 142.

Figure 44:
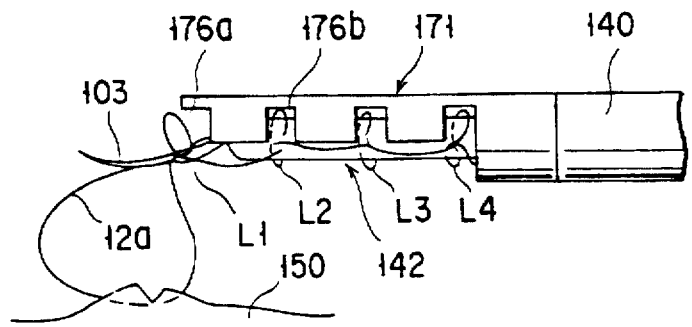
FIG. 44 is a diagram explaining how to pull the free end portion of the ligature into the first loop of the ligature.

Thereafter, the surgeon pushes the sheath 140 with respect to the forceps 142, releasing the first loop $L_1$ from the forceps 142. To state it more exactly, the sheath 140 is moved forward relative to the forceps 142 until the wall of the loop holding space 176a pushes the first loop $L_1$ from the distal end of the forceps 142. As a result, the distal end portion 12a of the suture 12 is passed through the first loop $L_1$ as shown in FIG. 44.

The surgeon pushes the forceps 142 with respect to the operation sheath 140, moving the end portion 12a of the suture 12 forward from the first loop $L_1$. He or she further pushes the forceps 142, pulling the suture 12 at both ends in the opposite directions, tightening the first loop $L_1$ and forming a first knot. The tissue 150 is thereby sutured to some extent as illustrated in FIG. 45.

Next, the surgeon moves the operation sheath 140 relative to the forceps 142 until the second loop holding space 176b reaches the distal end of the forceps 142. When the space 176b reaches the distal end of the forceps 142, the second loop $L_2$ falls from the forceps 142. The distal end portion 12a of the suture 12 is therefore passed through the second loop $L_2$ as shown in FIG. 46. The surgeon then pushes the forceps 142 with respect to the sheath 140, thus pulling the suture 12 at both ends in the opposite directions. The second loop $L_2$ is thereby tightened and forms a second knot on the first knot as illustrated in FIG. 47. The tissue 150 is sutured more firmly but not completely.

Thereafter, the surgeon repeatedly moves the operation sheath 140 and the forceps 142 in the same manner as described above, thereby forming a third knot and a fourth knot. Now that four knots are formed on the suture 12 passed through the tissue 150, the tissue 150 is completely sutured and the cut in the tissue 150 is closed.

Since the suture 12 is repeatedly pulled at both ends in the opposite direction, each time forming a knot, an excessive tension is not applied to the tissue as in the case where the suture is pulled at one end and, hence, in one direction.

Held in the loop holding spaces 176a to 176d, the loops of the suture 12 are released from the forceps 142, one after another, not simultaneously. Hence, they are sequentially tightened, and knots are formed one after another, as in the ordinary surgical operation. The use of the cartridge 170 enables the surgeon to form four knots at the most.

The slits 176 are open at the sides of the main body 171, forming a continuous space. Even if the forceps 142 is much pulled into the sheath 140, the sutural needle 103 connected to the distal end of the suture 12 would not be pulled into the loop holding spaces 176a to 176d. The slits 176 make it possible for the surgeon to use sutural needles which cannot be pulled into the sheath 140 due to their size and shape.

A plurality of knots can be formed, merely by moving the sheath 140 and the forceps 142, relative to each other.

Moreover, the loops of the suture 12 can be tightened one after another, thus tightening the tissue 150. They can be easily tightened even if the suture 12 is, for example, a multi-filament one which does not smoothly run.

A ligating apparatus 200 according to a seventh embodiment of the invention will be described, with reference to FIGS. 48 and 49.

As can be understood from FIGS. 48 and 49, the ligating apparatus 200 comprises a loop holder 3, a forceps 142, and a sheath section 201. The sheath section 201 is made of a cartridge main body 2 and an operation sheath 140, which are connected together and which are of the same type as their counterparts of the first embodiment. The loop holder 3 is removably coupled to the sheath section 201 and is identical to its counterpart of the first embodiment.

The sheath section 201 contains an O-ring (not shown). As shown in FIG. 49, when the forceps 142 is inserted into the sheath section 201, it passes through the O-ring, achieving airtight sealing between the forceps 142 and the O-ring. As shown in FIG. 48, the proximal portion 202 of the sheath section 201 is thicker than the other portion, having an outer diameter larger than the inner diameter of a trocar (not shown) through which the distal end portion of the apparatus 200 is to be inserted into a patient's body cavity.

To use the ligating apparatus 200, a surgeon inserts the forceps 142 into the sheath section 201, from the proximal end thereof, a ligature is wound around the loop holder 3, forming a looped portion L, and holds the free end portion 12a of the ligature in the slit 19 cut in the distal end of the sheath section 201. The surgeon then inserts the distal end portion of the apparatus 200 into the patient's body cavity. Thereafter, he or she operates the ligating apparatus 200 in the same way as the first embodiment, thereby to ligate a tissue present in the body cavity.

The forceps 142 can be easily replaced by another, merely by pulling it from the sheath section 201 and inserting the other forceps thereinto. Furthermore, the sheath section 201 is prevented from being inserted further into the body cavity when its proximal portion 202 abuts on the trocar (not shown) through which the section 201 is inserted into the body cavity.

A ligating apparatus 210 according to the eighth embodiment according to the present invention will be described, with reference to FIGS. 50 to 66.

Figure 50:
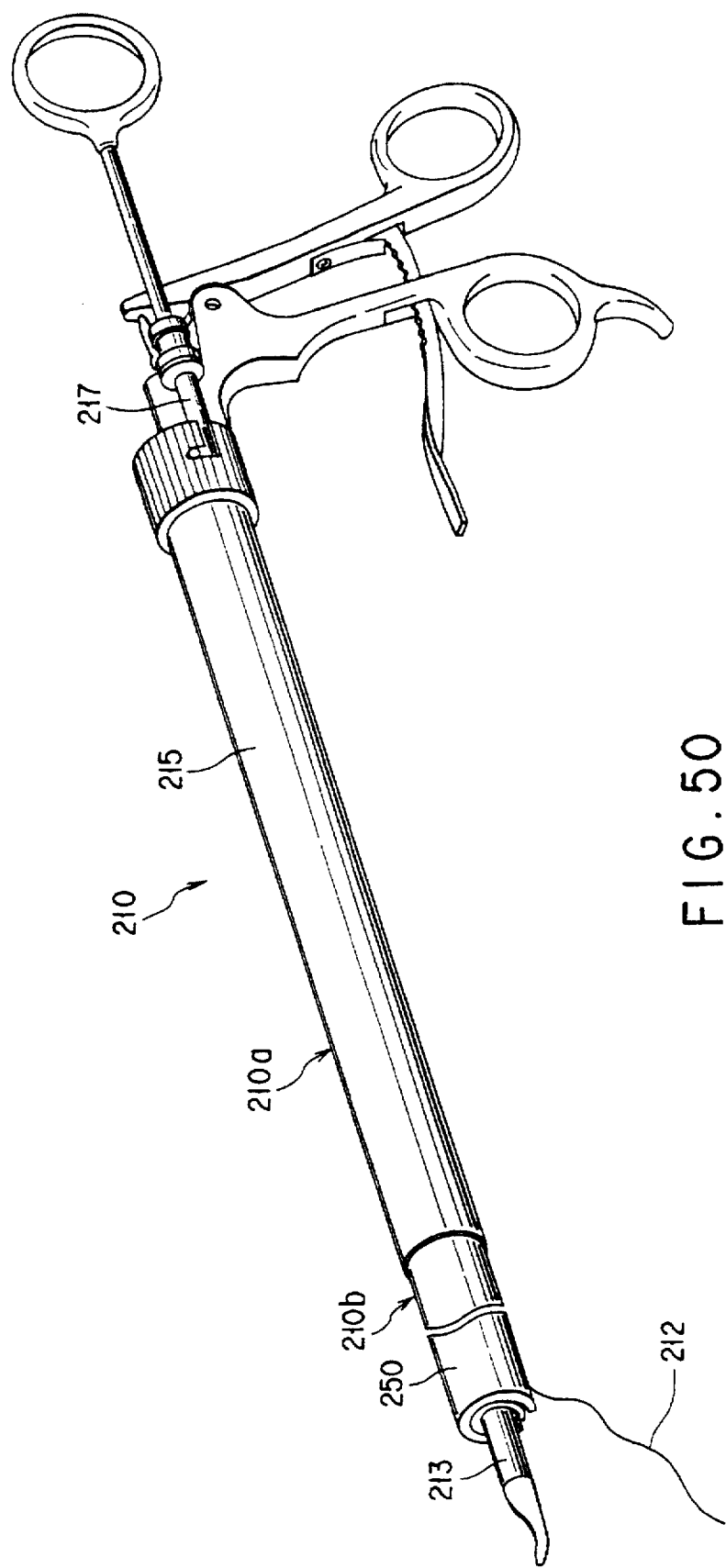
FIG. 50 is a perspective view of a ligating apparatus according to an eighth embodiment of the present invention.

As shown in FIG. 50, the ligating apparatus 210 comprises a forceps section 210a and a cartridge section 210b. The cartridge section 210b is made of a main body 250 and an operation section 217, which is removably coupled to the main body 250. The forceps section 201a is made of a forceps 213 and a sheath 215. The sheath 215 covers the forceps 213 and the cartridge section 210b.

Figures 51A, 51B, 52:
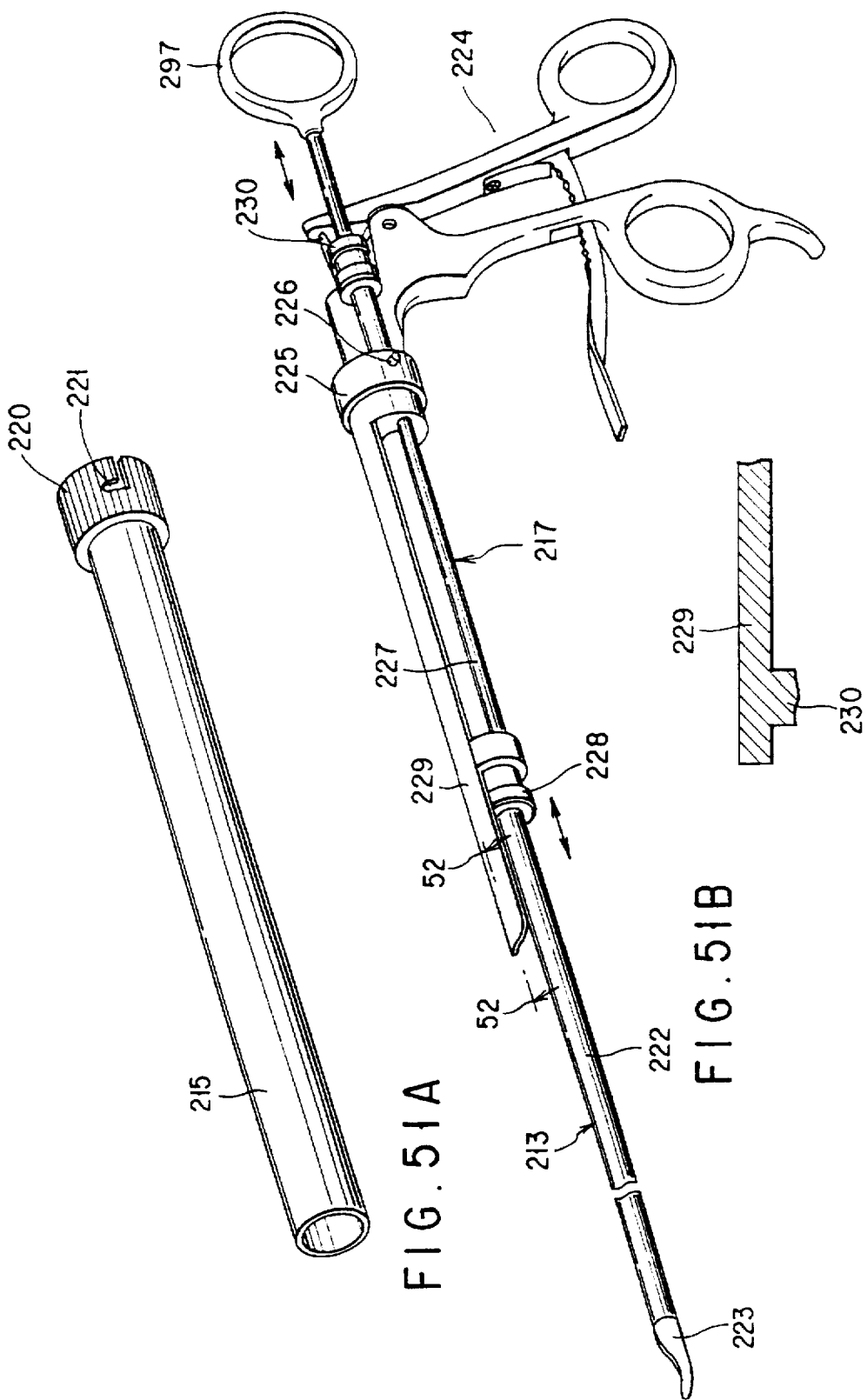
FIGS. 51A and 51B are an exploded view of the ligating apparatus shown in FIG. 50.
FIG. 52 is a sectional view, taken along line 52—52 in FIG. 51B.

As illustrated in FIG. 51A, the sheath 215 of the forceps section 210a is a hollow cylinder and has a base 220 at the proximal end. The base 220 has an L-shaped slit 221. As may be understood from FIG. 51B, the forceps 213 is similar to one used in most surgical operations. It is a Kelly forceps which surgeons can easily manipulate to ablate a tissue and wrap a ligature around the tissue.

The forceps 213 comprises a shaft 222, tongs 223, and an operation section 224. The tongs 223 are connected to the distal end of the shaft 222 and can be opened and closed. The operation section 224 is connected to the proximal end of the shaft 222. When operated, the section 224 opens and close the tongs 223. The tongs 223 are curved at the distal end thereof. To the proximal end of the shaft 222 there is connected a hollow cylinder 225, which is fitted in the base 220 of the sheath 215. A pin 226 protrudes from the hollow cylinder 225 in the radial direction thereof and is fitted in the L-shaped slit 221 of the base 220. An arm 229 extends long from the distal end of the hollow cylinder 225, in parallel to the shaft 222. As shown in FIG. 52, a cam pin 230 projects downwards from the distal end of the arm 229.

As seen from FIG. 51B, the operation section 217 of the cartridge section 210b is movably mounted on the shaft 222. The section 217 comprises a rod 227 and a handle 297. The rod 227 extends parallel to the forceps 213, passing through the hollow cylinder 225 of the forceps 213. The handle 297 is fastened to the proximal end of the rod 227 and located near the operation section 224. When operated, the handle 297 pushes and pulls the rod 227. A latch 228 is provided on the distal end of the rod 227. A seal (not shown), such as a rubber cap, is mounted on that portion of the rod 227 which is fitted in the hollow cylinder 225 of the forceps 213.

Figures 55A, 55B:
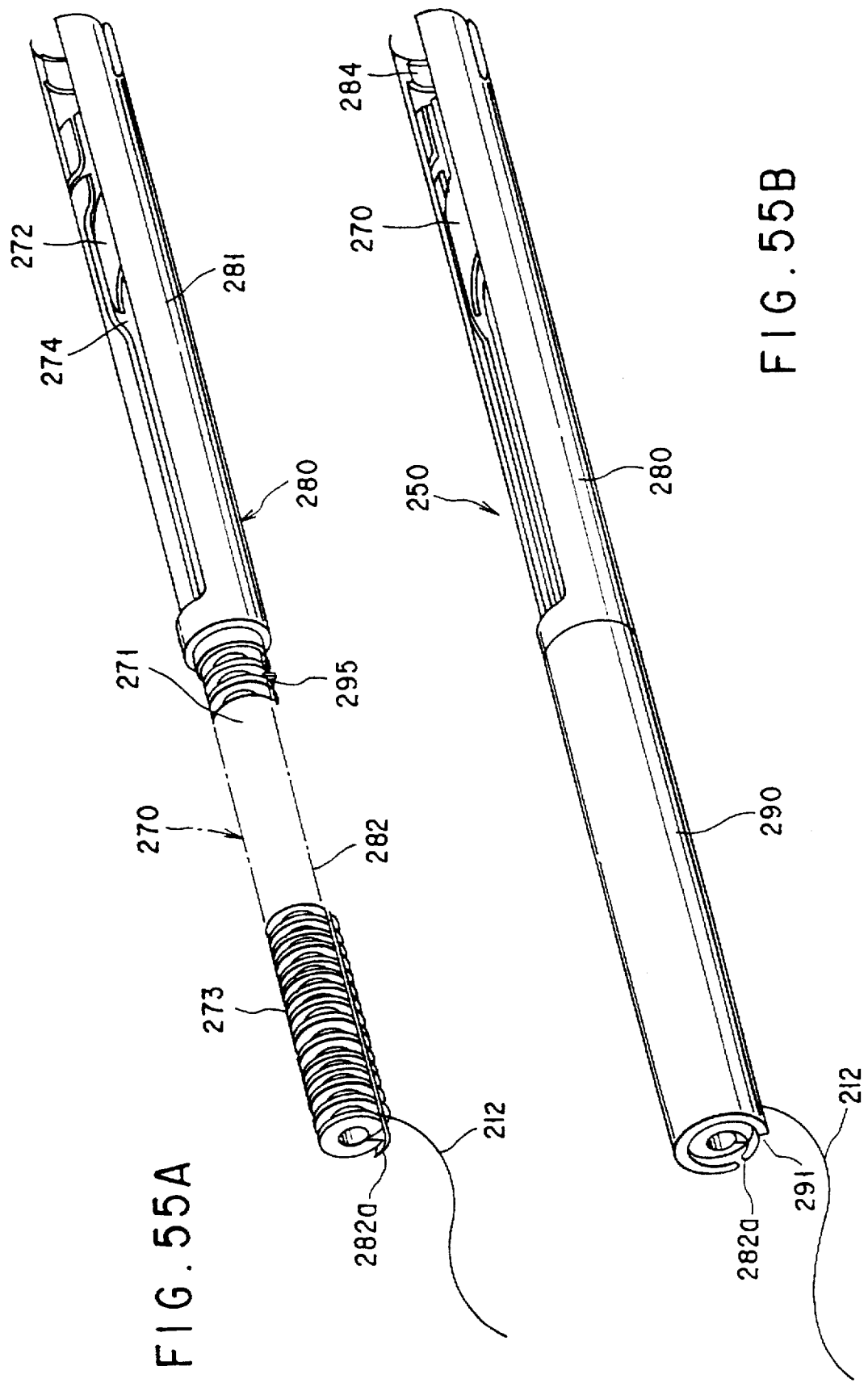
FIG. 55A is a perspective view of the cartridge, ligature holder and case, combined together, of the apparatus shown in FIG. 50.
FIG. 55B is a perspective view of the cartridge of the apparatus shown in FIG. 50.

As shown in FIG. 55B, the main body 250 of the cartridge section 210b is comprised of a ligature holder 270, a case 280 and a cover 290. The ligature holder 270 is provided to hold loops of a ligature 212. The ligature holder 270 has a ligature holding section 271 at the distal end. The case 280 contains the ligature holder 270 and is set in engagement with the latch 228 provided on the distal end of the rod 227. The cover 290 covers the ligature holding section 271.

Figures 53A, 53B, 53C:
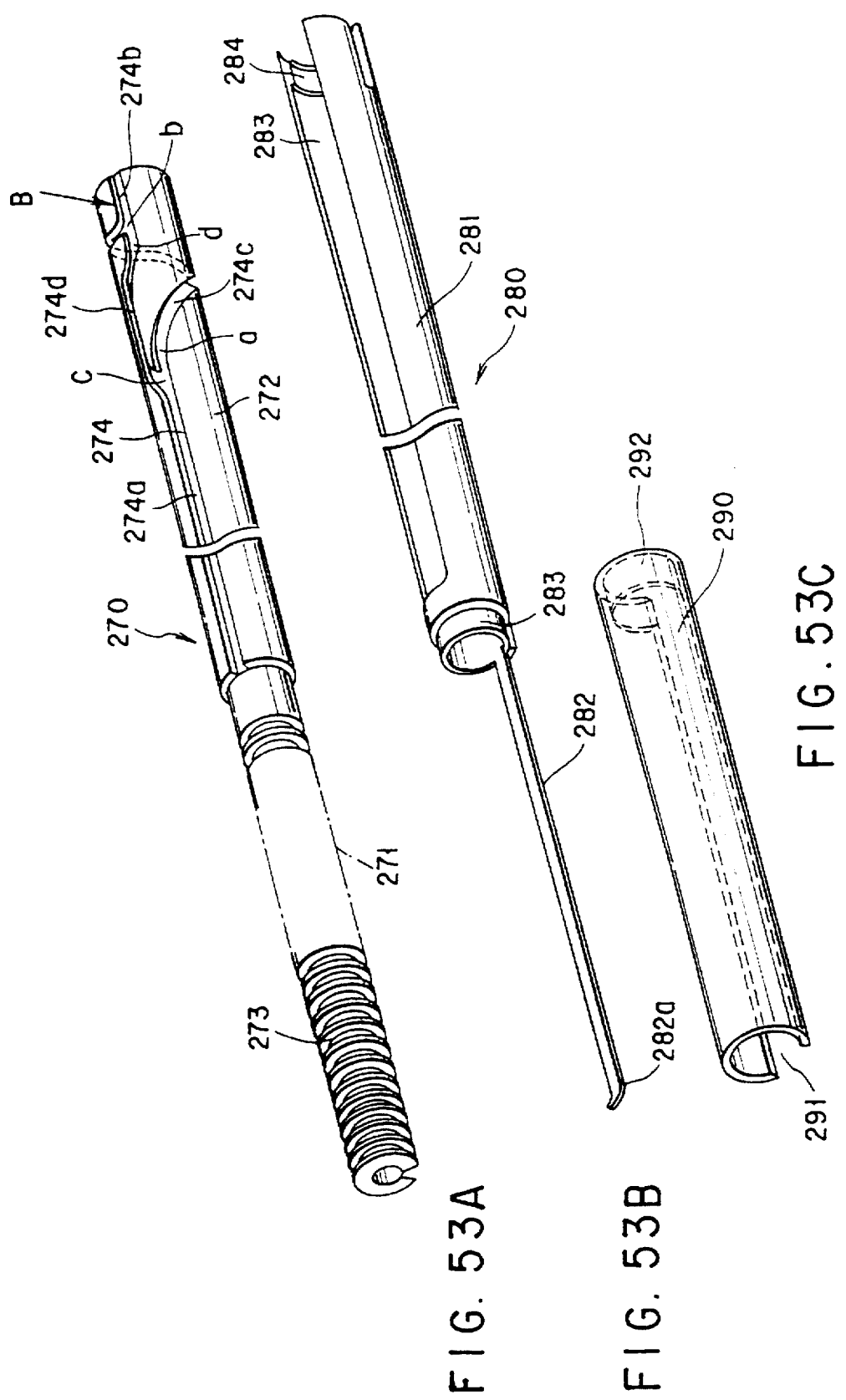
FIGS. 53A to 53C are exploded views of the cartridge which is one component of the ligating apparatus shown in FIG. 50.

As shown in FIG. 53A, the ligature holder 270 is a hollow cylinder, through which the shaft 222 of the forceps 213 can pass. The ligature holder 270 comprises the ligature holding section 271 and a proximal portion 272. The section 271 has a helical groove 273 cut in its entire circumferential surface. The ligature 212 is wound around the section 271, along the helical groove 273. The proximal portion 272 has a cam groove 274 formed in the outer circumferential surface. It is in the cam groove 274 that the cam pin 230 projecting from the distal end of the arm 229 is loosely fitted. As seen from FIG. 54 which is a developed view of the groove 274, the cam groove 274 consists of two straight portions 274a and 274b, a helical portion 274c, and a bypass portion 274d. The first straight portion 274a extends from the rear end to distal end of the helical groove 273. The second straight portion 274b is shorter than, axially aligned with, and spaced part from, the first straight portion 274a. The helical portion 274c from the rear end a of the first straight portion 274a to the distal end portion b of the second straight portion 274b, thus connecting the straight portions 274a and 274b. The bypass portion 274d connects the distal end d of the second straight portion 274b to the rear end portion c of the first straight portion 274a. The helical portion 274c turns in the direction opposite to that in which the helical groove 273 turns.

Referring back to FIG. 53B, the case 280 comprises a hollow cylindrical body 281 and a long strip 282. The body 281 contains the proximal portion 272 of the ligature holder 270, allowing the portion 272 to rotate around its axis. The body 281 has an elongated slit 283 and a latching part 284. The slit 283 is made in the circumference of the body 281 and extends parallel to the axis of the case 281. In the slit 283 the arm 229 of the forceps 213 can be fitted. The latching part 284 is provided on the inner circumferential surface of the distal end of the body 281. The strip 282 is so long that its distal end 282a projects from the distal end of the ligature holding section 271 when the ligature holder 270 is inserted into the case 280 from the proximal end thereof as illustrated in FIG. 55A. The distal end portion 282a of the strip 282 is bent upwards.

As FIG. 53C shows, the cover 290 is a hollow cylinder having a slit 291 extending from end to end. The cover 290 therefore has a C-shaped cross section. The slit 291 is long enough to receive the entire strip 282 of the case 280. The cover 290 has a connecting portion 292 at the proximal end. The portion 292 can be fastened to the distal end portion of the body 281 by means of, for example, adhesive or screws.

It will be explained how the ligature 212 is set on the ligature holding section 271. The ligature 212 is mounted on the section 271, with the ligature holder 270 inserted in the case 280 as illustrated in FIG. 55A. As shown in FIGS. 57A and 57B and FIGS. 58A and 58B which are enlarged views, a ligature holding member 295 can be fitted in the proximal end of the helical groove 273 cut in the outer circumferential surface of the ligature holding section 271. Connected to the member 295 is one end portion of the ligature 212. As shown in FIG. 58A, the ligature holding member 295 has a small hole 295a and a large hole 295b. The small hole 295a can hold the ligature 212, whereas the large hole 295b can allow the passage of the strip 282 of the case 280. The member 295 is fitted in the proximal end of the helical groove 273 as long as the strip 282 passes through the large hole 295b.

Figure 56A:
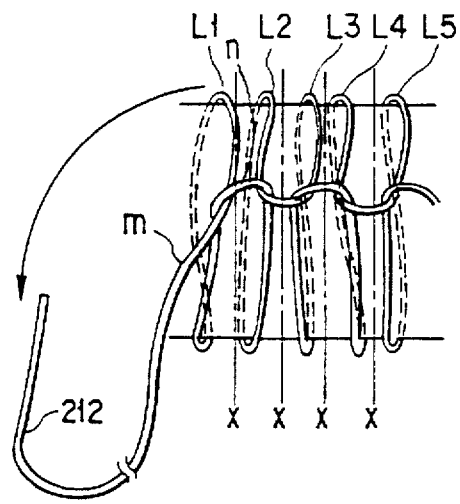
FIGS. 56A to 56C are diagrams explaining how to release the loops of a ligature, one by one.

As shown in FIG. 56A, the ligature 212 is wound around the ligature holding section 271 and the elongated strip 282, passing through the helical groove 273 and binding the section 271 and the strip 282 together. More correctly, the ligature 212 is wound once, passing through the first turn of the groove 273, thus forming a first loop $L_1$. The end portions m and n of the first loop $L_1$ are crossed. Then, the portion of the ligature 212, which extends from the end portion n of the first loop $L_1$ is wound once around the ligature holding section 271 and the elongated strip 282, forming a second loop $L_2$. The end portion n' of the second loop $L_2$ is crossed over the end portion n of the first loop $L_1$. The first loop $L_1$ and the second loop $L_2$ are therefore symmetric with respect to point x. The ligature 212 is repeatedly wound around the section 271 and the strip 282 in the same manner, thereby forming other loops $L_3$, $L_4$, $L_5$, . . . .

As seen from FIGS. 57A and 57B and FIGS. 58A and 58B, the loops $L_1$, $L_2$, . . . , thus formed, are set in the turns $M_1$, $M_2$, . . . of the helical groove 273, except those portions which pass over the elongated strip 282. For example, the loops $L_1$ and $L_2$ are set in the turns $M_1$ and $M_2$ of the groove 273, and the crossing portion 299 of the ligature 212, which connects the loops $L_1$ and $L_2$, passes over the elongated strip 282 and is set neither in the turn $M_1$ nor $M_2$ of the groove 273.

Figure 56B:
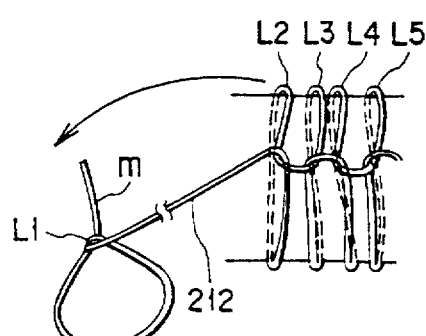
Figure 56C:
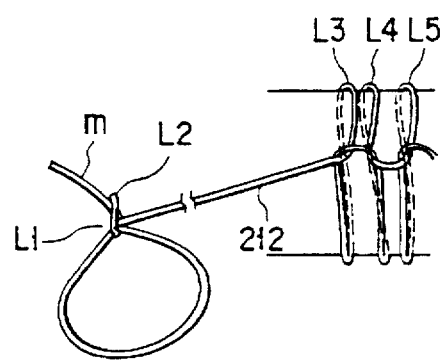

The loop $L_1$ is released rom the ligature holding section 271, and the free end portion m of the ligature 212 is passed through the loop $L_1$, as is illustrated in FIG. 56B. The free end portion m of the ligature 212 is then pulled, whereby the loop $L_1$ is tightened, ultimately forming a first knot. Further, the loop $L_2$ is released rom the ligature holding section 271, and the free end portion m of the ligature 212 is passed through the loop $L_2$, as is illustrated in FIG. 56C. The free end portion m is pulled, whereby the loop $L_2$ is tightened, forming a second knot on the first knot. Since the loops $L_1$ and $L_2$ have been formed by winding the ligature 212 in the opposite directions, the knots constitute a so-called "square knot," which is tight and firm. To form additional knots, it suffices to release the loops $L_3$, $L_4$, $L_5$, . . . from the ligature holding section 271, to pass the free end portion m of the ligature 212 through the loop $L_1$ and to pull the free end portion m.

In order to ligate a tissue (not shown) after two knots have been formed on the free end portion m of the ligature 212, which is wrapped around the tissue, the surgeon needs only to cut the free end portion m and to apply the remaining portion of the ligature 212 to the tissue.

When the loop $L_1$ is released from the ligature holding section 271 as shown in FIG. 56B, the loop $L_2$ remains wound around the section 271. Therefore, a knot is formed on only the loop $L_1$ when the free end portion m of the ligature 212 is pulled.

How to assemble the ligating apparatus 210 will be explained. First, the main body 250 of the cartridge section 210b is assembled as shown in FIG. 55B. The elongated strip 282 and the crossing portions 299 of the ligature 212 are held in the slit 291 of the cover 290. Then, the operation section 217 is coupled to the forceps 213 as shown in FIG. 51B, and the shaft 222 of the forceps 213 is inserted into the main body 250 from the proximal end of the main body 250. The latching part 284 of the body 281 is thereby set in engagement with the latch 228 of the operation section 217. At this time, the arm 229 of the forceps 213 is fitted into the slit 283 of the body 281. The cam pin 230 projecting from the distal end of the arm 229 fits into the cam groove 274 made in the proximal portion 272 of the ligature holder 270.

Next, the forceps 213 and the cartridge section 210b coupled to the forceps 213 are inserted into the sheath 215 from the proximal end thereof, until the sheath 215 covers the cartridge section 210b. The pin 226 protruding from the hollow cylinder 225 is fitted into the L-shaped slit 221 of the base 220, preventing the forceps 213 from rotating with respect to the sheath 215. The pin 226 is biased onto the end of the slit 221 by a bias means such as a spring. Therefore, the forceps 213 cannot easily be released from the sheath 215. An airtight space is provided in the sheath 215 by the seals (e.g., rubber packings or O-rings) interposed between the base 220 and the hollow cylinder 225.

The inner diameter of the sheath 215 is slightly greater than the outer diameter of the latching part 284 of the body 281. Hence, the latching part 284 would not come out of engagement with the latch 228 once the sheath 215 has been mounted on the cartridge section 210b.

As long as the ligature holding section 271 remains sufficiently pushed forward together with the main body 250 of the cartridge section 210b, the cam pin 230 remains at the position b in the cam groove 274 of the ligature holder 270 (a component of the main body 250), and the distal end portion of the forceps 213 remains pulled into the main body 250. In other words, the distance between the cam pin 230 and the distal end of the forceps 213 is equal to or shorter than the distance between the position b and the distal end of the main body 250.

Figure 54:
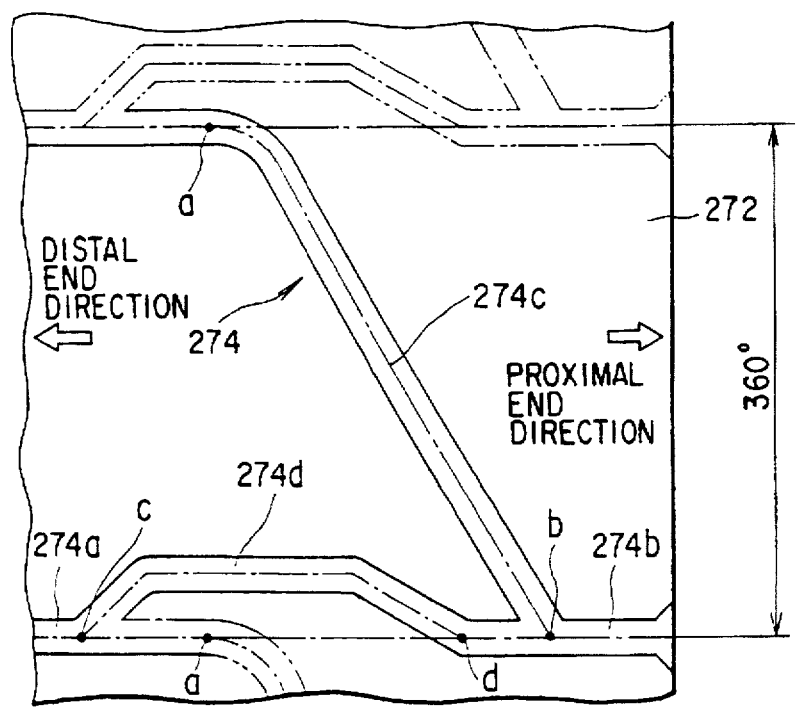
FIG. 54 is a developed view of the cam groove as seen along arrow B shown in FIG. 53A.

When the operation section 217 is pulled, the main body 250 connected to the section 217 is moved back. As a result, the cam pin 230 moves along the cam groove 274, from the point b (FIG. 54) to the first straight portion 274a, passing the distal end d of the second straight portion 274b, the bypass portion 274d and the point c (FIG. 54). While the cam pin 230 is moving from the point d to point c in the cam groove 274, the ligature holder 270 rotates a little. Nonetheless, the holder 270 rotates to the initial position when the cam pin 230 reaches the point c in the groove 274. The wound state of the ligature 212 is restored.

As the main body 250 of the cartridge section 210b is pulled back, the forceps 213 gradually projects from the distal end of the main body 250. The distance the forceps 213 so projects when the main body 250 is pulled to the very proximal end of the shaft 222 is equal to or greater than the developed length of each loop L of the ligature, set in one turn M of the helical groove 273. Preferably, this distance is the sum of the length of the free end portion of the ligature 212 (not wound around the ligature holding section 271) and the total length of three or four loops L to be released from the ligature holding section 271 one after another. In the present embodiment, the distance is equal to or greater than the total length of four loops. The free end portion of the ligature 212 should be long enough to be wrapped around the tissue of interest and held at the distal end by the tongs 223 of the forceps 213. Needless to say, it must not be too long.

With reference to FIGS. 59A and 59B, FIGS. 60A and 60B, FIGS. 61A and 61B, FIGS. 62A to 62C, and FIGS. 63 and 64, it will be explained how a surgeon operates the ligating apparatus 210 to ligate a tubular tissue present in a patient's body cavity.

To ligate a blood vessel 300, for example, present in the body cavity, the surgeon first pulls back the main body 250 of the cartridge section 210b until the cam pin 230 slides to the first straight portion 274a of the cam groove 274. He or she then inserts the distal end portion of the apparatus 210 into the body cavity through, for example, the trocar set in an opening incised in the body wall. The distal end of the forceps 213 protruding from the main body 250 is thereby located near the blood vessel 300. Next, the surgeon manipulates the forceps 213, ablating the blood vessel 300 from the neighboring tissues, wrapping the free end portion of the ligature 212 around the blood vessel 300, and holding the free end of the ligature 212 between the tongs 223 of the forceps 213—as is illustrated in FIGS. 59A and 59B. The forceps 213 is a Kelly forceps, and the surgeon can perform the continuous sequence of surgical steps, i.e., the ablation of the blood vessel 300, the application of the ligature 212 and the holding of the ligature 212. Nonetheless, he or she may use any other type of a forceps, instead of the Kelly forceps 213.

Thereafter, the surgeon pushes the handle 297 connected to the proximal end of the operation section 217, moving forward the main body 250 of the cartridge section 210a, as shown in FIGS. 60A and 60B. The cam pin 230 slides along the cam groove 274, from the first straight portion 374a to the helical portion 274c. The cam pin 230 then moves along the helical portion 274c, rotating the ligature holder 270 in the case 280. Thus rotated, the ligature holder 270 pushes the loops L of the ligature 212, set in the helical groove 273 cut in the circumferential surface of the ligature holding section 271. This is because the helical groove 273 and the helical portion 274c of the cam groove 274 are turned in the opposite direction, also because the ligature 212 is wound around not only the ligature holding section 271 but also the elongated strip 282, and further because the crossing portions 299 of the ligature 212 are held in the slit 291 of the cover 290. If the ligature holder 270 rotates, the crossing portions 299 will abut on the edge of the cover 290, inhibiting the ligature 212 from rotating. The elongated strip 282 also serves to prevent the ligature 212 from rotating. Thus, when the ligature holder 270 rotates, the loops L are pushed forward but not rotated at all.

Therefore, as the ligature holder 270 rotates, the first loop $L_1$ is gradually released from the ligature holding section 271. Simultaneously, the other loops $L_2$, $L_3$, . . . and the ligature holding member 295 are moved forward along the helical groove 273. When the cam pin 230 reaches the point b in the cam groove 273 and the ligature holder 270 is rotated 360° about its axis, the loop $L_1$ is completely released from the ligature holding section 271 as shown in FIG. 61A and 61B. This allows the other loops $L_2$, $L_3$, to move further forward to the turns $M_1$, $M_2$, . . . of the helical groove 273, respectively. At this time, the tongs 223 of the forceps 213 are pulled completely into the ligature holder 270. Held by the tongs 223, the free end portion of the ligature 212 is passed through the loop $L_1$ as shown in FIGS. 61A and 61B.

Then, the surgeon pulls the handle 297 secured to the proximal end of the operation section 217, moving back the main body 250 of the cartridge section 210a, as shown in FIG. 62A. The forceps 213 is thereby projected from the distal end of the main body 250. Now that the loop $L_1$ is located in front of the forceps 213, one portion of the ligature 212, held by the tongs 223 and extending from the loop $L_1$, is pulled forward. The surgeon then pulls the handle 297 further back, pulling the other portion of the ligature 212, which extends from the loop $L_1$. As a result of this, the portions of the ligature 212, extending from the loop $L_1$, are pulled in the opposite direction, whereby the loop $L_1$ tightens the blood vessel 300 and a knot is formed on the ligature 212 as shown in FIG. 62A.

As the main body 250 of the cartridge section 210a is pulled back to tighten the loop $L_1$, the cam pin 230 moves from the point b in the cam groove 274 to the bypass portion 274b of the cam groove 274. The ligature holder 270 is therefore slightly rotated in one direction as illustrated in FIG. 62B. However, the holder 270 is slightly rotated in the opposite direction as shown in FIG. 62C when the cam pin 230 reaches the point c in the cam groove 274, i.e., the initial position. The condition in which the loops L is set in the helical groove 273 remains unchanged. That is, the ligature holder 270 rotates while moving forwards, but does not rotate while moving backwards. The loop L set in the foremost turn M of the helical groove 273 would not be moved back, remaining at the distal end of the ligature holding section 271.

Next, the surgeon pushes the handle 297 forward again, while holding the free end of the ligature 212 between the tongs 223, thereby moving the main body 250 forward. The second loop $L_2$ is thereby released from the ligature holding section 271 as shown in FIG. 63. The surgeon then pulls the handle 297 backwards. The second loop $L_2$ is tightened, forming a second knot, as illustrated in FIG. 64. The two knots constitute a square knot, which is tight and firm. To form other knots to ligate the blood vessel 300 more firmly, the surgeon only needs to repeatedly operate the ligating apparatus 210 in the same way as described above. The more loops L have been released from the ligature holding section 271, the longer is the distance the main body 250 must be pulled back with respect to the forceps 213 to tighten the last released loop L. In spite of this, the knots do not move at all with respect to the forceps 213, and the distance the forceps 213 is pushed forward with respect to the knots does not change at all.

In the eighth embodiment, the stroke of the forceps 213 is about four times the length of each loop, and at most four knots can be formed on the ligature 212. If the free end portion of the ligature 212 is too long, or if five or more knots are formed, the stroke of the forceps 213 will be too short to tighten the loops L. In this case, it suffices for the surgeon to pull the proximal end portion of the ligature 212 by means of another forceps inserted into the body cavity.

Having ligated the blood vessel 300, the surgeon cuts both end portions of the ligature 212 from the knots. To ligate the blood vessel 300 at any other part, or to ligate any other neighboring tissue, the surgeon needs only to repeat the above-mentioned sequence of ligating steps. At this time, that portion of the ligature 212 which is connected to the cartridge is used as a free end portion of the ligature 212. He or she may repeat ligation so long as any loops L remain in the helical groove 273. Since the tongs 223 are curved at distal end, the ligature holding member 295 is prevented from slipping out of the elongated strip 282, and the loops L can therefore be used to the last one. The last loop L can be tightened as firmly as any other loop since the member 295 holds a portion of the ligature 213 extending from the loop L. Additionally, the loops L on the ligature holding section 271 can be seen through the slit 291 cut in the cover 290. How many loops L remain on the section 271 can be more easily recognized if the cover 290 is made of transparent material.

The tissue to be ligated may exist at a deep position in the body cavity or may be located in front of an organ. It is then impossible for the surgeon to push the forceps 213 enough to form a sufficiently tight knot. How to tighten the knot adequately in such a case will be explained, with reference to FIGS. 101A and 101B.

Figure 101A:
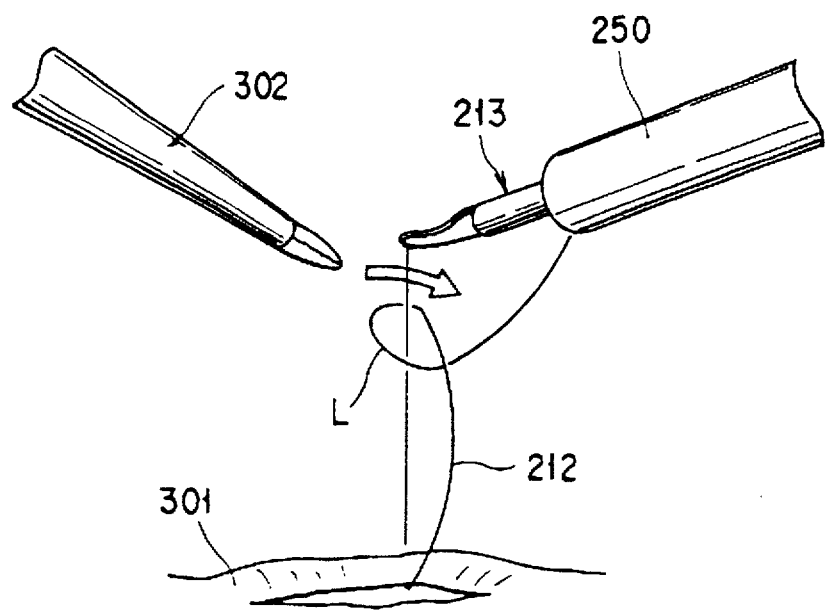
FIGS. 101A and 101B are diagrams explaining a method of ligating a tissue.
Figure 101B:
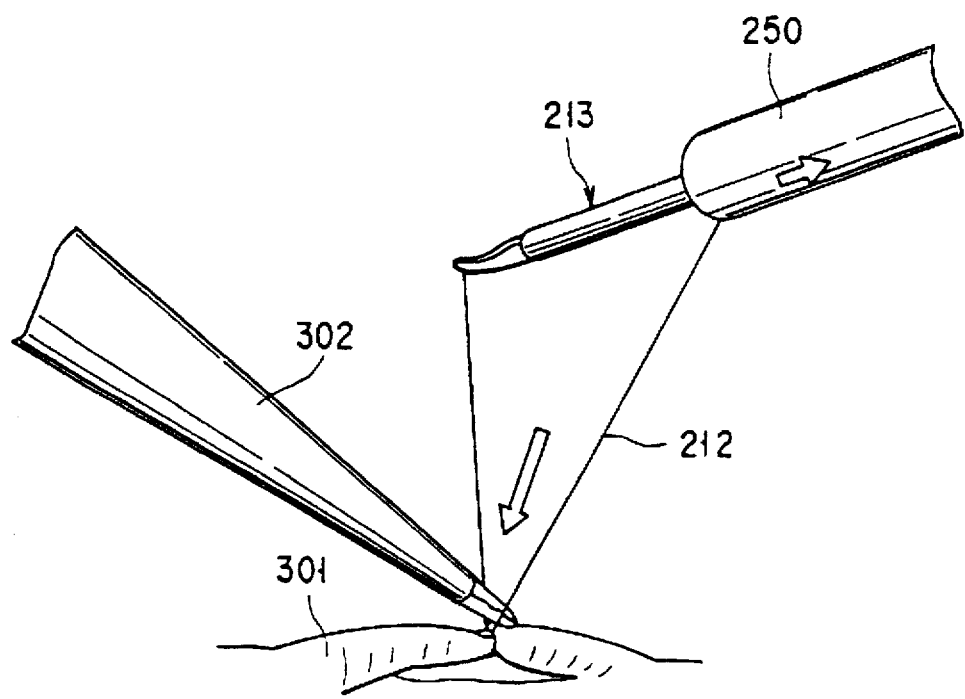

As seen from FIG. 101A, the surgeon first passes the ligature 212 under the tissue 301. The surgeon then pushes forward the main body 250 of the cartridge section 210a, while holding the free end of the ligature 212. The first loop L is thereby released from the ligature holding section 271. At this time, the surgeon sets the distal end portion of another forceps 302 inserted in the body cavity, in the space among the free end portion of the ligature 212, the first loop L released and the fixed end portion of the ligature 212. Then, the surgeon pulls the main body 250 back as shown in FIG. 101B, moving the forceps 302 toward the tissue 301 and, thus, applying a tension on both end portions of the ligature 212. The crossing portion of the ligature 212 is therefore lowered toward the tissue 301. The first loop L is closed, squeezing the tissue 302, and a first knot is formed on the ligature 212. If the surgeon is unable to pull the free end portion of the ligature 212 sufficiently, he or she pulls the main body 250 further back, while holding the first knot with the forceps 302. A sufficient tension is therefore applied on the first knot, making the knot firm and tight. A second, a third knot, and so on can be made on the ligature in the same way as the first knot.

The ligating apparatus 210 according to the eighth embodiment is advantageous in the following respects:

(1) The surgeon can ligate a tissue at two or more parts or a plurality of tissues.

(2) As many knots as desired can be formed, one upon another.

(3) The surgeon can easily and readily perform ligation of the type conducted in the ordinary surgical operation. The tissue can be ligated firmly since knots are made one by one as in the ordinary celiotomy.

(4) The loops L can be continuously released from the ligature holding section 271, one after another.

(5) The loops L can be used to the last, for three reasons. First, the ligature 212 is secured at the proximal end to the ligature holding member 295. Second, the member 295 is pulled forward together with the foremost loop L, along the helical groove 273. Third, bent upwards, the distal end portion 282a of the elongated strip 282 prevents the member 295 from slipping from the elongated strip 282.

(6) The cartridge section 210a can easily be replaced with a new one, after it has been used.

(7) The surgeon can perform ligation, merely by moving the forceps 213 and the main body 250 relatively to each other.

(8) If the free end portion of the ligature 212 is cut during the ligation procedure or is too short to go around the tissue, the ligature can be replenished only by pulling back the main body 250 to release a loop L from the ligature holding section 271. To replenish ligature it is unnecessary to pull the ligature 212 from the ligature holding section 271 by using the tongs 223 of the forceps 213.

(9) Its interior sealed in airtight fashion from the outside, the apparatus 210 can be employed in pneumoperitoneal operations.

(10) Since the sheath 215 covers the latch 228 and the latching part 284, the latching part 284 would not come out of engagement with the latch 228 even if a great force is exerted on the apparatus 210 during the ligation procedure.

(11) The distal end portion of the apparatus 210 can be smoothly inserted into the body cavity since the main body 250 of the cartridge section 210a remains in the sheath 215 no matter whether the main body 250 is pushed forward or pulled backwards.

(12) Similar in shape and function to ordinary forceps, the forceps 213 can be used to carry out surgical work other than ligation.

(13) Covered by the cover 290, the loops L of the ligature 212 would not entangle with one another when the distal end portion of the apparatus 210 is inserted into the body cavity. Further, the ligature 212 would not be released in its entirety or get twisted, because it is fastened at its proximal end to the ligature holding member 295.

(14) The ligature holder 270 can be smoothly rotated since the cover 290 prevents the ligature 212 from moving.

(15) Any knot on the ligature 212 can be tightened adequately, without pulling the tissue in one direction, because both portions extending from the knot are pulled in the opposite directions by moving the forceps 213 and the main body 250 in the opposite directions.

(16) If the first knot is formed by pushing the forceps 213 by the shortest distance possible, the forceps 213 would not damage an organ, if any, located in front of it, when it is pushed to form a second knot on the first knot. This is because the distance the forceps 213 is pushed to form the second knot is equal to that shortest distance.

(17) The surgeon can know how many loops L remain on the ligature holding section 271 since the loops L can be well seen through the slit 291 cut in the cover 290.

(18) The loops L on the ligature holding section 271 serve to hold to the main body 250 the last loop L released from the section 271. This helps to close the loop L last released, forming a tight knot, as the main body 250 is pulled backwards.

(19) The components of the apparatus 210 have such lengths that a loop L of the ligature 212 is not released from the section 271 before the forceps 213 is pulled into the main body 250 of the cartridge section 210a. The loop L released from the section 271 will not be mounted on the forceps 213, making it easy for the surgeon to pass the free end portion of the ligature 212 through the released loop L.

(20) The elongated strip 282 is located in the slit 291 of the cover 290, together with the ligature holding section 271. Thus, the strip 282 prevents the ligature 212 from slipping into the gap between the ligature holder 270 and the cover 290 even if the ligature 212 is relatively thin. To state it in another way, the elongated strip 282 serves to prevent the ligature 212 from moving.

The above-mentioned advantages of the eighth embodiment will become more apparent when the ligating apparatus 210 is compared with those disclosed in U.S. Pat. Nos. 3,871,138, 5,391,176 and 5,312,423.

First, the ligating apparatus disclosed in U.S. Pat. No. 3,871,138 will be first described as to its structure and operation.

The apparatus of U.S. Pat. No. 3,871,138 is designed so as to ligate a tissue with 8-shaped ligature rings. Each ring consists of two loops. The second loops of the rings are set in the helical groove cut in the outer circumferential surface of a hollow cylindrical cartridge. The first loops of the 8-shaped ligature rings are mounted on a rod extending parallel to the cartridge. The rod has a hook at the distal end, for catching and pulling the first loop of any ligature ring released from the cartridge. A forceps passes through the cartridge and can move back and forth. The forceps has a helical cam groove in its outer circumferential surface. The cartridge has a cam pin protruding from its inner circumferential surface and loosely fitted in the cam groove of the forceps.

As the forceps is moved forward, the cartridge is rotated in one direction around its axis, moving the second loops of the ligature rings forward. The 8-shaped ligature rings are therefore released from the cartridge one after another. When the first loop of any ring released is pulled by means of the hook, the second loop is closed or squeezed, forming a knot.

The ligating apparatus of U.S. Pat. No. 3,871,138 is operated in the following manner, to ligate a tissue present in a patient's body cavity.

The surgeon first manipulates the forceps, holding the tissue and then pushes the cartridge forward, pulling the tissue into the cartridge. When the cartridge is pushed relative to the forceps, it is rotated. The second loop of at least one 8-shaped ligature ring is thereby released from the cartridge and mounted onto the tissue. Simultaneously, the first loop of the ring is caught by the hook provided at the distal end of the rod. The surgeon pulls the rod, thereby pulling the first loop of the ring and, as a result, the second loop of the ligature ring is squeezed, ligating the tissue.

The ligating apparatus disclosed U.S. Pat. No. 3,871,138 has the following drawbacks:

(1) Designed to ligate the severed end of a tubular or flat tissue, the apparatus cannot enable the surgeon to ablate a tubular tissue from the neighboring tissues or pass a ligature under the tissue ablated.

(2) Each of the ligature rings mounted on the cartridge is used to ligate a tissue, forming only one knot, not as many knots as the surgeon wishes to ligate the tissue more firmly.

(3) To squeeze the first loop of each 8-shaped ligature ring, the surgeon needs not only to manipulate the rod having the hook at the distal end and the tongs of the forceps, but also to move the cartridge back and forth.

The ligating apparatus 210 according to the invention has none of the above-mentioned drawbacks inherent in the apparatus disclosed in U.S. Pat. No. 3,871,138. This is because the apparatus 210 is different from the ligating apparatus of the U.S. patent, on the following points:

(1) The forceps 213 is provided to hold the free end portion of the ligature 212, extending from the foremost of the loops L mounted on the ligature holding section 271, whereas in the apparatus of the U.S. patent the forceps is used to hold the tissue to be ligated. The can also ablate a tubular tissue and pass the ligature 212 under the tissue. Any ligature ring mounted on the cartridge of the apparatus disclosed in the U.S. patent has no free end portion which the forceps may hold.

(2) Even after released from the main body 250, any loop L is connected to the next one still mounted on the section 271 since several means are provided, each for releasing one loop L. The loops L on the section 271 can be released one after another, merely by pulling the free end of the ligature. Hence, two or more knots can be formed one upon another, to ligate a tissue more firmly than otherwise. Further, after both portions extending from the knot formed last are cut, the surgeon can manipulate the forceps 213, holding the new free end of the ligature 212, thereby to ligate another part of the tissue or another tissue present in the body cavity. With the apparatus of the U.S. patent it is impossible to form two more knots on each ligature ring.

(3) The apparatus 210 enables the surgeon to perform a ligation in the same way as in the ordinary surgical operation, only by moving the forceps 213 and the main body 250 relative to each other. The surgeon needs to conduct more intricate surgical work to ligate a tissue by using the apparatus disclosed in the U.S. patent.

(4) The apparatus 210 has the cover 280, which covers the ligature holding section 271, preventing the loops L on the section 271 from entangling. Further, the slit 291 of the cover 290 restricts the motion of the loops L since the crossing portions 299 of each loop L are held in the slip 291. Obviously, the slit 291 differs in function from the rod used in the ligating apparatus of the U.S. patent.

(5) The interior of the apparatus 210 is sealed in airtight fashion from the outside. Shaped like a tube, the distal end portion of the apparatus 210 can be smoothly inserted into the body cavity via a trocar. In contrast, the distal end portion of the ligating apparatus of the U.S. patent is not so shaped.

Now, the ligating apparatus disclosed in U.S. Pat. No. 5,391,176 will be first described as to its structure and operation, in comparison with the ligating apparatus 210 which is the eighth embodiment of this invention.

The apparatus of U.S. Pat. No. 5,391,176 is designed to help surgeons to ligate a tissue in an endoscopic or laparoscopic operation, in the same manner as in the ordinary surgical operation. The apparatus has a rod having a slot in the distal end. A ligature is wound around the rod, forming loops. This apparatus is operated in the following way, to ligate a tissue present in a patient's body cavity.

At first, the surgeon inserts the distal end portion of the apparatus into the body cavity. He or she then manipulates a forceps inserted into the body cavity, holding the free end of the ligature extending from the first loop, passing it under the tissue, and guiding it through the slot of the rod. Thereafter, the surgeon operates another forceps inserted in the body cavity, holding the free end portion of the ligature, passing it through the first loop, and pulling it to release the loop from the rod.

The ligating apparatus disclosed U.S. Pat. No. 5,391,176 has the following drawbacks:

(1) Two forceps, neither being a component of the apparatus, must be manipulated to ligate a tissue. More precisely, the first forceps is used to wrap the ligature around the tissue and pass it through the slot, and the second forceps to hold the free end portion of the ligature, pass it through the first loop, and pull it to release the loop from the rod. It is cumbersome for the surgeon to manipulate one forceps after the other. The surgeon requires much skill to manipulate two forceps, while looking at a TV monitor displaying a two-dimensional image of the interior of the body cavity.

(2) When a loop is released from the rod, the next loop is located not at the distal end of the rod, but far back on the rod. The more loops have been released, the more difficult it is for the surgeon to pass the free end portion of the ligature through the next loop to be released from the rod.

(3) Not covered at all, the loops on the rod may be caught by projections or unnecessarily released from the rod as the distal end portion of the apparatus is inserted into the body cavity through a narrow opening incised in the body wall.

(4) The loops on the rod may move, failing to keep distance form one another. If one loop contacts any adjacent one, it becomes difficult for the surgeon to pass the free end portion of the ligature through the loop.

The ligating apparatus 210 according to this invention has none of the drawbacks inherent in the apparatus disclosed in U.S. Pat. No. 5,391,176, because it is different therefrom in the following respects:

(1) The apparatus 210 enables the surgeon to perform ligation in the same way as in the ordinary surgical operation, only by moving the forceps 213 and the main body 250 relative to each other. The apparatus 210 is much easier to manipulate than the apparatus of U.S. Pat. No. 5,391,176.

(2) As soon as any loop L is released from the ligature holding section 271, the next loop L is located at the distal end of the section 271. This facilitates the ligation of the tissue. Any loop released will fall over the free end portion of the ligature, provided the free end portion is held by the forceps. The free end portion can therefore be passed easily through the loop.

(3) The loops L on the section 271 would not slip from the ligature holding section 271 or entangle since the cover 290 covers the section 271 during the ligation.

(4) The loops L on the section 271 would not move to contact one another since they are set in the turns of the helical groove 273, respectively.

Having the features described above, the ligating apparatus 210 is obviously advantageous over the ligating apparatus disclosed in the U.S. Pat. No. 5,312,423, which has the aforementioned drawbacks.

FIGS. 102A to 102C illustrate a first modification of the eighth embodiment described above. As seen from FIGS. 102A to 102C, the modified apparatus has no component which, like the elongated strip 282, prevents the ligature 212 from moving on the ligature holding section 271. Without a component like the strip 282, the ligature 212 is well prevented from moving since the crossing portions 299 of each loop L abut on the edge of the cover 290 which has the slit 291.

As shown in FIGS. 102B and 102C, the ligature holding member 295 has substantially the same width as the slit 291 cut in the cover 290 and has no hole equivalent to the large hole 295b which allows the passage of the elongated strip 282. The ligature holding member 295 is thin enough to be received in the helical groove 273. That portion of the member 295 which is set in the groove 273 is broader than the slit 291. As shown in FIG. 102C, the slit 291 has a narrowed part 310 at the distal end. It is desirable that the ligature be too thick to slip into the gap between the ligature holder 270 and the cover 290.

Due to the narrowed part 310 of the slit 291, the ligature holding member 295 would not move from helical groove 273 or the slit 291. Therefore, the loops L can be used to the last. Since the elongated strip 282 is not used, it is easier to wind the ligature 212 around the section 271 and to set in the helical groove 273. For the same reason, the cover 290 can be thinner by the thickness of the strip 282. The cover 290 and, ultimately, the main body 250 of the cartridge section 210a can have a reduced outer diameter. The distal end portion of the apparatus can therefore be smoothly inserted into a body cavity.

The modified ligating apparatus (FIGS. 102A to 102C), as well as the first to eighth embodiments, can be used to suture a tissue, provided that a sutural needle is connected to the free end of the ligature 212.

Figure 65:
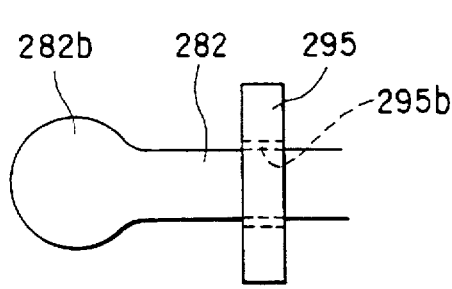
FIG. 65 is a bottom view showing a modification of the eighth embodiment.

FIG. 65 shows a second modification of the eighth embodiment, which is characterized in that the strip 282 has a thick distal end 282b, not a distal end bent upwards. The distal end 282b is larger than the large hole 295b of the ligature holding member 295. Thus, the strip 282, but not the distal end 282b, can pass through the large hole 295b. The distal end 282b prevents unnecessary release of the loops L from the ligature holding section 271. The loops L can therefore be used to the last one.

Figure 66:
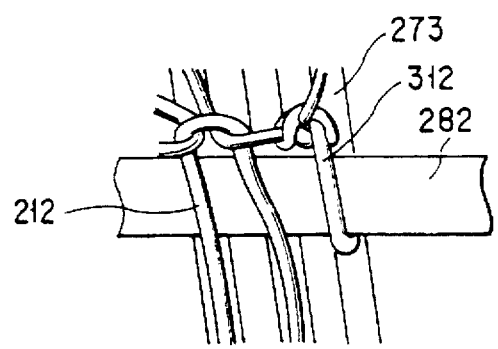
FIG. 66 is a bottom view illustrating another modification of the eighth embodiment.

FIG. 66 shows a third modification of the eighth embodiment. The third modification is characterized in that a loop 312 is made at the proximal end of the ligature 212 and that the elongated strip 282 passes through this loop 312. The loop 312 performs a function similar to that of the ligature holding member 295.

A ligating apparatus according to the ninth embodiment of the present invention will be described, with reference to FIGS. 67A to 67D and FIGS. 68 to 71.

Figure 70:
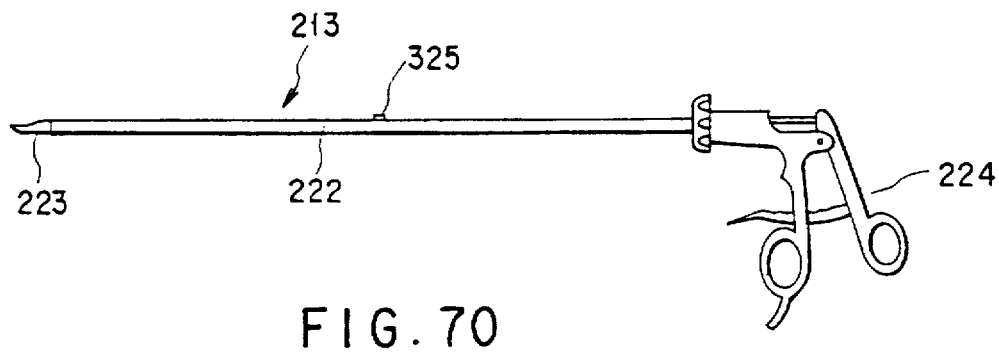
FIG. 70 is a side view of the forceps incorporated in the ninth embodiment.

The ligating apparatus of this embodiment comprises a cartridge 250a shown in FIGS. 67A to 67D and FIG. 68 and a forceps 213 shown in FIG. 70. The cartridge 250a comprises a ligature holder 270a, a case 280a and a cover 290a, which are shown in FIGS. 67B, 67C and 67D, respectively.

Figure 69:
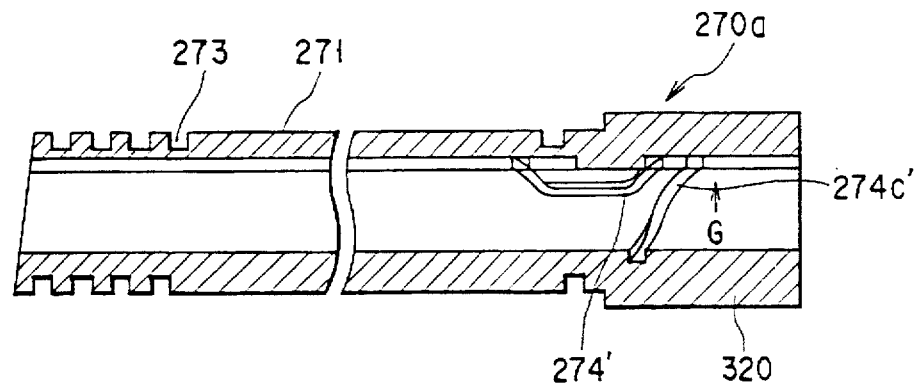
FIG. 69 is a sectional side view of the ligature holder of the ninth embodiment.

As shown in FIG. 67B, the ligature holder 270a is a hollow cylinder through which the shaft 222 of the forceps 213 can pass. The ligature holder 270a is comprised of a ligature holding section 271 and a thick rotatable section 320. The rotatable section 320 is far shorter than the ligature holding section 271 and coupled to the proximal end thereof. The section 271 has a helical groove 273 formed in its circumferential surface. A ligature 212 is wound around the section 271, forming loops set in the turns of the groove 273 as in the eighth embodiment. As shown in FIG. 69, a cam groove 274' is cut in the inner circumferential surface of the ligature holder 270a. When developed, the cam groove 274' looks symmetrical to the cam groove 274 illustrated in FIG. 54. The helical portion 274'c of the cam groove 274' and the helical groove 273 are turned in the opposite directions, as in the eighth embodiment.

As seen from FIG. 67C, the case 280a comprises a hollow cylinder 323 and an elongated strip 282. The strip 282 extends from the distal end of the cylinder 323 and is identical in shape to its counterpart of the eighth embodiment. The proximal end of the cylinder 323 is closed by a cover 321. When the cover 321 is removed from the cylinder 323, the cylinder 323 allows the passage of the ligature holding section 271 of the ligature holder 270a and can contain the rotatable section 320 thereof. The strip 282 is so long that its distal end portion projects from the ligature holding section 271 once after the ligature holder 270a and the case 280a have been combined together. The distal end portion of the strip 282 is bent upwards. The cover 321 has a forceps guiding hole 322 which communicates with the axial hole of the ligature holder 270a. The hole 322 has a diameter slightly larger than the outer diameter of the shaft 222 of the forceps 213. Hence, the shaft 222 can be passed through the hole 322 though a cam pin 325 protrudes from the shaft 222 in the radial direction thereof. A seal (not shown) is interposed between the shaft 222 and the hole 322 of the cover 321, rendering the hollow cylinder 323 airtight from the outside. The cover 321 may be secured to the cylinder 323 by means of screws, adhesive or welding.

As shown in FIG. 67D, the cover 290a has the same shape as its counterpart of the eighth embodiment. The cover 290a has its proximal end portion fitted in the hollow cylinder 323 of the case 280a. The cover 290a may be fastened to the case 280a by means of adhesive or screws.

As may be understood from FIG. 70, the forceps 213 is almost identical to its counterpart of the eighth embodiment. The cam pin 325 protrudes from the middle part of the shaft 222 of the forceps 213. The cam pin 325 is loosely fitted in the cam groove 274' cut in the inner circumferential surface of the ligature holder 270a. The pin 325 is spaced apart from the distal end of the forceps 213 by a distance either equal to or shorter than the distance between the distal end of the ligature holder 270a and the point b in the cam groove 274'. The cam pin 325 is spaced from the proximal end of the shaft 222, by a distance shorter than the ligature holder 270a.

To use the ligating apparatus according to the ninth embodiment, a surgeon inserts the forceps 213 into the cartridge 250a from the proximal end thereof. The surgeon then inserts the distal end portion of the apparatus into a patient's body cavity, as shown in FIG. 71, through a trocar 330 set in an opening incised in the body wall 331. At this time, the cam pin 325 is fitted in the cam groove 274' cut in the inner surface of the ligature holder 270a. Thereafter, the surgeon manipulates the cartridge 250 while holding the hollow cylinder 323 of the case 280a, exactly in the same way as in the case of the eighth embodiment.

The ninth embodiment attains the same advantages as the eighth embodiment and the following additional advantages:

(1) Since the cam groove 274' is cut in the inner surface of the ligature holder 270a, the helical groove 273 extends over almost the entire length of the holder 270a. More loops L of ligature can be mounted on the holder 270a than in the case of the eighth embodiment.

(2) Since the surgeon holds the operation section 224 of the forceps 213 in one hand, while holding the hollow cylinder 323 of the case 280a in the other hand, he or she can well know how tight he or she is pulling the ligature 212 at both ends.

(3) The cartridge 250 includes the operation section 224. This makes it easy to insert the forceps 213 into the cartridge 250 and to pull it from the cartridge 250. Since the cartridge is a throw-away type, only the forceps 213 needs to be washed after use.

FIGS. 72A to 72C and FIG. 73 show a ligating apparatus according to the tenth embodiment of the present invention. The tenth embodiment is identical to the eighth embodiment, except that the ligature holder 270 is rotated by electric means. Therefore, the components similar or identical to those of the eighth embodiment are designated at the same reference numerals and will not be described in detail.

The ligating apparatus according to the tenth embodiment has a forceps section and a cartridge section. The forceps section comprises a sheath 215 and a forceps 213 which are shown in FIGS. 72A and 72C, respectively. The cartridge section comprises a cartridge operating section 217 and a cartridge body 250 which are shown in FIGS. 72C and 72B, respectively. The cartridge body 250 has a case 280b. The case 280b is a combination of the case 280 and the cover 290, both used in the eighth embodiment. The cartridge operating section 217 has a hollow cylinder 288 which is fitted in the proximal end 284 of the case 280b. The hollow cylinder 288 has a gear 340 on the front. The gear 340 is connected to a driver 346, which is controlled by a controller 347 and which is, for example, an ultrasonic motor. The gear 340 is in mesh with the gear 345 provided at the proximal end of the ligature holder 270. Thus, the ligature holder 270 is rotated when the driver 346 is operated by the controller 347.

A power supply switch 341 is provided on the operation section 224 of the forceps 213, and a power supply 342 is provided in the operation section 224. The switch 341 is closed when the handle 297 of the cartridge operating section 217 is pushed to its foremost position and abuts on the switch 341 as shown in FIG. 73. Once the switch 341 is closed, electric power is supplied from the power supply 342 to the driver 346 via the operation rod 227 incorporated in the cartridge operating section 217. The driver 346 drives the gear 340 under the control of the controller 347. The ligature holder 270 is thereby rotated.

To use the ligating apparatus according to the tenth embodiment, a surgeon first inserts the forceps 213 into the cartridge body 250. When the proximal end 284 of the case 280b is set into engagement with the hollow cylinder 288 of the cartridge operating section 217, the gear 345 provided on the ligature holder 270 comes into mesh with the gear 340 provided on hollow cylinder 288. The surgeon then inserts the distal end portion of the apparatus into a patient's body cavity, thereby to ligate a tissue present in the body cavity in the same way as with the eight embodiment.

More specifically, the surgeon passes the free end portion of the ligature 212 under the tissue, holds the free end of the ligature 212 with the tongs 223 of the forceps 213, and pushes the operation rod 227, thereby moving the cartridge body 250 forward. The switch 341 is thereby closed, and the ligature holder 270 is rotated once around its axis. The loops L on the holder 270 are moved forward until the foremost loop is released from the holder 270. When the surgeon pulls the operation rod 227 back, the loop L released from the holder 270 is pulled, forming a knot.

As the surgeon repeats the sequence of operations described in the preceding paragraph, a second knot, a third knot, and so on will be formed, one upon another.

In the tenth embodiment, the ligature holder 270 is rotated by the driver 346. The surgeon does not need to exert so much force to ligate a tissue. Having no cam groove cut in it, the cartridge body 250 can be easily manufactured.

A ligating apparatus according to the eleventh embodiment of the invention will be described with reference to FIG. 74, FIGS. 75A and 75B, and FIG. 76. The eleventh embodiment is similar to the ninth embodiment. The components similar or identical to those of the ninth embodiment are designated at the same reference numerals and will not be described in detail.

As shown in FIG. 74, the cover 290a of the cartridge body 250 of this embodiment has a distal end portion extending from the distal end of the ligature holding section 271. The distal end of the cover 290a is cut slantwise. The cover 290a has a ligature holding notch 350 at the distal end. The notch 350 diametrically opposes the slit 291 cut also in the distal end of the cover 290a.

Figure 76:
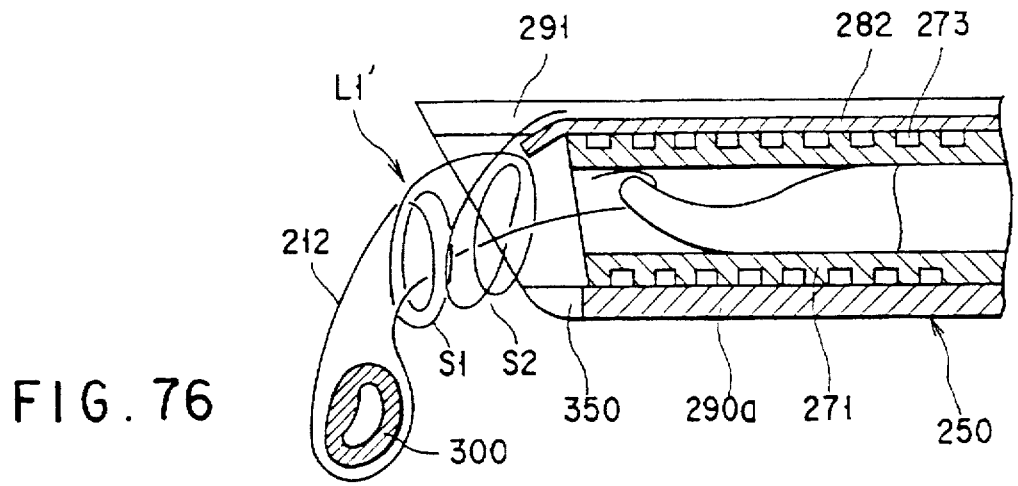
FIG. 76 is a sectional view of the distal end portion of the eleventh embodiment, explaining how the embodiment is operated to ligate a tissue.

As seen from FIG. 75A, a ligature 212 is wound around the ligature holding section 271, forming groups $L_1, L_2, \ldots$ of loops, set in the turns $M_1, M_2, \ldots$ of the helical groove 273 made in the outer surface of the section 271. The groups $L_1, L_2, \ldots$ of loops are identical. The group $L_1$, for example, consists of two double loops $S_1$ and $S_2$, each consisting of two loops, as is illustrated in FIG. 75B. The cam pin (not shown) of the forceps 213 protrudes downwards, not upwards as in the ninth embodiment as shown in FIG. 70. Once the forceps 213 is attached to the cartridge body 250, the elongated strip 282 is positioned above the forceps 213 as illustrated in FIG. 76.

A surgeon can use the eleventh embodiment, in the following manner, in order to ligate a tissue 300. At first, the surgeon passes the free end portion of the ligature 212 under the tissue 300, holds the free end of the ligature 212 with the tongs 223 of the forceps 213, and pushes the cartridge body 250 forward until the first loop group $L_1$, is released from the ligature holding section 271. Then, the surgeon operates the forceps 213 in the same way as with the first embodiment, while holding the loop group $L_1$, in the ligature holding notch 350. That is, he or she repeatedly pushes and pulls the cartridge body 250, sequentially tightening the loops $S_1$ and $S_2$ and ligating the tissue 300 with the first loop group $L_1$.

As may be understood from the above, the eleventh embodiment enables the surgeon to ligate tissues one after another, performing a few steps and spending but a short time on each tissue.

Figure 77:
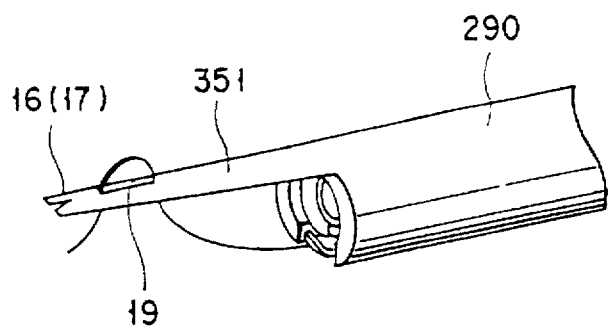
FIG. 77 is a perspective view of the distal end portion of a ligating apparatus according to a twelfth embodiment of the present invention.

FIG. 77 shows the distal end portion of a ligating apparatus according to the twelfth embodiment of this invention. The twelfth embodiment is similar to the eighth embodiment. The components similar or identical to those of the eighth embodiment are designated at the same reference numerals and will not be described in detail.

The twelfth embodiment is characterized in that a ligature holding member 351 extends from the distal end of the cover 290 which is a component of the cartridge body 250. The member 351 is identical to the ligature holding section 6 used in the first embodiment. That is, the member 351 has a notch 16 cut in its distal end, for guiding a ligature 212. A cutter 17 is provided in the notch 16. The member 351 also has a slit 19 in the end portion, which extends in the lengthwise direction of the member 351. It is in this slit 19 that the free end of the ligature 212 is held and directed downwards. The slit 19 has the same shape, for holding the ligature 212 in the same manner, as in the first embodiment.

The twelfth embodiment is operated in the same way to pass the free end portion of the ligature 212 under the tissue of interest and hold the end portion of the ligature 212 by the tongs of the forceps 213. In order to ligate the tissue thereafter, it suffices to operate the twelfth embodiment in the same way as the eighth embodiment. The surgeon needs only to manipulate one forceps to wrap the ligature 212 around the tissue and to ligate the same. Since the cutter 17 is provided on the cartridge body 250, the surgeon can use a sharp cutter every time he or she replaces the cartridge with a new one.

A ligating apparatus according to the thirteenth embodiment of the present invention will be described, with reference to FIGS. 78A and 78B and FIGS. 79A to 79D.

Figures 78A, 78B:
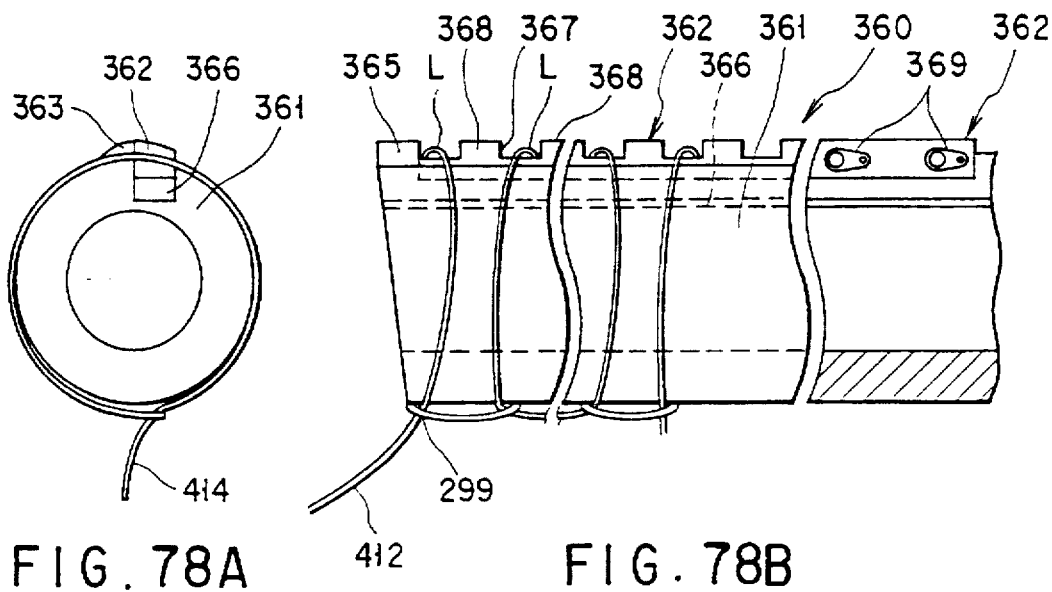
FIG. 78A is a front view of a ligating apparatus according to a thirteenth embodiment of the invention.
FIG. 78B is a side view of a section of the thirteenth embodiment.

This ligating apparatus comprises a hollow cylindrical cartridge 360 and a forceps (not shown) inserted in the cartridge 360, capable of moving back and forth. The cartridge 360 is made up of a cartridge body 361 and a loop feeding member 362. The loop feeding member 362 is slidably mounted on the cartridge body 361. As shown in FIG. 78A and 78B, the cartridge body 361 has a loop holder 363 on its outer surface. The loop holder 363 extends parallel to the axis of the cartridge body 361. The holder 363 has grooves 364 and projections 365 alternately arranged, forming a row extending in the lengthwise direction of the body 361. The foremost projection 365 is located at the very distal end of the loop holder 363.

The loop feeding member 362 extends parallel to the loop holder 363. The member 362 is loosely fitted in the groove 366 made in the outer circumferential surface of the cartridge body 361 and can slide back and forth. The member 362 has grooves 367 and projections 368 alternately arranged, forming a row extending in the lengthwise direction of the loop feeding member 362. The foremost groove 367 is located at the very distal end of the loop feeding member 362.

Figure 79A:
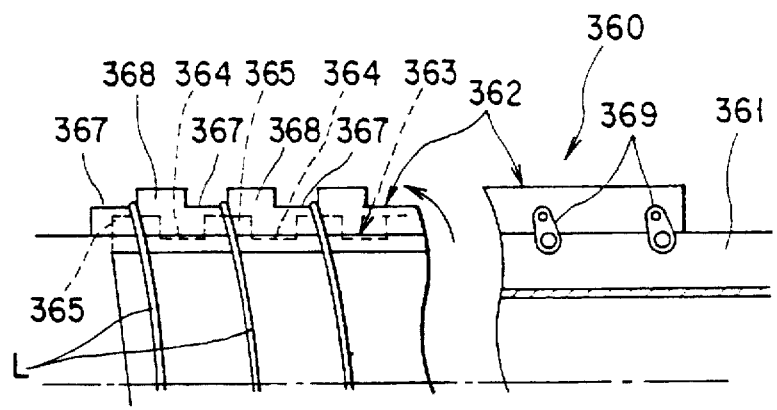
FIGS. 79A to 79D are side views of the thirteenth embodiment, explaining how the embodiment is operated to ligate a tissue.
Figure 79B:
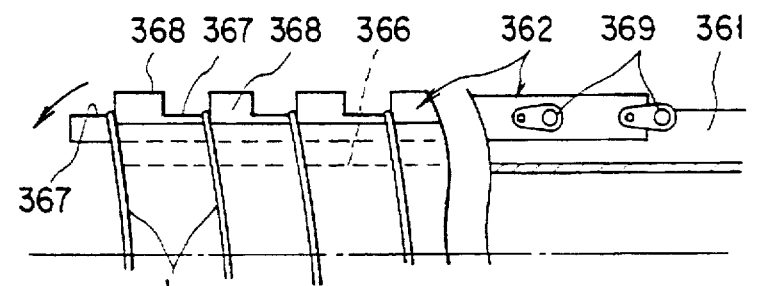
Figure 79C:
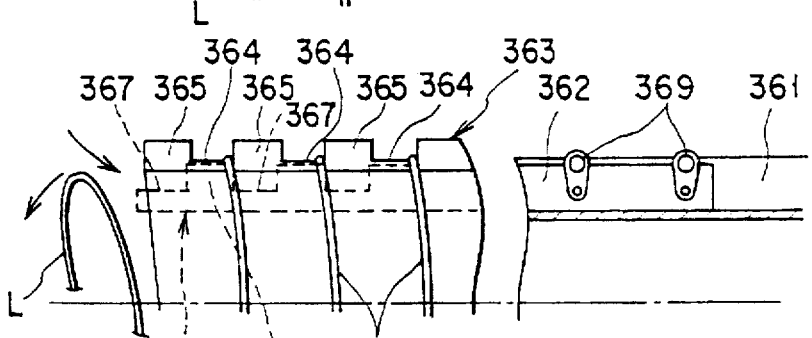
Figure 79D:
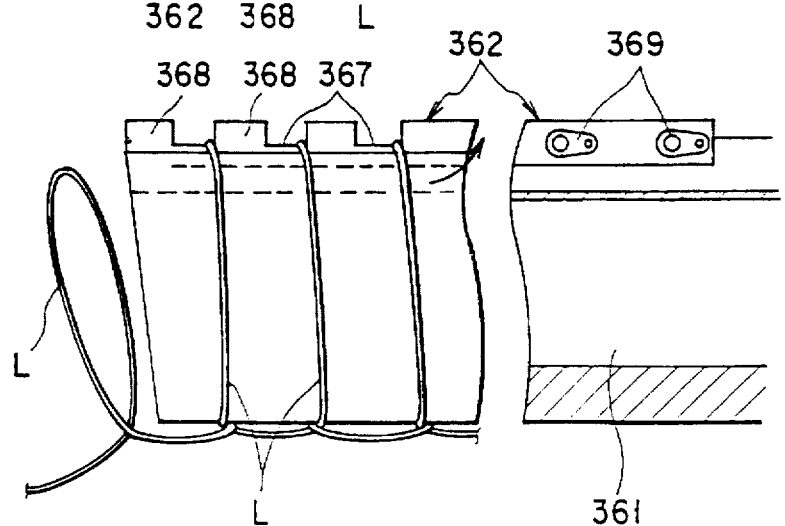

The loop feeding member 362 has its proximal end connected to a cam mechanism 369. The cam mechanism 369 can rotate the loop feeding member 362 in a circle, while maintaining the member 362 parallel to the loop holder 363. As the member 36 2 is thus rotated, its grooves 367 move forward, while moving up above the grooves 364 of the loop holder 363, as shown in FIG. 79A. Then, the grooves 367 move down to the same level as the grooves 364 of the loop holder 363 as shown in FIG. 79B. Next, the grooves 367 move backwards, while moving down below the grooves 364 of the loop holder 363, as illustrated in FIG. 79C. Further, the grooves 367 again move up to the same level as the grooves 364 of the loop holder 363 as shown in FIG. 79D. Finally, the grooves 367 return to the initial position shown in FIG. 79A. The loop feeding member 362 is set at its highest position when the cam mechanism 369 takes the position shown in FIG. 79A, and at its lowest position when the cam mechanism 369 assumes the position shown in FIG. 79C.

The cam mechanism 369 is driven by a driver (not shown). The driver may be a type which drives the cam of the mechanism directly or a type which drives the cam as the forceps is moved back and forth through the cartridge 360. If the driver is the second-mentioned type, it should better drive the cam when the distal end of the forceps is pulled into the loop holder 363 of the cartridge body 361. The last of the loops L held by the holder 363 has its proximal end fastened to the holder 363. The loops L, which are of the same type as those used in the eighth embodiment, are wound around the cartridge body 361, placed in the grooves 364 of the holder 363 and the grooves 367 of the loop feeding member 362.

It will be explained how a surgeon operates the thirteenth embodiment to ligate a tissue present in a patient's body cavity.

At first the surgeon inserts the forceps into the cartridge body 361. He or she then inserts the distal end portion of the ligating apparatus into the body cavity. The surgeon manipulates the forceps, passing the ligature 212 under the tissue and holding the distal end of the ligature 212. Thereafter, the surgeon pushes the cartridge body 361 forward until it covers the distal end of the forceps. Then, he or she drives the cam mechanism 369, whereby the loop feeding member 362 is pushed forward, while moving upwards from the position shown in FIG. 78B. The loops L in the grooves 367 of the member 362 are thereby moved up above the projections 365 as shown in FIG. 79A. The member 362 is further moved forward, and the loops L are shifted forward, each from one groove 364 into the immediately preceding groove 364, as is illustrated in FIG. 79B. As the cam mechanism 369 is further driven, the loop feeding member 362 is pulled back. The foremost loop L is thereby released from the foremost groove 364 of the loop holder 363 as shown FIG. 79C. The free end portion of the ligature 212, held at the distal end of the forceps 213, passes through the loop L released from the cartridge body 361. As the loop feeding member 362 is pulled further back, the forceps and the free end portion of the ligature 212 are pulled into the cartridge body 361. When the member 362 reaches its initial position, it catches the loops L in the grooves 367 as shown in FIG. 79D. When the forceps is further pulled into the cartridge body 361, the released loop L is closed, forming a knot and squeezing the tissue.

To form a second knot, a third knot, and so on, to ligate the tissue more firmly, it is sufficient for the surgeon to operate the apparatus repeatedly, in the same manner as described in the preceding paragraph.

A ligating apparatus according to the fourteenth embodiment of the invention will be described, with reference to FIG. 80, FIGS. 81A and 81B, and FIGS. 82 to 85. The apparatus comprises a cartridge body and a forceps. The cartridge body is identical to its counterpart of the ninth embodiment, and only the forceps will be described.

Figure 80:
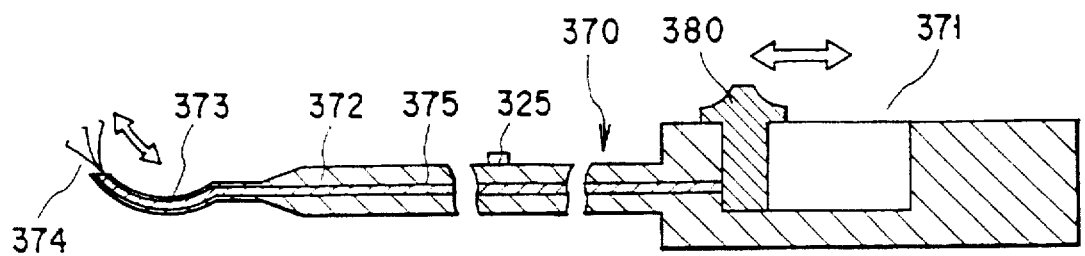
FIG. 80 is a sectional view of the forceps which is a component of a ligating apparatus according to a fourteenth embodiment of the invention.
Figure 81A:
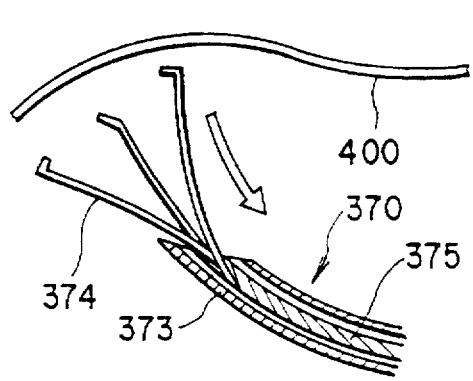
FIGS. 81A and 81B and FIGS. 82 to 85 are diagrams, explaining how the fourteenth embodiment is operated to ligate a tissue.
Figure 81B:
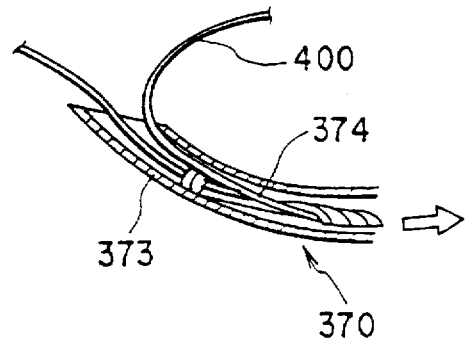

As shown in FIG. 80, the forceps 370 is comprised of an operation section 371, a hollow shaft 372 and a hollow needle 373. The operation section 371 is coupled to the proximal end of the shaft 372. The needle 373 is connected to the distal end of the shaft 372. An operation wire 375 passes through the shaft 372 and the needle 373, with its proximal end fastened to a slider 380 provided in the operation section 371. Elastic claws 374 are connected to the distal end of the operation wire 375. The claws 374, flaring at their distal ends, are closed together when they are pulled in part into the needle 373 as the operation wire 375 is pulled back. They regain their flaring shape due to their elasticity, when they are released from the needle 373 as the operation wire 375 is pushed forward.

As illustrated in FIG. 80, a cam pin 325 protrudes from the outer surface of the shaft 372 of the forceps 370. The cam pin 325 remains fitted in the cam groove 274' (of the type shown in FIG. 69) cut in the inner surface of the cartridge body (not shown), as in the case of the ninth embodiment. The distal end portion of the needle 373 is bent, but not so much that the distal end would extend outwards from the diameter of the shaft 372.

It will be explained how a surgeon operates the thirteenth embodiment to suture a tissue 410 present in a patient's body cavity.

Figure 82:
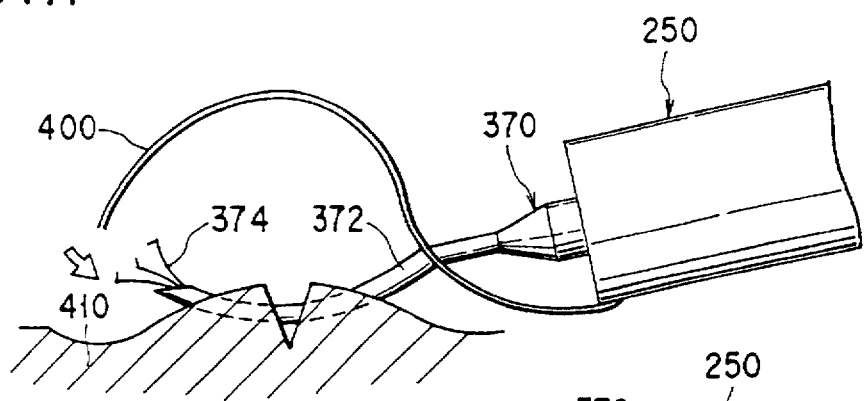
Figure 83:
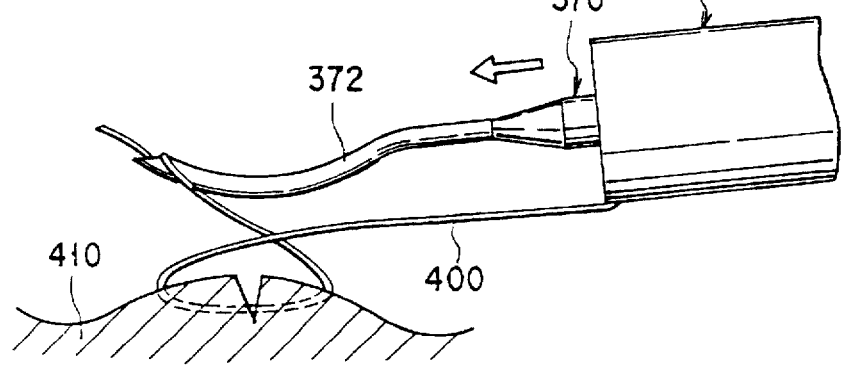
Figure 84:
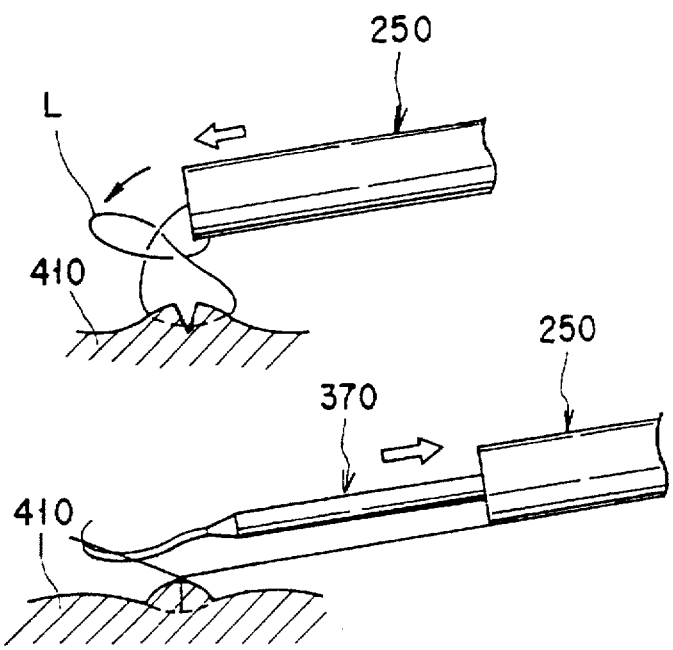
Figure 85:
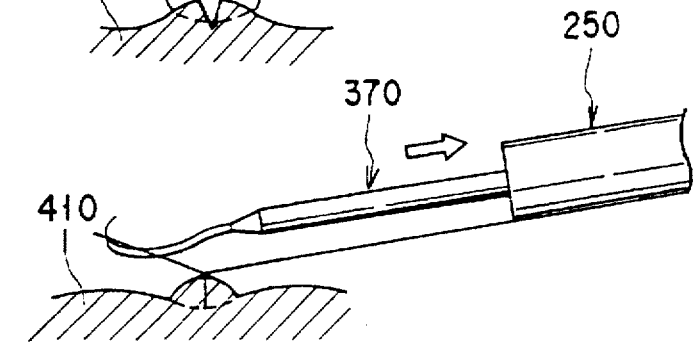

The surgeon inserts the forceps 370 into the cartridge body 250, assembling the ligating apparatus. The surgeon then inserts the distal end portion of the ligating apparatus into the body cavity. He or she passes the needle 373 through the tissue 410, with the claws 374 completely pulled in the needle 373. The surgeon pushes the claws 374 from the needle 373, whereby the claws 374 flares, as is illustrated in FIG. 82. The surgeon holds the distal end of a suture 400 in the claws 374 by pulling the claws 374 back into the needle 373. This done, he or she pulls the needle out of the tissue 410, whereby the suture 400 is passed through the tissue 410 as shown in FIG. 83. Thereafter, the surgeon manipulates the forceps 370 in the same way as with the ninth embodiment, releasing a loop of the suture 400 from the cartridge body 250 as shown in FIG. 84. The surgeon then tightens the released loop L, forming a knot and thus suturing the tissue 410.

Figure 86:
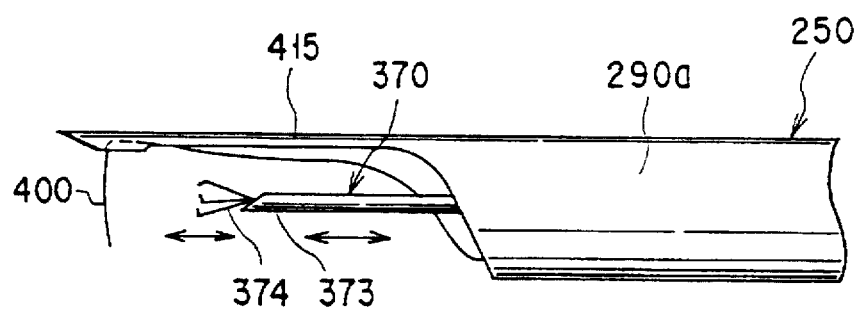
FIG. 86 is a side view showing the distal end portion of a ligating apparatus according to a fifteenth embodiment of the present invention.
Figure 87:
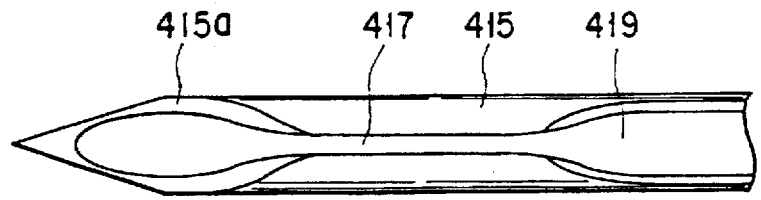
FIG. 87 is a bottom view of the distal end portion of the cover incorporated in the fifteenth embodiment.
Figure 88:
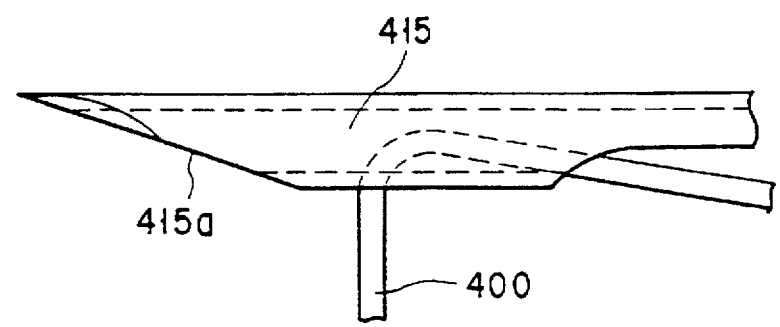
FIG. 88 is a side view of the distal end portion of the cover incorporated in the fifteenth embodiment.

A ligating apparatus according to the fifteenth embodiment of the invention will be described, with reference to FIGS. 86 to 88. The apparatus comprises a cartridge body and a forceps and is similar to the fourteenth embodiment. Therefore, the components similar or identical to those of the fourteenth embodiment are designated at the same reference numerals and will not be described in detail.

A needle member 415 is connected to the distal end of the cover 290a of the cartridge body 250. The needle member 415 consists of a hollow cylindrical distal end portion and a trough-shaped proximal end portion. The distal end portion a slant distal end 415a which extends along the axis of the needle member 415, as illustrated in FIG. 87. The slit 417 is slightly less wide than the suture 400 is thick. The suture 400 can therefore be held in the slit 417. The slit 417 is continuous to the opening of the trough-shaped proximal end portion.

The suture 400 is fastened at one end to the cartridge body 250. Its free end portion is passed through the needle member 415, guided through the slit 417, held therein, and extends downwards, as shown in FIG. 88. That portion of the suture 400 which hangs from the needle member 415 should be long enough to be caught in the claws 374 protruding from the needle 373. The distal end portion of the needle 373 is straight, not bent as that of the needle of the fourteenth embodiment.

It will be explained how a surgeon operates the ligating apparatus of the fifteenth embodiment to suture two tissues together, with reference to FIGS. 89A to 89D.

Figure 89A:
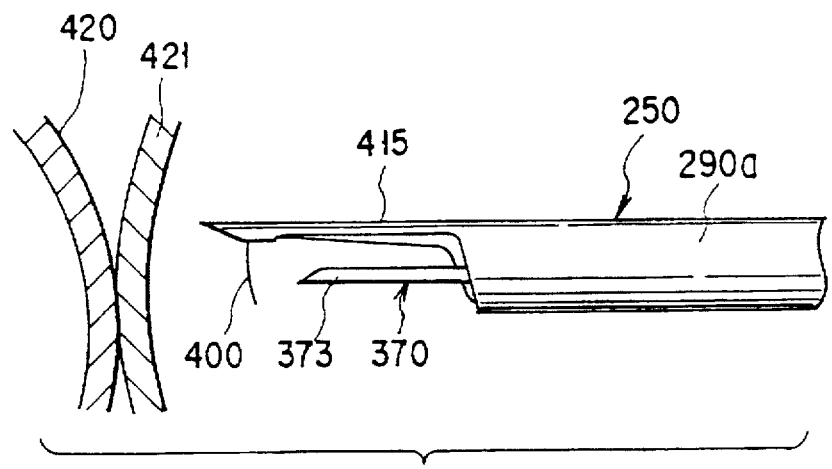
FIGS. 89A to 89D are diagrams explaining how the fifteenth embodiment is operated to suture a tissue.
Figure 89B:
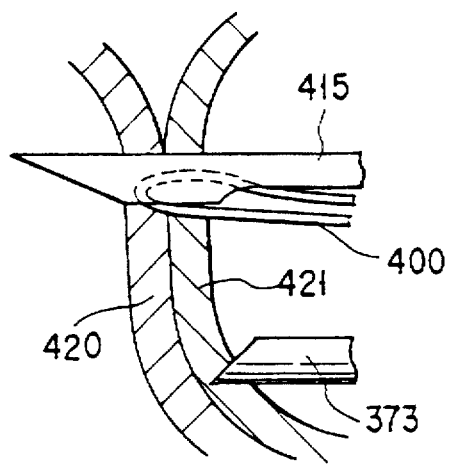
Figure 89C:
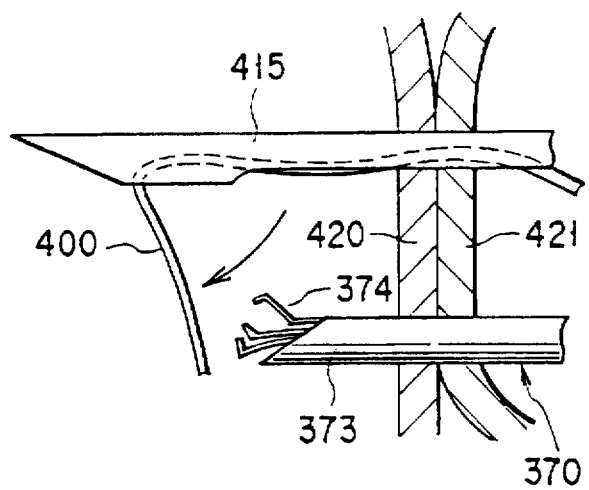
Figure 89D:
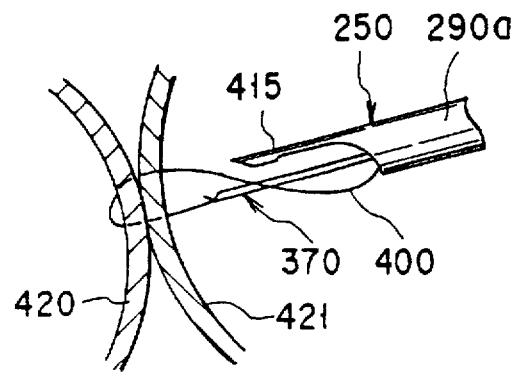

The surgeon passes both the needle 373 of the forceps 370 and the needle member 415 of the cartridge body 250 through the tissues 420 and 421 as shown in FIGS. 89A and 89B. At this time, the suture 400 held by the needle 415 is bent double as shown in FIG. 89B and passes through both tissues 420 and 421. The free end portion of the suture 400 hangs down as shown in FIG. 89C when the hollow cylindrical distal end portion of the needle member 415 projects from the tissue 420. Thereafter, the surgeon operates the ligating apparatus in the same manner as the fourteenth embodiment, thus suturing the tissues 420 and 421 together as shown in FIG. 89D. With the fourteenth embodiment it is easy for the surgeon to suture two or more tissue layers together.

Figure 90:
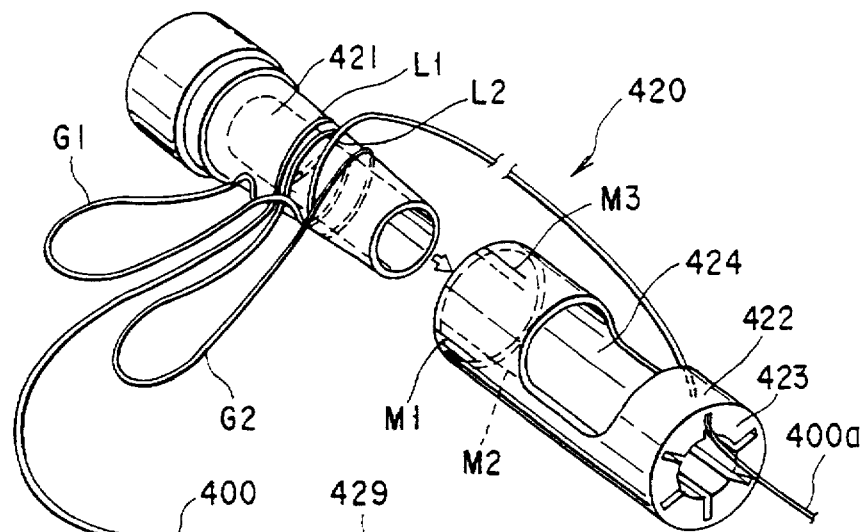
FIG. 90 is an exploded view of the cartridge incorporated in a ligating apparatus according to a sixteenth embodiment of this invention.
Figure 91:
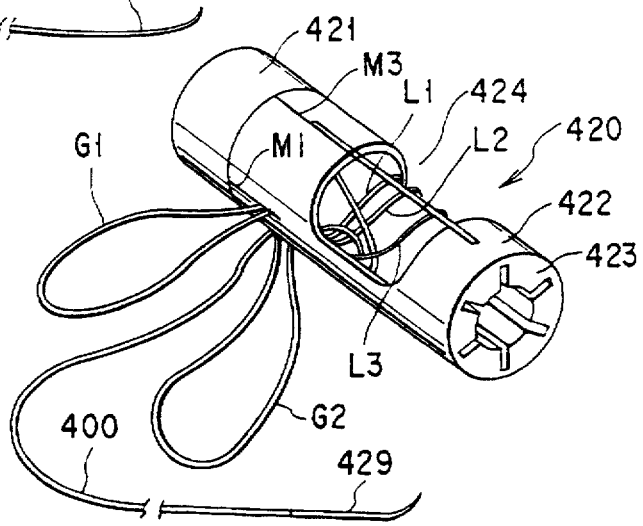
FIG. 91 is a perspective view of the cartridge shown in FIG. 90.

A ligating apparatus according to the sixteenth embodiment of this invention will be described, with reference to FIGS. 90 and 91. This ligating apparatus has a cartridge 420 of the specific type shown in FIG. 91. As shown in FIG. 90 which is an exploded view, the cartridge 420 comprises an inner cylinder 421 and an outer cylinder 422, both being hollow ones.

The outer cylinder 422 has an opening 424, allowing access into the outer cylinder 422. It has a forceps holding section 423 at its proximal end and three slits $M_1$, $M_1$ and $M_3$ in its distal end. The suture 400 is wound around the inner cylinder 422, forming loops $L_1$, $L_2$ and $L_3$. The loops $L_1$ to $L_3$ are retained in the outer cylinder 421 once the inner cylinder 422 has been inserted into the outer cylinder 421. Three other portions of the suture 400 forms three open loops $G_1$, $G_2$ and $G_3$. The first open loop $G_1$ connects the loop $L_1$ to the loop $L_2$. The second open loop $G_2$ connects the loop $L_2$ to the loop $L_3$. The third open loop $G_3$ connects the loop $L_3$ to one end portion 400a, which is fastened to the outer cylinder 422. The open loops $G_1$, $G_2$ and $G_3$ are held at one part in the slits $M_1$ to $M_3$ of the outer cylinder 422, respectively.

It will be explained how a surgeon operates the apparatus according to the sixteenth embodiment to suture an tissue having a cut, with reference to FIGS. 92 to 97.

Figure 92:
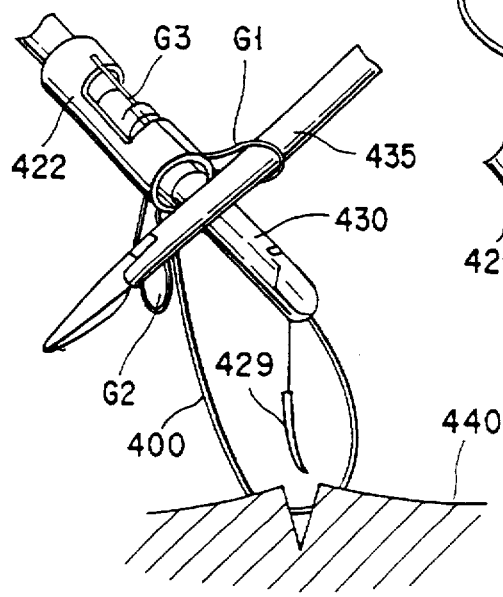
Figure 93:
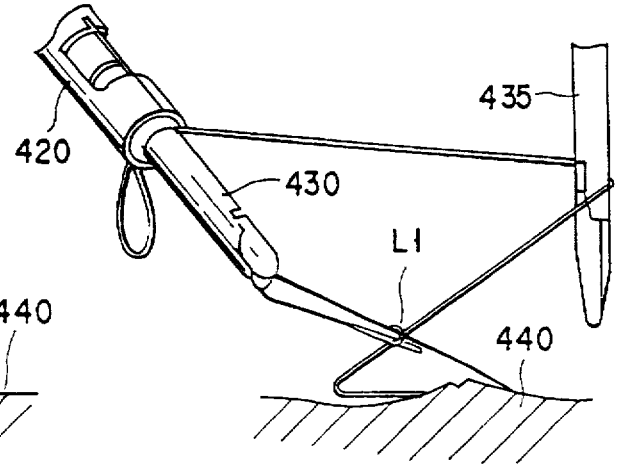
Figure 97:
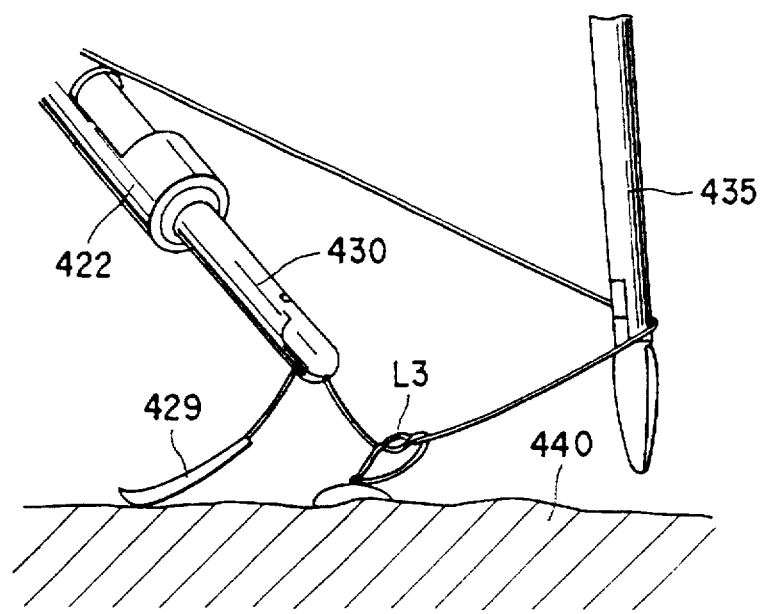

At first, the surgeon inserts a first forceps 430 into the cartridge 420 from the forceps holding section 423 as shown in FIG. 92, pushing the inner cylinder 421 from the outer cylinder 422. The loops $L_1$ to $L_3$ are thereby transferred from the inner cylinder 421 onto the forceps 430. The surgeon then manipulates the first forceps 439, passing the needle 429 connected to the distal end of the suture 400, through the tissue 440. He or she holds the free end portion of the suture 400 by the first forceps 430. The surgeon passes a second forceps 435 through the loop $G_1$ and moves the forceps 435, thereby releasing the loop $G_1$ from the slit $M_1$ of the outer cylinder 422. The second forceps 435 is further moved, whereby the loop $L_1$ located in the loop $G_1$, is released from the second forceps 435, as illustrated in FIG. 93. The free end of the suture 400 is thereby positioned at the center of the loop $L_1$. The surgeon moves the second forceps 435, moving the loop $L_1$ over the needle 429. The free end of the suture 400 and the loop $G_1$ are pulled, tightening the loop $L_1$. As a result, the tissue 440 is sutured, forming a first knot 422 on the suture 400, as is shown in FIG. 94. Next, the surgeon passes the second forceps 435 through the loop $G_2$, pulling the loop $L_2$ and forming a second knot on the first knot 422. To form, if necessary, a third knot, the surgeon passes the second forceps 435 through the loop $G_3$ as shown in FIG. 95. He or she then pulls the loop $L_3$ as shown in FIGS. 96 and 97, forming the third knot in addition to the first and second knots.

Any loop L released has its one end connected to the next loop L still wound around the second forceps 435. It can therefore be tightened, merely by moving the second forceps 435 passed through the open loop G. The sixteenth embodiment is desired to form at most three knots. Nevertheless, it may be re-designed to form four or more knots, only by forming four or more slits M in the distal end of the outer cylinder 422, for holding four or more loops L.

Figure 98:
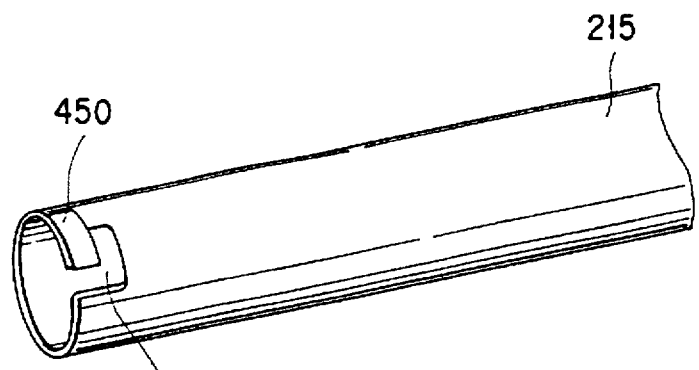
FIG. 98 is a perspective view of a ligating apparatus according to a seventeenth embodiment of the invention.
Figure 99:
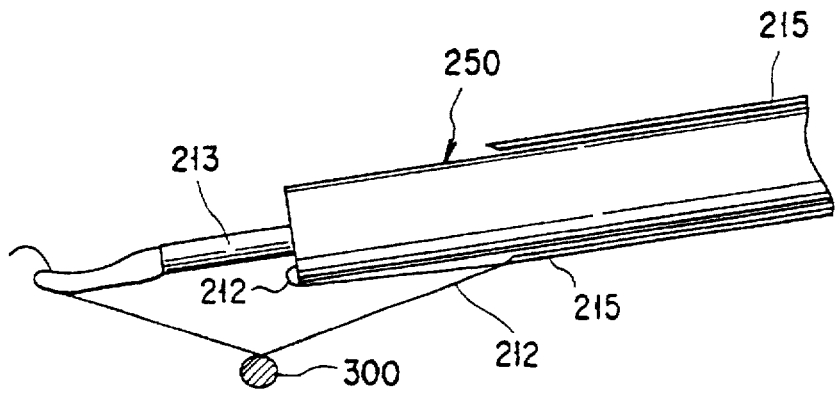
FIG. 99 is a side view of the distal end portion of the seventeenth embodiment, explaining how the embodiment is operated to ligate a tissue.

FIGS. 98 and 99 show a ligating apparatus according to the seventeenth embodiment of the present invention. This embodiment is identical to the eighth embodiment, except that the sheath 215 has at its distal end a cutter 450 and a ligature guiding slit 451 as illustrated in FIG. 89.

With the seventeenth embodiment it is possible for a surgeon to cut a ligature 212 easily. That is, in order to cut the ligature 212 the surgeon needs only to pull the cartridge body 250 into the sheath 215, thus pulling the ligature 212 through the guiding slit 451, and then push the cartridge body 250 forward, thereby pressing the ligature 212 onto the cutter 450.

FIGS. 100A and 100B illustrates a ligating apparatus according to the eighteenth embodiment of the present invention. This embodiment is almost identical to the eighth embodiment. The components similar or identical to those of the eighth embodiment are designated at the same reference numerals and will not be described in detail.

The ligating apparatus according to the eighteenth embodiment comprises a forceps section and a cartridge. The forceps section is comprised of a sheath 215 and a forceps 213 which are shown in FIGS. 100A and 100C, respectively. The cartridge is comprised of a operation section 217 and a cartridge body 250 which are shown in FIGS. 100C and 100B, respectively. The cartridge body 250 has a case 280b, which is, so to speak, a combination of the case 280 and cover 290 incorporated in the eighth embodiment. The cartridge operating section 217 has a hollow cylinder 288 which is fitted in the proximal end 284 of the case 280b. The hollow cylinder 288 has a gear 340 on the front. The gear 340 can be set in mesh with a gear 345 provided on the proximal end of the ligature holder 270. When the cylinder 288 is rotated, the holder 270 will be rotated. The case 480 has a cam groove 274 (of the type shown in FIG. 54). The arm 29 has a cam pin 230 projecting from its distal end. The cam pin 230 is loosely fitted in the cam groove 274 of the case 480.

Thus, as the cartridge body 250 is pushed forward, the case 480 and, hence, the gear 340 are rotated, rotating the ligature holder 270. The foremost loop L of the ligature 212 is thereby released from the holder 270. Since the cartridge body 250 need not be rotated, it can be easily made.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A ligating apparatus comprising:
    a ligature applying body having a distal end with a ligature holding section thereat for holding one end of a ligature;
    a ligature holder movable relative to the ligature applying body, said ligature holder including:
        a through hole through which the ligature-applying body is to be moved,
        ligature holding means for holding at least one part of the ligature to the ligature holder, and
        a ligature retaining section for retaining the ligature and through which the through bore extends;
    ligature winding means for holding the ligature in a wound relation around the ligature applying body or the ligature holder, thereby to form at least one loop to be tightened to form a knot;
    loop releasing means for releasing said at least one loop from the ligature applying body or the ligature holder when the ligature applying body is pulled into the through hole of the ligature holder; and
    loop tightening means as part of the ligature holding section of the ligature applying body for tightening said at least one loop released from the ligature applying body or the ligature holder, when the ligature applying body and the ligature holder are moved relative to each other.

2. The apparatus according to claim 1, wherein said ligature winding means is a ligature holding member which is removably connected to said ligature holder, which has an outer surface for holding said at least one loop, and from which said at least one loop is to be transferred onto said ligature applying body.

3. The apparatus according to claim 1, wherein said loop releasing means has a surface which is located at a distal end of said through hole and on which said at least one loop abuts until said at least one loop is released from the ligature applying body as said ligature holding section holding said one end of the ligature is pulled into said ligature holder.

4. The apparatus according to claim 1, wherein said ligature applying body passes through said ligature holder and is capable of moving back and forth.

5. The apparatus according to claim 1, wherein said ligature winding means includes a helical groove made in an outer surface of said ligature retaining section and is capable of retaining said at least one loop.

6. The apparatus according to claim 5, wherein said loop releasing means has rotating means for rotating said ligature retaining section, thereby to release said at least one loop first from said helical groove and ultimately from said ligature retaining section.

7. The apparatus according to claim 6, wherein said rotating means has a pin provided on one of said ligature applying body and said ligature holder, and a cam groove formed in the other of said ligature applying body and said ligature holder, for guiding said pin to rotate said ligature retaining section as said ligature applying body is pulled into said ligature holder.

8. The apparatus according to claim 7, further comprising operation means for moving said ligature holder back and forth with respect to the ligature applying body, thereby to move said pin along said cam groove.

9. The apparatus according to claim 6, wherein said rotating means comprises a driving gear and a driven gear provided on said ligature retaining section and set in mesh with said driving gear, and rotates said ligature retaining section by transmitting a rotation of said driving gear to said driven gear.

10. The apparatus according to claim 6, further comprising rotation inhibiting means for inhibiting said at least one loop retained in said helical groove from rotating.

11. The apparatus according to claim 10, wherein said rotating means moves forward said at least one loop along said helical groove while said rotating inhibiting means is inhibiting said at least one loop retained in said helical groove from rotating.

12. The apparatus according to claim 11, wherein said ligature holding means is moved forward along said helical groove, together with said at least one loop.

13. The apparatus according to claim 12, further comprising means for preventing said ligature holding means from slipping from said helical groove while said ligature holding means is moving along said helical groove.

14. The apparatus according to claim 6, further comprising a protective cover protecting said ligature holder.

15. The apparatus according to claim 14, wherein said protective cover has a notch, and that portion of said at least one loop which remains on said ligature holder can be seen through the notch.

16. The apparatus according to claim 14, wherein said protective cover is made of transparent material, and that portion of said at least one loop which remains on said ligature holder can be seen through said protective cover.

17. The apparatus according to claim 1, wherein said ligature applying body and said ligature holder are removably connected to each other.

18. The apparatus according to claim 1, wherein said ligature holder comprises a hollow cylindrical cartridge and a sheath removably connected to the cartridge, said cartridge having said ligature holding means and said ligature retaining section.

19. The apparatus according to claim 1, wherein a needle is connected to the other end of the ligature.

20. The apparatus according to claim 1, wherein said ligature applying body passes through said ligature holder and is sealed therefrom in airtight fashion.

21. The apparatus according to claim 1, wherein said ligature holding means is a ligature guiding hole made in said ligature holder having a diameter larger than a diameter of the ligature and smaller than an outer diameter of a tag formed on the ligature.

22. The apparatus according to claim 1, wherein said ligature holding means fastens the ligature to said ligature holder.

23. The apparatus according to claim 1, wherein said ligature holder has ligature catching means for preliminarily holding the other end of the ligature.

24. The apparatus according to claim 23, wherein the other end of the ligature held by the ligature catching means hangs almost vertically from the ligature holder toward an axis of said ligature holder.

25. The apparatus according to claim 24, wherein said ligature catching means is spaced apart from the axis of said ligature holder by a predetermined distance.

26. The apparatus according to claim 1, wherein said ligature holder has a knot holding groove located at a distal end of said through hole, for holding a knot formed by tightening said at least one loop.

27. The apparatus according to claim 1, wherein said loop releasing means has a loop releasing member, each for releasing loops of the ligature, one by one.

28. The apparatus according to claim 27, wherein said loop releasing means comprises a helical groove made in an outer surface of said ligature retaining section, for retaining the loops of the ligature, and rotating means for rotating said ligature retaining section, thereby to release the loops of the ligature from said helical groove and ultimately from said ligature retaining section.

29. The apparatus according to claim 1, wherein said ligature winding means has loop retaining means for retaining a plurality of loops of the ligature one by one on said ligature applying body or said ligature holder.

30. The apparatus according to claim 29, wherein said loop retaining means includes a helical groove made in an outer surface of said ligature retaining section, for retaining said plurality of loops.

31. The apparatus according to claim 29, wherein said loop retaining means comprises a plurality of walls provided on said ligature holder, for separating said plurality of loops from one another.

32. The apparatus according to claim 1, wherein said ligature applying body extends from a distal end of said ligature holder for a distance longer than a length of that portion of the ligature which form said at least one loop.

33. The apparatus according to claim 1, wherein said ligature holder has a blade for cutting the ligature.

34. The apparatus according to claim 1, wherein said loop tightening means includes a projection of said ligature applying body protruding from said ligature holder.

35. The apparatus according to claim 1, wherein said ligature holding means winds a plurality of loops of the ligature around said ligature applying body or said ligature holder, said loops being connected one to another.

36. A ligating apparatus comprising:
a single ligature forming groups of loops, each group comprising a plurality of loops which are to be tightened to form knots;
ligature holding means for holding at least one part of the ligature and the groups of loops, thereby holding said ligature; and
loop releasing means for releasing the loops of said groups, one by one, from the ligature holding means while retaining the ligature extending from a released loop by the ligature holding means, whereby a first loop is released and tightened before a second loop is released from the ligature holding means.

37. The apparatus according to claim 36, wherein said ligature holding means has a ligature applying body passing through said groups of loops and having at a distal end a ligature holding section for holding a free end of the ligature.

38. The apparatus according to claim 37, wherein said ligature holding means has a tubular body which has ligature fastening means for fastening at least one part of the ligature, and said ligature applying body passes through said tubular body and is capable of projecting from and receding into a distal end of said tubular body, for holding the groups of loops.

39. The apparatus according to claim 38, wherein said loop releasing means has separating means provided on said tubular body, for separating the loops on said ligature applying body, from one another, and for releasing the loops, one by one, while cooperating with said ligature applying body moving forward or backward with respect to said tubular body.

40. The apparatus according to claim 37, wherein said ligature holding means has a tubular ligature holder for holding the groups of loops, the tubular ligature holder having a ligature holding section for holding at least one part of the ligature, and said ligature applying body passes through said ligature holder and is capable of projecting from and receding into a distal end of said ligature holder.

41. The apparatus according to claim 40, wherein said loop releasing means releases the loops held on said ligature holder one by one when said ligature applying body is pulled in to said ligature holder.

42. The apparatus according to claim 40, wherein ligature holding section winds the loops around said ligature holder.

43. A ligating apparatus comprising:

a single ligature forming groups of loops, each group comprising a plurality of loops which are to be tightened to form knots;

ligature holding means for holding at least one part of the ligature and the groups of loops, thereby holding said ligature; and loop holding means for holding the loops of said groups on the ligature holding means, such that the loops are releasable from the ligature holding means one by one, said loop holding means retaining non-released loops on the ligature holding means, and retaining the ligature extending from a released loop on the ligature holding means, whereby a first loop is released and tightened before a second loop is released from the ligature holding means.

44. The apparatus according to claim 43, wherein said ligature holding means comprises a tubular body which has a ligature holding section for holding at least one part of the ligature, and a ligature applying body which passes through said tubular body, which is capable of projecting from and receding into a distal end of said tubular body, for holding the groups of loops and which has at a distal end a ligature holding section for holding a free end of the ligature.

45. The apparatus according to claim 43, wherein said ligature holding means has a tubular ligature holder for holding the group of loops, the tubular ligature holding having a ligature holding section for holding at least one part of the ligature, and said loop holding means comprises a helical groove made in an outer surface of said ligature holder, for retaining the loops.

46. The apparatus according to claim 43, further comprising loop releasing means for releasing the loops, one by one, from said ligature holding means.

47. The apparatus according to claim 43, wherein said ligature holding section winds the loops around said ligature holder.

48. A ligating apparatus comprising:

a single ligature forming groups of loops, each group comprising a plurality of loops which are to be tightened to form a plurality of continuous knots;

ligature holding means for holding the groups of loops of the ligature, thereby holding said ligature; and loop releasing means for releasing the loops of each group, one by one, from the ligature holding means; and loop tightening means for pulling a free end of said ligature through a loop released from said loop holding means, and then tightening said released loop prior to releasing another said loop.

49. A ligating apparatus comprising:

a ligature forming groups of loops, each group comprising a plurality of loops which are to be tightened to form a plurality of continuous knots;

ligature holding means for holding the groups of loops of the ligature, thereby holding said ligature; and loop holding means for holding the loops of each group, so as to be releasable one by one, from the ligature holding means.

50. A ligating apparatus according to claim 37, further comprising tightening means for tightening the knots.

* * * * *

UNITED STATES PATENT AND TRADEMARK OFFICE
CERTIFICATE OF CORRECTION

PATENT NO. : 5,797,928
DATED : August 25, 1998
INVENTOR(S) : KOGASAKA, Takahiro

It is certified that error appears in the above-identified patent and that said Letters Patent is hereby corrected as shown below:

Column 46, after the last line, add the following claim 51:

--51. A ligating apparatus according to claim 36, wherein said ligature holding means has a hole for holding a medical instrument to pass the medical instrument through the loops of the ligature.--

Signed and Sealed this

Sixth Day of July, 1999

Attest:

Q. TODD DICKINSON

*Attesting Officer*     Acting Commissioner of Patents and Trademarks